(12) United States Patent
Davidson et al.

(10) Patent No.: US 11,229,758 B2
(45) Date of Patent: Jan. 25, 2022

(54) PERSONAL VAPORIZING DEVICE WITH SLIDABLE CART

(71) Applicant: Syqe Medical Ltd., Tel-Aviv (IL)

(72) Inventors: Perry Davidson, Tel-Aviv (IL); Binyamin Schwartz, Sde Eliezer (IL); Aaron Schorr, Doar-Na Misgav (IL); Nimrod Reshef, LeHavim (IL); Eran Oren, Tel-Aviv (IL); Be'eri Katznelson, Kiryat-Tivon (IL)

(73) Assignee: Syqe Medical Ltd., Tel-Aviv (IL)

(*) Notice: Subject to any disclaimer, the term of this patent is extended or adjusted under 35 U.S.C. 154(b) by 368 days.

(21) Appl. No.: 16/069,187

(22) PCT Filed: Jan. 11, 2017

(86) PCT No.: PCT/IL2017/050030
§ 371 (c)(1),
(2) Date: Jul. 11, 2018

(87) PCT Pub. No.: WO2017/122196
PCT Pub. Date: Jul. 20, 2017

(65) Prior Publication Data
US 2019/0001087 A1    Jan. 3, 2019

Related U.S. Application Data

(60) Provisional application No. 62/277,060, filed on Jan. 11, 2016.

(51) Int. Cl.
*A61M 15/06*    (2006.01)
*A61M 15/00*    (2006.01)
(Continued)

(52) U.S. Cl.
CPC ............. *A61M 15/06* (2013.01); *A24F 40/30* (2020.01); *A24F 40/42* (2020.01); *A24F 40/485* (2020.01);
(Continued)

(58) Field of Classification Search
CPC ...... A24F 47/00; A24F 47/002; A24F 47/004; A24F 47/006; A24F 47/008; A24F 40/20;
(Continued)

(56) References Cited

U.S. PATENT DOCUMENTS 4,735,358 A * 4/1988 Morita ................ A01M 1/2072
                                                        206/389
5,415,162 A    5/1995 Casper et al.
(Continued)

FOREIGN PATENT DOCUMENTS

CN    1416357    5/2003
CN    2579444    10/2003
(Continued)

OTHER PUBLICATIONS

Request for Substantive Examination dated Aug. 29, 2019 From the National Institute of Intellectual Property, Ministry of Justice of Kazakhstan Re. Application No. 2018.0537.1. (4 Pages).
(Continued)

*Primary Examiner* — Kathryn E Ditmer

(57) ABSTRACT

According to some embodiments there is provided a device configured for releasing at least one substance from source material, comprising: a housing; a plurality of source material sections positioned at fixed locations with respect to the housing; a plurality of airflow paths, each airflow path associated with at least one source material section; each airflow path associated with at least one blocking element which prevents flow of air through the path; and an actuator operably coupled to the blocking element, the actuator
(Continued)

configured for unblocking the airflow path of at least one selected source material section to allow flow of air to and through source material within the selected section.

22 Claims, 34 Drawing Sheets

(51) Int. Cl.
*A61M 11/04* (2006.01)
*A24F 40/30* (2020.01)
*A24F 40/42* (2020.01)
*A24F 40/20* (2020.01)
*A24F 40/485* (2020.01)
*A61M 16/00* (2006.01)

(52) U.S. Cl.
CPC ......... *A61M 11/041* (2013.01); *A61M 11/042* (2014.02); *A61M 15/002* (2014.02); *A61M 15/0003* (2014.02); *A61M 15/0033* (2014.02); *A61M 15/0045* (2013.01); *A61M 15/0051* (2014.02); *A61M 15/0091* (2013.01); *A24F 40/20* (2020.01); *A61M 15/0016* (2014.02); *A61M 15/0043* (2014.02); *A61M 15/0068* (2014.02); *A61M 2016/0015* (2013.01); *A61M 2205/0266* (2013.01); *A61M 2205/0288* (2013.01); *A61M 2205/3331* (2013.01); *A61M 2205/3334* (2013.01); *A61M 2205/581* (2013.01); *A61M 2205/582* (2013.01); *A61M 2205/583* (2013.01); *A61M 2205/584* (2013.01); *A61M 2205/588* (2013.01); *A61M 2205/8206* (2013.01)

(58) Field of Classification Search
CPC .......... A24F 40/30; A24F 40/42; A24F 40/46; A61M 15/0003; A61M 15/0041; A61M 15/0043; A61M 15/0045; A61M 15/0046; A61M 15/0051; A61M 15/06; A61M 15/0068; A61M 11/04–048; A41F 47/002; A41F 47/008
See application file for complete search history.

(56) References Cited

U.S. PATENT DOCUMENTS

| | | | |
|---|---|---|---|
| 5,617,971 A | | 4/1997 | Eason et al. |
| 5,709,202 A | | 1/1998 | Lloyd et al. |
| 5,960,792 A | | 10/1999 | Lloyd et al. |
| 6,237,590 B1* | 5/2001 | Leedom | A61M 15/0051 128/203.15 |
| 6,520,179 B1* | 2/2003 | Von Schuckmann | A61M 15/0045 128/203.15 |
| 6,637,431 B2* | 10/2003 | Ekelius | A61M 15/0045 128/203.15 |
| 6,651,341 B1* | 11/2003 | Myrman | A61M 15/0045 128/203.15 |
| 6,907,880 B1* | 6/2005 | Heckenmuller | A61J 1/035 128/203.15 |
| 7,537,009 B2* | 5/2009 | Hale | A61K 31/519 128/203.16 |
| 8,360,057 B2 | 1/2013 | Ganem et al. | |
| 8,490,627 B2 | 7/2013 | Levin et al. | |
| 9,943,114 B2 | 4/2018 | Batista | |
| 2003/0037785 A1* | 2/2003 | Sonntag | A61M 11/06 128/203.12 |
| 2003/0178024 A1 | 9/2003 | Allan et al. | |
| 2004/0123864 A1* | 7/2004 | Hickey | A61M 15/0051 128/203.12 |
| 2005/0126562 A1* | 6/2005 | Rabinowitz | A61M 15/0051 128/200.23 |
| 2005/0268911 A1* | 12/2005 | Cross | A61M 11/002 128/204.17 |
| 2006/0016453 A1* | 1/2006 | Kim | A24F 40/42 131/194 |
| 2006/0032501 A1 | 2/2006 | Hale et al. | |
| 2007/0062548 A1 | 3/2007 | Horstmann et al. | |
| 2007/0221218 A1 | 9/2007 | Warden et al. | |
| 2008/0142006 A1* | 6/2008 | Bulbrook | A61M 15/0066 128/203.15 |
| 2008/0197045 A1 | 8/2008 | Metzger et al. | |
| 2009/0131918 A1 | 5/2009 | Budzellar et al. | |
| 2009/0293892 A1 | 12/2009 | Williams et al. | |
| 2010/0078022 A1 | 4/2010 | Striebig et al. | |
| 2010/0168710 A1* | 7/2010 | Braithwaite | A61M 15/0043 604/403 |
| 2011/0277752 A1 | 11/2011 | Chen et al. | |
| 2012/0048963 A1* | 3/2012 | Sharma | A61M 11/041 239/34 |
| 2012/0255548 A1 | 10/2012 | Denny et al. | |
| 2012/0298107 A1 | 11/2012 | Houzego et al. | |
| 2012/0325227 A1 | 12/2012 | Robinson et al. | |
| 2013/0276799 A1 | 10/2013 | Davidson et al. | |
| 2015/0223523 A1 | 8/2015 | McCullough | |
| 2016/0235122 A1* | 8/2016 | Krietzman | H05B 1/0225 |
| 2016/0345630 A1 | 12/2016 | Mironov et al. | |
| 2017/0164657 A1* | 6/2017 | Batista | H05B 3/34 |
| 2017/0360092 A1* | 12/2017 | Althorpe | A24F 40/44 |
| 2018/0271153 A1* | 9/2018 | John | A24F 40/42 |
| 2019/0314586 A1* | 10/2019 | Minskoff | A61M 11/02 |

FOREIGN PATENT DOCUMENTS

| | | | |
|---|---|---|---|
| CN | 1871044 | 11/2006 | |
| CN | 1889861 | 1/2007 | |
| CN | 101111226 | 1/2008 | |
| CN | 100571807 | 12/2009 | |
| CN | 103054196 | 4/2013 | |
| CN | 103271448 | 9/2013 | |
| CN | 203789150 | 8/2014 | |
| CN | 203952448 | 11/2014 | |
| CN | 104432509 | 3/2015 | |
| EP | 0129985 | 1/1985 | |
| EP | 0129985 A1 * | 1/1985 | ........ A61M 15/0045 |
| JP | 59-225070 | 12/1984 | |
| JP | 5-24044 | 3/1993 | |
| JP | 05-24044 | 3/1993 | |
| JP | 2010-516319 | 5/2010 | |
| JP | 4516970 | 5/2010 | |
| KR | 10-1319228 | 10/2013 | |
| RU | 2453344 | 6/2012 | |
| WO | WO 01/68169 | 9/2001 | |
| WO | WO-0172605 A1 * | 10/2001 | ........ A61M 15/0045 |
| WO | WO 2005/002654 | 1/2005 | |
| WO | WO 2014/032276 | 3/2014 | |
| WO | WO 2014/115324 | 7/2014 | |
| WO | WO 2016/001926 | 1/2016 | |
| WO | WO 2017/122196 | 7/2017 | |

OTHER PUBLICATIONS

Request for Examination and Search Report dated Mar. 26, 2020 From the Federal Government Institution, Federal Institute of Industrial Property of the Federal Service of Intellectual Property, Patents and Trademarks of the Russian Federation, FIPS Re. Application No. 2018129217 and Its Summary in English. (17 Pages).
Translation Dated Jul. 13, 2020 of Notification of Office Action and Search Report dated Jun. 23, 2020 From the Intellectual Property Office, Ministry of Economic Affairs of Taiwan, R.O.C. Re. Application No. 106100844. (4 Pages).
Notification of Office Action and Search Report dated Jun. 23, 2020 From the Intellectual Property Office of Taiwan, R.O.C. Re. Application No. 106100844. (5 Pages).
Notification of Office Action dated Aug. 20, 2018 From the Ministry of Science and Technology of the Republic of Vietnam, NOIP Re.

(56) References Cited

OTHER PUBLICATIONS

Application No. 1-2018-03482 and Its Summary in English. (3 Pages).
Supplementary European Search Report and the European Search Opinion dated Jul. 12, 2019 From the European Patent Office Re. Application No. 17738280.1. (10 Pages).
Corrected International Search Report and the Written Opinion dated Jun. 11, 2017 From the International Searching Authority Re. Application No. PCT/IL2017/050030. (23 Pages).
International Preliminary Report on Patentability dated Jul. 26, 2018 From the International Bureau of WIPO Re. Application No. PCT/IL2017/050030. (11 Pages).
International Search Report and the Written Opinion dated Apr. 30, 2017 From the International Searching Authority Re. Application No. PCT/IL2017/050030. (23 Pages).
Kahnert et al. "Menthol Capsules in Cigarettes Filters—Increasing the Attractiveness of A Harmful Product", Red Series, Tobacco Prevention and Tobacco Control, German Cancer Research Center, Heidelberg, DKFZ, 17: 1-31, 2012.
McPartland et al. "Are Cannabidiol and Delta9-Tetrahydrocannabivarin Negative Modulators of the Endocannabinoid System? A Systematic Review", British Journal of Pharmacology, 172(3): 737-753, Published Online Jan. 8, 2015.
Examination Report Under Sections 12 & 13 of the Patents Act, 1970 and the Patents Rules, 2003 dated Sep. 14, 2020 From the Government of India, Intellectual Property India, Patents, Designs, Trade Marks, Geographical Indications, The Patent Office Re. Application No. 201827029862. (5 Pages).
Notification of Office Action and Search Report dated Jun. 2, 2020 From the State Intellectual Property Office of the People's Republic of China Re. Application No. 201780016292.X and Its Summary in English. (11 Pages).
Translation Dated Sep. 22, 2019 of Request for Substantive Examination dated Aug. 29, 2019 From the National Institute of Intellectual Property, Ministry of Justice of Kazakhstan Re. Application No. 2018.0537.1. (4 Pages).
Patent Examination Report dated Feb. 9, 2021 From the Australian Government, IP Australia Re. Application No. 2017208165. (6 Pages).
Examination Report dated Jan. 22, 2021 From the Kementerian Hukum Dan Hak Asasi Manusia, Direktorat Jenderal Kekayaan Intelektual, Republik Indonesia [Ministry of Law and Human Rights, Directorate General of Intellectual Property Rights, Republic of Indonesia] Re. PID201805860 and Its Translation Into English. (6 Pages).
Notice of Reason for Rejection dated Dec. 8, 2020 From the Japan Patent Office Re. Application No. 2018-535846 and Its Translation Into English. (12 Pages).
Notification of Office Action and Search Report dated Apr. 15, 2021 From the State Intellectual Property Office of the People's Republic of China Re. Application No. 201780016292.X and an English Summary of the Office Action. (17 Pages).
Patent Examination Report dated Jun. 1, 2021 From the Australian Government, IP Australia Re. Application No. 2017208165. (5 Pages).
Notice of Reasons for Rejection dated Jul. 13, 2021 From the Japan Patent Office Re. Application No. 2018-535846 and Its Translation Into English. (6 Pages).
Notification of Office Action dated Jul. 26, 2021 From the State Intellectual Property Office of the People's Republic of China Re. Application No. 201780016292.X and its Translation into English. (23 Pages).
Request for Examination dated Sep. 20, 2021 From the (ROSPATENT), Federal Government Institution of Industrial Property of the Federal Service of Intellectual Property, Patents and Trademark of the Russian Federation Re. Application No. 2021111866. (10 Pages).
Subsequent Substantive Examination Report dated Sep. 23, 2021 From the Intellectual Propeerty Office of the Philipines Bureau of Patents Intellectual Property Center Re. Application No. 1-2018-501439. (5 Pages).
Notification of Office Action dated Oct. 26, 2021 From the Ministry of Science and Technology of the Republic of Vietnam, NOIP Re. Application No. 1-2018-03482 and Its Summary in English. (3 Pages).
Translation dated Nov. 4, 2021 of Request for Examination dated Sep. 2, 2021 From the (ROSPATENT), Federal Government Institution of Industrial Property of the Federal Service of Intellectual Property. Patents and Trademark of the Russian Federation Re. Application No. 2021111866. (5 Pages).

* cited by examiner

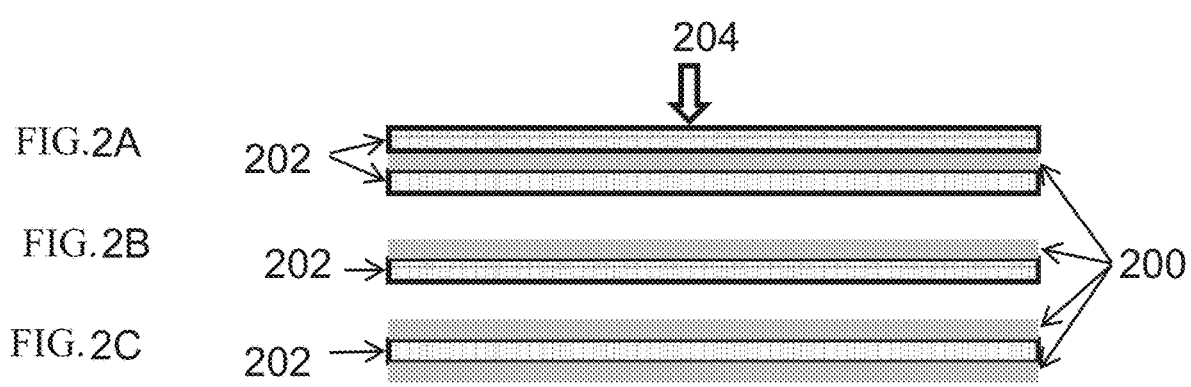

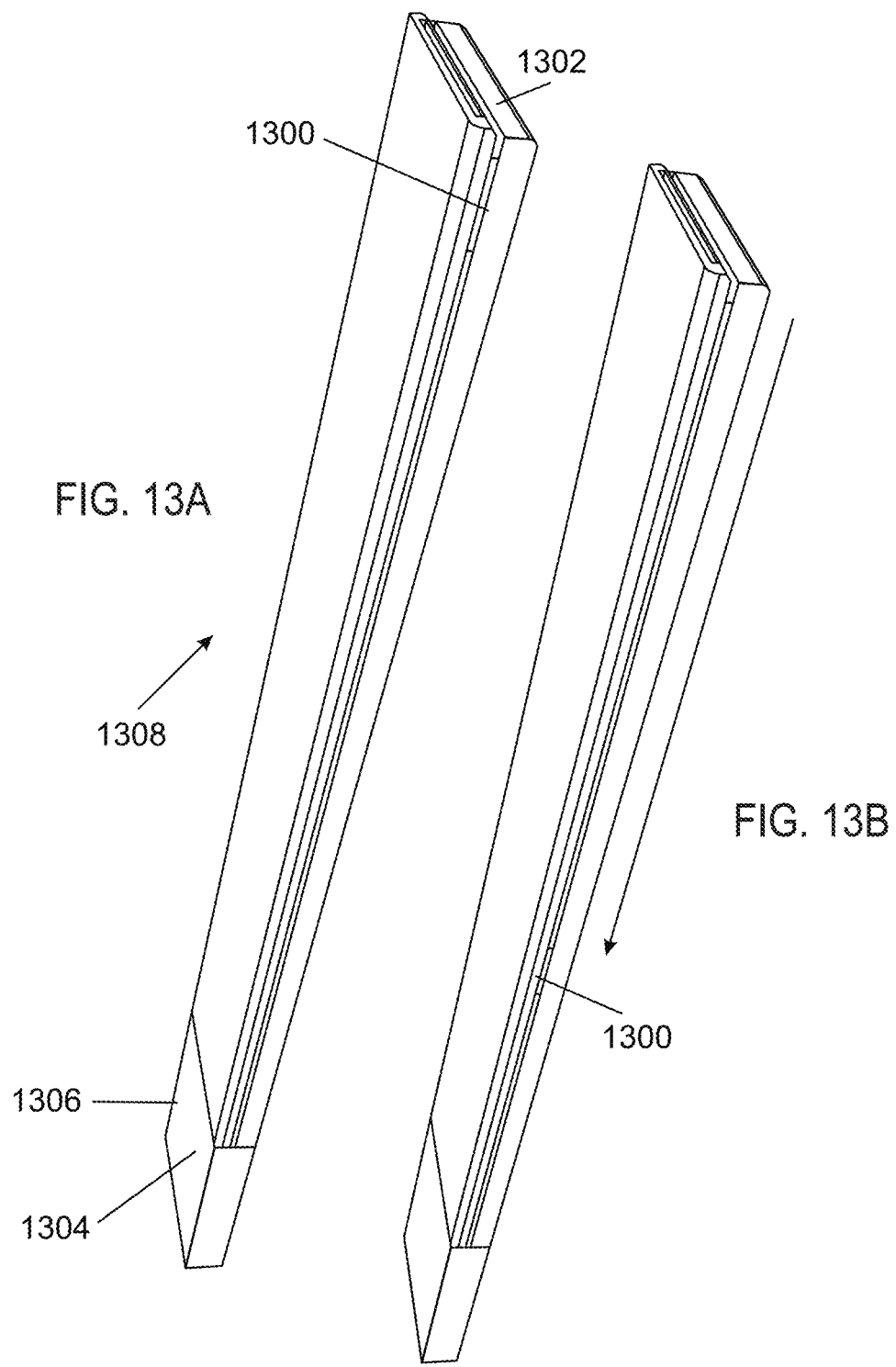

1400 — Selecting a source material section

1402 — Creating an airflow path between the selected source material section and an output to a user 1404 — Releasing at least one substance from the source material 1406 — Delivering the at least one substance via the airflow path to a user

FIG. 14

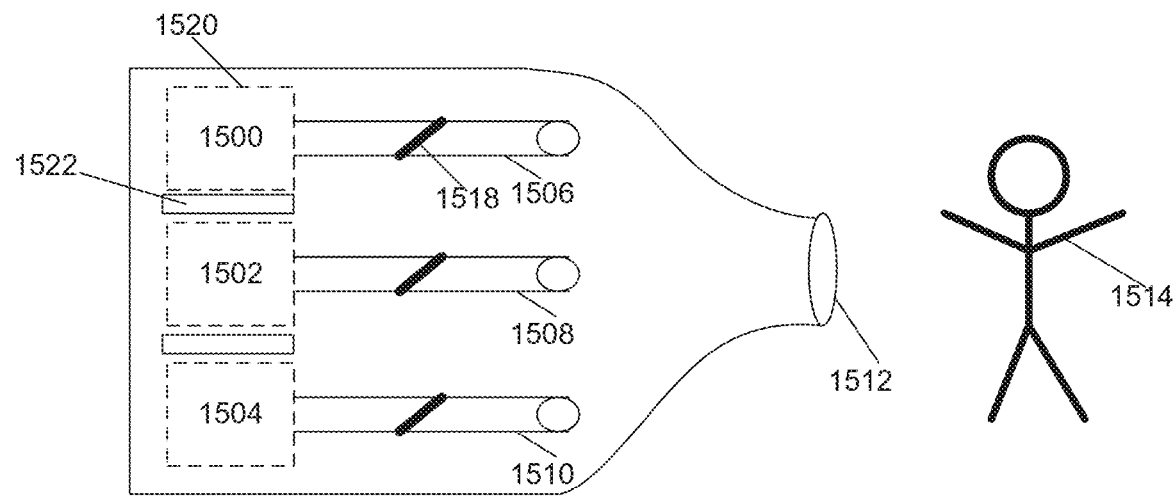
FIG.15A
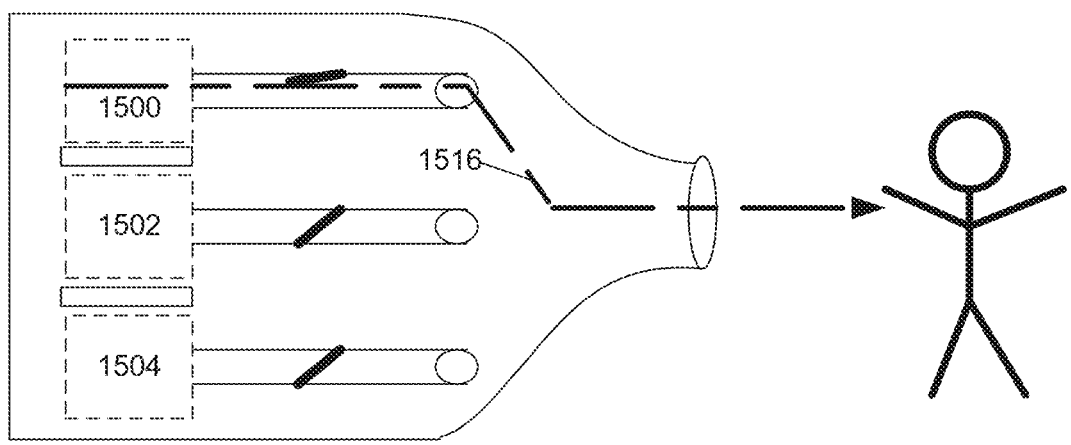
FIG.15B

2400

2402

PERSONAL VAPORIZING DEVICE WITH SLIDABLE CART

RELATED APPLICATIONS

This application is a National Phase of PCT Patent Application No. PCT/IL2017/050030 having International filing date of Jan. 11, 2017, which claims the benefit of priority under 35 USC § 119(e) of U.S. Provisional Patent Application No. 62/277,060 filed on Jan. 11, 2016. The contents of the above applications are all incorporated by reference as if fully set forth herein in their entirety.

FIELD AND BACKGROUND OF THE INVENTION

The present invention, in some embodiments thereof, relates to delivering an active substance through inhalation and, more particularly, but not exclusively, to delivery of at least one active substance through a plurality of delivery events in which a controlled portion of source material is heated independently of other portions of the source material.

SUMMARY OF THE INVENTION

According to an aspect of some embodiments of the invention, there is provided a device configured for releasing at least one substance from source material, comprising: a housing; a plurality of source material sections positioned at fixed locations with respect to the housing; a plurality of airflow paths, each airflow path associated with at least one of the source materials sections; each airflow path associated with at least one blocking element which prevents flow of air through the path; and an actuator operably coupled to the blocking element, the actuator configured for unblocking the airflow path of at least one selected source material section to allow flow of air to and through source material within the section. In some embodiments, each source material section is associated with a dedicated heating element. In some embodiments, the heating element is configured to heat the source material so as to release the at least one active substance. In some embodiments, the actuator is configured for electrically coupling the heating element associated with the selected source material section. In some embodiments, a geometry of the device is selected so that air that flows through a selected source material section does not affect non-selected sections. In some embodiments, the device comprises a controller programmed to coordinate between the flow of air through the at least one source material section and activating of a heating element associated with the at least one source material section. In some embodiments, the device is configured to allow usage of source material sections in an order that does not depend on a spatial arrangement of the source material sections. In some embodiments, the blocking element comprises a cover of the source material section. In some embodiments, the actuator is configured for shifting the cover to a position in which air flow is allowed to and through source material of the section. In some embodiments, the actuator is configured for shifting the cover using magnetic attraction. In some embodiments, the device comprises a mouthpiece and at least one conduit for directing the flow of air through the heated source material section towards the mouthpiece. In some embodiments, the plurality of source material sections are arranged linearly along a long axis, and the actuator is slidable along the long axis. In some embodiments, the device is an inhaler configured to deliver the at least one active substance to a user via inhalation. In some embodiments, the device is configured to deliver the at least one active substance over a plurality of delivery events, wherein in each delivery event a controlled dose of the active substance is delivered to the user. In some embodiments, the device is a cartridge for use with an inhaler device. In some embodiments, the source material sections are separated from each other by an air-sealed barrier. In some embodiments, the device comprises at least one shared conduit extending along the source material sections. In some embodiments, the source material within at least one of the sections comprises between 1-10% nicotine. In some embodiments, a layer of source material within each section is no more than 1 mm thick. In some embodiments, different source material sections comprise different source materials. In some embodiments, the source material sections comprise different active substances or compositions thereof. In some embodiments, the source material sections are arrayed linearly with respect to each other. In some embodiments, an amount of active substance decreases along a long axis defined by the array. In some embodiments, an amount of active substance increases along a long axis defined by the array.

According to an aspect of some embodiments of the invention, there is provided a device configured for delivering, through inhalation, at least one active substance released from a source material, the device comprising: one or more source material sections in which the source material is protected by a sealant impermeable to air, the sealant comprising a control region providing for opening at least one opening through the sealant; a flow arrangement configured to direct a flow of air to a user of the device through one or more of the sections; and an actuator aligned with the control region of the sealant and with the flow arrangement for selectively opening the at least one opening through the sealant, at the sections, to allow air to flow through the source material. In some embodiments, the control region of the sealant is temperature sensitive, and the actuator comprises a heating element configured to heat the sealant to open the at least one opening. In some embodiments, the actuator comprises an airflow element configured to apply pressure generated by inhalation to the control region of the sealant to open the at least one opening. In some embodiments, the actuator comprises a set of electrodes configured to apply electricity to the control region of the sealant to open the at least one opening. In some embodiments, the actuator comprises a knife or punch configured to perforate the control region of the sealant to open the at least one opening. In some embodiments, the device comprises a power source. In some embodiments, the actuator is movable with respect to the one or more source material sections. In some embodiments, the actuator is configured to slide, roll, and/or be dragged relative to the source material sections. In some embodiments, the device comprises a progress indicator configured to indicate one or more of: an amount of source material sections used, an amount of source material sections remaining, an amount of source material remaining in a section, that all source material sections have been consumed and that a given portion of the source material sections has been used. In some embodiments, the device comprises an elongated configuration and the progress indicator is configured to move along at least a portion of a length of the device. In some embodiments, a longitudinal position of the progress indicator corresponds with a serial position of a source material section currently being used. In some embodiments, the progress indicator is configured to move upon loading of a new source material section, the loading performed automatically and/or manually by a user. In some embodiments, the progress indicator comprises one or more of a light indication and a color indication. In some embodiments, the source material sections are contained a cartridge, the cartridge received within the inhaler. In some embodiments, a plurality of source material cartridges are received in the inhaler.

According to an aspect of some embodiments of the invention, there is provided a source material cartridge configured for use with an inhaler device, comprising: one or more sections comprising source material; the source material comprising at least one active substance releasable by vaporization; the source material arranged to allow a flow of air there through; wherein the source material is protected by a sealant impermeable to air, the sealant comprising a control region which is mechanically sensitive and/or temperature sensitive, providing for opening at least one opening through the sealant during use of the inhaler device to allow air to flow through source material of one or more selected sections to deliver the at least one active substance to a user. In some embodiments, the sealant is configured to open the at least one opening as a result of being heated. In some embodiments, the sealant is configured to heat the source material. In some embodiments, the cartridge comprises only one source material section formed as an elongate pallet, and wherein an amount of active substance released from at least a portion of the pallet is set by controlling airflow to the portion. In some embodiments, the cartridge comprises a plurality of source material sections that are separated from each other by at least one of a thermal insulation and an electrical insulation. In some embodiments, when the cartridge comprises one or more conduits through which drug imbued air flows to be delivered to a user, so that when the cartridge is received within an inhaler, the drug imbued air flows only through the cartridge, thereby eliminating residues in the inhaler.

According to an aspect of some embodiments of the invention, there is provided a device configured for delivering to a user at least one substance released from a source material, comprising: frame comprising one or more source material sections; a mouthpiece component; and conduit configured for conducting a substance through at least one of the sections to a user, the conduit extending between at least one of the source material sections and the mouthpiece component. In some embodiments, the frame is shaped and sized to engage an inhaler device. In some embodiments, the at least one source material section and the conduit are sealed such that the airflow is allowed to flow only through the at least one section and the conduit.

According to an aspect of some embodiments of the invention, there is provided a device configured for delivering, through inhalation, at least one active substance released from a source material, comprising: a substrate comprising a plurality of slots, each slot containing source material, each slot associated with a dedicated airflow path; moveable actuator positionable to unblock the airflow path once aligned with an opening of the airflow path to provide for flow of air through source material of at least one selected slot. In some embodiments, the device further comprises a heating element associated with each of the source material slots, and circuitry for electrically coupling the heating element to a power source upon movement of the actuator. In some embodiments, the actuator is a rotatable actuator. In some embodiments, the substrate comprises a PCB.

According to an aspect of some embodiments of the invention, there is provided an inhaler device configured for delivering to a user at least one substance released from a source material, comprising: one or more source material sections arranged along a longitudinal axis; a slidable actuator configured to slide, automatically or manually, along the longitudinal axis to actuate release of the at least one substance from at least one source material section. In some embodiments, the slidable actuator is configured for unblocking at least one airflow path associated with at least one source material section. In some embodiments, the slidable actuator is configured for activating a heating element associated with the at least one source material section.

According to an aspect of some embodiments of the invention, there is provided a source material cartridge comprising: one or more sealed sections comprising source material; a carrier conduit for conducting airflow to at least one unsealed source material section; and a bypass conduit which does not pass through the source material sections; wherein flow through the bypass conduit is regulated in response to flow through the carrier conduit.

According to an aspect of some embodiments there is provided an inhaler device configured for delivering to a user at least one substance released from a source material, said device configured to receive a plurality of cartridges each comprising a plurality of source material sections, said device comprising a controller configured to address at least one source material section of at least one of said plurality of cartridges according to a predefined regimen and to actuate delivery of at least one substance released from said at least one source material section to a user. In some embodiments, once the plurality of cartridges are received in the inhaler, the cartridges remain static and are not moved with respect to each other, even during use. In some embodiments, the plurality of source material sections of a single cartridge remain static and are not moved with respect to each other, even during use. In some embodiments, the controller is configured to address the at least one source material section upon demand of the user. In some embodiments, the plurality of cartridges contain different source materials or compositions thereof. In some embodiments, the plurality of source material sections of a single cartridge contain different source materials or compositions thereof.

According to an aspect of some embodiments of the invention there is provided a device configured for delivering, through inhalation, at least one active substance released from a source material by vaporization; the device comprising: a receptacle configured to receive at least one cartridge, the cartridge comprising one or more source material sections in which the source material is protected by a sealant impermeable to air, the sealant comprising a control region providing for opening at least one opening through the sealant; a flow arrangement configured to direct a flow of air through one or more selected sections and to a user of the device, when the cartridge is received within the receptacle; and an actuator aligned with the control region of the sealant and with the flow arrangement for opening the at least one opening through the sealant, at the selected sections, to allow air to flow through the source material. In some embodiments, the control region of the sealant is temperature sensitive, and the actuator comprises a heating element configured to heat the sealant to open the at least one opening. In some embodiments, the heating element is configured to heat the source material so as to vaporize the at least one active substance. In some embodiments, the actuator comprises an airflow element configured to apply pressure generated by inhalation to the control region of the sealant to open the at least one opening. In some embodiments, the actuator comprises a set of electrodes configured to apply electricity to the control region of the sealant to open the at least one opening. In some embodiments, the actuator comprises a knife or punch configured to perforate the control region of the sealant to open the at least one opening. In some embodiments, the device comprises a power source. In some embodiments, the actuator is movable with respect to the one or more source material sections of the cartridge. In some embodiments, the actuator is configured to slide, roll, and/or be dragged relative to the source material sections. In some embodiments, the device is configured to deliver the at least one active substance over a plurality of delivery events, wherein in each delivery event a controlled dose of the active substance is delivered to the user. In some embodiments, the device comprises a progress indicator configured to indicate one or more of: an amount of source material used, an amount of source material remaining, that all source material has been consumed and that a given portion of the source material has been used. In some embodiments, the device comprises an elongated configuration and the progress indicator is configured to move along at least a portion of a length of the device. In some embodiments, a longitudinal position of the progress indicator corresponds with a serial position of a source material section currently being used. In some embodiments, the progress indicator is configured to move upon loading of a new source material section, the loading performed automatically and/or manually by a user. In some embodiments, the progress indicator comprises one or more of a light indication and a color indication.

According to an aspect of some embodiments of the invention there is provided a source material cartridge configured for use with a vaporizing device, comprising one or more sections comprising source material, the sections separated from each other by a thermal and/or electrical insulation; the source material comprising at least one active substance releasable by vaporization; the source material arranged to allow a flow of air there through; wherein the source material, in each of the sections, is protected by a sealant impermeable to air, the sealant comprising a control region which is mechanically sensitive and/or temperature sensitive, providing for opening at least one opening through the sealant during use of the vaporizing device to allow air to flow through source material of one or more selected sections to deliver the at least one active substance to a user of the vaporizing device. In some embodiments, the sealant is configured to be heated so as to open the at least one opening. In some embodiments, the sealant is configured to heat the source material. In some embodiments, the sealant is a foil comprising an electrically resistive substance, the sealant is an electrically conductive foil configured to heat the source material when an electrical current is applied to the foil. In some embodiments, the sealant comprises a shape memory material, such as but not limited to shape memory polymers that deform in response to heat, thereby allowing access to the source material. In some embodiments, one or more springs and/or other mechanisms are used for returning the sealant to a closed position when the heating process is over. Additionally or alternatively, the sealant comprises shape memory material having a 2-way shape memory effect. In some embodiments the sealant comprises and/or is connected to a shape memory material such as but not limited to shape memory alloys as Nitinol, Copper-Aluminum-Zinc or others. In some embodiments, the sealant comprises stainless steel. In some embodiments, the sealant is configured to be resealed after the source material is used. In some embodiments, the source material sections are arranged to be unsealed in a serial manner. In some embodiments, a source material section comprises source material at an amount sufficient to deliver a single dose of the active substance when vaporized. In some embodiments, the source material comprises tobacco. In some embodiments, the source material comprises *cannabis*.

According to an aspect of some embodiments of the invention there is provided a method of delivering, through inhalation, at least one active substance released from a source material by vaporization of the source material, comprising providing a source material sealed by a sealant impermeable to air; opening at least one opening in the sealant by at least one of heating the sealant and applying a mechanical force to the sealant to allow air to pass through the source material; directing a flow of air through the source material while simultaneously heating the source material; delivering vapors of the active substance to the user through inhalation. In some embodiments, the method further comprises aligning an actuator configured to open the at least one opening in the sealant with the sealant and the flow of air. In some embodiments, at least one of opening, directing a flow of air and heating is initiated in response to inhalation of the user. In some embodiments, directing comprises dynamically moving across the source material an element structured to direct airflow to the source material.

According to an aspect of some embodiments of the invention there is provided a source material cartridge for use with a vaporizing device, comprising:
a cartridge comprising one or more source material sections; a mouthpiece component; and
a conduit configured for conducting a flow of vapor, the conduit extending between the cartridge and the mouthpiece component.

According to an aspect of some embodiments of the invention there is provided a source material cartridge for use with a vaporizing device, comprising: a cartridge comprising one or more source material sections; and a conduit configured for conducting a flow of vapor, the conduit configured to extend when in use with the vaporizing device between the cartridge and a mouthpiece of the device.

According to an aspect of some embodiments of the invention there is provided a device configured for delivering, through inhalation, at least one active substance released from a source material by vaporization, comprising: a receptacle configured to receive at least one cartridge comprising a plurality of source material sections; a heating element configured to separately heat each of the source material sections; and a flow arrangement configured to be moved along the cartridge to selectively direct a flow of air through the one or more of the source material sections when the sections are heated, to deliver air imbued with the active substance to a user through inhalation.

According to an aspect of some embodiments there is provided a method of delivering to a user at least one substance released from a source material, comprising: selecting at least one source material section out of a plurality of source material sections; creating an airflow path between the selected source material section and an output to a user such that each source material section is associated with at least one airflow path. In some embodiments, creating an airflow path comprises modifying a state of at least one airflow path associated with at least one selected source material section from a state in which flow of air is not permitted through the path to a state in which at least some flow of air is permitted through the path. In some embodiments, creating an airflow path comprises unblocking at least one airflow path. In some embodiments, modifying a state of an airflow path is reversible. In some embodiments, the method further comprising releasing, via the flow of air, at least one substance from the source material; and delivering the flow of air, after it has been imbued with the substance to a mouth of a user. In some embodiments, releasing at least one substance comprises electrically coupling a heating element associated with the at least one source material section so as to heat source material within that section. In some embodiments, a timing of electrically coupling is selected in accordance with a timing of creating of an airflow path. In some embodiments, a subset of at least two source material sections out of the plurality of source material sections is selected.

According to an aspect of some embodiments of the invention, there is provided a source material cartridge configured for use with an inhaler device, comprising: one or more sections comprising source material, the sections separated from each other by at least one of a thermal insulation and an electrical insulation; the source material comprising at least one active substance releasable by vaporization; the source material arranged to allow a flow of air there through; and wherein the source material, in each of the sections, is protected by a sealant impermeable to air, the sealant comprising a control region which is mechanically sensitive and/or temperature sensitive, providing for opening at least one opening through the sealant during use of the inhaler device to allow air to flow through source material of one or more selected sections to deliver the at least one active substance to a user. In some embodiments, the sealant is configured to open the at least one opening as a result of being heated. In some embodiments, the sealant is configured to heat the source material. In some embodiments, the sealant is a foil comprising an electrically resistive substance, the foil configured to heat the source material when an electrical current is applied to the foil. In some embodiments, the sealant comprises a shape memory material. In some embodiments, the sealant comprises stainless steel. In some embodiments, the sealant is configured to be resealed after the source material is used.

In some embodiments, the sections of source material are arranged to be unsealed in a serial manner. In some embodiments, the source material comprises bioactive botanicals. In some embodiments, the source material comprises tobacco. In some embodiments, the source material comprises *cannabis*.

According to an aspect of some embodiments of the invention, there is provided a method of delivering, through inhalation, at least one active substance released from a source material, comprising: providing a source material sealed by a sealant impermeable to air; opening at least one opening in the sealant by at least one of heating the sealant and applying a mechanical force to the sealant to allow air to pass through the source material; directing a flow of air through the source material while simultaneously heating the source material; and delivering vapors of the active substance to the user through inhalation. In some embodiments, the method further comprises aligning an actuator configured to open the at least one opening in the sealant with the sealant and the flow of air. In some embodiments, at least one of opening, directing a flow of air and heating is initiated in response to inhalation of the user. In some embodiments, directing comprises dynamically moving across the source material an element structured to direct airflow to the source material.

According to an aspect of some embodiments of the invention, there is provided a device configured for delivering to a user at least one substance released from a source material, comprising: at least one source material section at least partially sealed by a fluid that changes its viscosity in response to a temperature change; an airflow path, associated with at least one of the source materials sections; a heating element configured to heat the fluid; and one or more chambers into which the fluid is allowed to flow when its viscosity is reduced in response to heating, thereby exposing at least a portion of the source material to airflow. In some embodiments, the fluid comprises silicone oil.

According to an aspect of some embodiments of the invention, there is provided a device configured for delivering, through inhalation, at least one active substance released from a source material, the device comprising: a plurality of receptacles configured to receive a plurality of cartridges respectively, each cartridge comprising one or more source material sections; a flow arrangement configured to direct a flow of air through one or more sections and to a user of the device, when the cartridges are received within the receptacles; and an actuator configured for selectively accessing one or more source material sections according to their content. In some embodiments, a cartridge selected out of the plurality of cartridges comprises source material sections that differ in at least one of an amount of active substance, a type of active substance, a type of source material or compositions thereof. In some embodiments, the plurality of cartridges differ from each other in at least one of an amount of active substance, a type of active substance, a type of source material or compositions thereof. In some embodiments, the device comprises a plurality of source material sections.

According to an aspect of some embodiments of the invention, there is provided a device configured for delivering, through inhalation, at least one active substance released from a source material by vaporization, comprising: a receptacle configured to receive at least one cartridge comprising a plurality of source material sections; a heating element configured to separately heat each of the source material sections; and a flow arrangement configured to be moved along the cartridge to selectively direct a flow of air through the one or more of the source material sections when the sections are heated, to deliver air imbued with the active substance to a user through inhalation.

Unless otherwise defined, all technical and/or scientific terms used herein have the same meaning as commonly understood by one of ordinary skill in the art to which the invention pertains. The terms "example", "exemplary" and "such as" are used herein to mean "serving as an example, instance or illustration". Any embodiment described as an "example" or "exemplary" is not necessarily to be construed as preferred or advantageous over other embodiments and/or to exclude the incorporation of features from other embodiments. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

BRIEF DESCRIPTION OF THE SEVERAL VIEWS OF THE DRAWINGS

Some embodiments of the invention are herein described, by way of example only, with reference to the accompanying drawings. With specific reference now to the drawings in detail, it is stressed that the particulars shown are by way of example and for purposes of illustrative discussion of embodiments of the invention. In this regard, the description taken with the drawings makes apparent to those skilled in the art how embodiments of the invention may be practiced.

In the drawings:

FIGS. 2A-C illustrate three configurations of a coupling between source material and a heating element, according to some embodiments of the invention;

FIGS. 13A-B illustrate a device for example as shown in FIGS. 12A-E, comprising a use progress indicator, according to some embodiments of the invention;

FIG. 14 is a flowchart of a general method of delivering to a user at least one substance released from a source material, according to some embodiments of the invention;

FIGS. 15A-B schematically illustrate selectively unblocking an airflow path associated with a selected source material section, according to some embodiments of the invention;

DESCRIPTION OF SPECIFIC EMBODIMENTS OF THE INVENTION

Figure 1A:
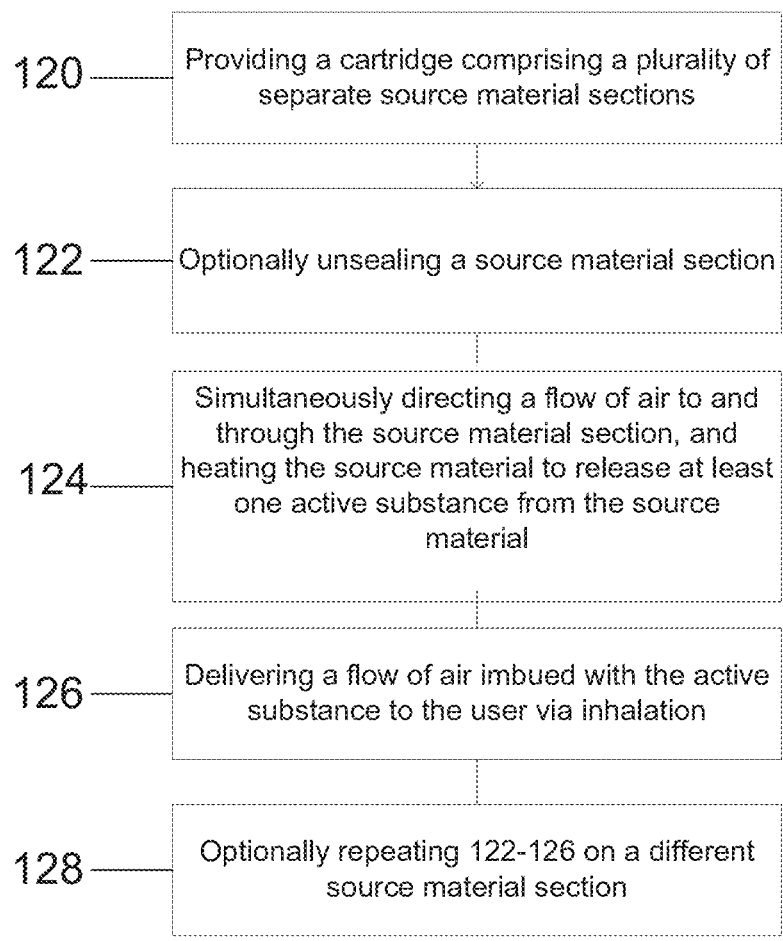
FIG. 1A is a flowchart of a general method of operation of a device configured for delivering at least one active substance to a user through inhalation, according to some embodiments of the invention.

The present invention, in some embodiments thereof, relates to delivering at least one active substance through inhalation and, more particularly, but not exclusively, to delivery of at least one active substance through a plurality of delivery events in which a controlled portion of source material is heated independently of other portions of the source material.

An aspect of some embodiments relates to a device configured for heating at least one source material section selected from a plurality of source material sections independently of the non-selected active substance sections. In some embodiments, the device is configured to simultaneously heat the source material section and to allow airflow through the source material section so as to vaporize the active substance by heating.

In some embodiments, the source material is arranged in a plurality of sections. Optionally, the sections are thermally and/or electrically isolated from each other. Alternatively, the source material is arranged in a continuous single section.

Optionally, only a portion of the continuous section is heated at a given time. Optionally, a plurality of sections are heated simultaneously to deliver a combination of active substances.

In some embodiments, the source material is protected by a sealant. In some embodiments, the sealant is a structure impermeable to air and/or material. In an example, the sealant is a foil, for example a stainless steel foil. In some embodiments, the sealant comprises a control region through which one or more openings can be formed to allow air to flow through the sealant and through the source material.

Optionally, the openings are formed during use.

In some embodiments, the control region of the sealant comprises mechanically sensitive regions, and at least one opening can be formed in the sealant by applying of force. In an example, force in the form of air pressure generated by inhalation of the user is applied to the control region. In another example, a knife or punch are used to penetrate the sealant. Additionally or alternatively, the control region of the sealant comprises temperature sensitive regions, and at least one opening can be formed in the sealant by heating the sealant. Additionally or alternatively, an electrical current is applied to the sealant to form the at least one opening through.

Additionally or alternatively, the control region of the sealant comprises chemically sensitive regions.

In some embodiments, the sealant is configured to heat the source material so as to vaporize the at least one active substance. For example, when the sealant is electrically resistive, it may heat the source material when an electrical current is applied to it. Optionally, the sealant comprises a shape memory material which is configured to deform when heated to allow for air to pass through the sealant.

In some embodiments heating of the sealant is performed using an additional component such as magnetic induction of the sealant or of other components; thermal radiation transfer to the sealant or to other components; convection of heat from a heat source and/or other mechanisms suitable to heat the sealant. Optionally the sealant comprises a heat sensitive material that dissolves when heated to allow airflow through.

In some embodiments, a heating element comprises and/or is connected to electrodes through which current is applied to heat a temperature sensitive region, for example a region of the sealant. In some embodiments a heating element comprises a heatable plate, a hot air source (e.g. generator), a thermal emitter and/or any other suitable heat source.

In some embodiments, the openings formed in the sealant allow airflow in a single direction, thereby preventing back flow of the active substance. In some embodiments, openings in the sealant are resealed, for example after the source material is used.

Alternatively, the source material is enclosed within and/or otherwise in contact with an element which is air permeable in advance, for example a mesh or a perforated foil.

In some embodiments, the device comprises an airflow element configured to direct a flow of air through the source material section. Optionally, the airflow element is dynamically moved (e.g. by sliding, being dragged on, rolling) across the source material. In some embodiments, the airflow element comprises a set of electrodes for applying a current to a heating element and/or to a sealant of a targeted source material section so as to heat the source material and/or to perforate the sealant.

In some embodiments, a flow of air is heated before passing through the source material. Optionally, in embodiments in which the source material is enclosed within and/or covered by a sealant which is not air permeable, the heated airflow forms at least one opening through the sealant to allow air to pass through at least a portion of the source material.

In some embodiments, air drawn into the device in response to suction generated by inhalation of a user is directed to pass through a section of source material. In some embodiments, the air passes through a thickness of the source material, for example entering through a first surface of the material and exiting through a second, optionally opposite surface of the source material. Additionally or alternatively, air enters and exits the source material on the same side.

In some embodiments, heating is applied to extract and/or otherwise release the at least one active substance from the source material and/or to unseal the sealant, simultaneously to the passing of air through. The active substance imbued air exiting the source material section is then delivered to the user through inhalation.

In some embodiments, a heating element and/or an airflow element and/or an electricity applying element (e.g. electrodes) are aligned with respect to each other and with respect to one or more selected source material sections. Optionally, one or more of the heating element and/or airflow element and/or electricity applying element function as an actuator for opening one or more openings (e.g. a hole, a perforation, a slit) through the sealant, when aligned with respect to a control region of the sealant, to allow air to flow there through. In some embodiments, the alignment is temporary. In some embodiments, alignment of two or more of: a heating element and/or an airflow element and/or an electricity applying element with respect to each other is controlled by software presets. Optionally, a controller of the inhaler device is configured to control activation and/or position of: a heating element and/or an airflow element and/or an electricity applying element so as to carry out alignment.

Optionally, the alignment is obtained before and/or during use of the selected section(s). Optionally, the alignment is maintained until the source material of a selected section is consumed, and/or until loading of another source material section.

In some embodiments, an amount of source material in each section comprises a single dose of the active substance. In an embodiment, the device comprises a single section of source material. Optionally, an amount of source material in the single section comprises a single dose of the active substance. In some embodiments, an amount of source material in a single section is sufficient for a plurality of delivery events, which may involve multiple inhalations of the user. Optionally, the device is configured so that at each delivery event a lesser amount of active substance is delivered to the user relative to the amount delivered in a previous delivery event.

In some embodiments, the device comprises a loading mechanism, (for example in which an airflow element is advanced from a used source material section to a non-used section). Optionally, the loading mechanism is user controlled, allowing a user to cock the device to proceed to a non-used source material section at their will. A potential advantage of a user-controlled loading mechanism may include a psychological effect on the user in which the user anticipates maximum potency in the newly loaded dose.

Additionally or alternatively, the loading mechanism is automatically operated.

In some embodiments, the source material comprises or consists of tobacco. In some embodiments, the source material comprises or consists of *cannabis*.

Additionally or alternatively, the source material comprises or consists of other botanicals.

In some embodiments, the source material is the only supply of material used by the device or comprises at least 90% or at least 95% by weight of the supply of material used by the device. Optionally, the imbued airflow delivered by the device to user comprises only of one or more active substances extracted from the source material alone. Optionally, any active substances in the imbued airflow delivered by the device to user are limited to scent and/or flavor molecules.

As used herein, the term "active substance" means a heat-vaporizing substance that comprises a compound having at least one medicinal and/or somatic and/or psychoactive effect. Optionally the compound includes one or more cannabinoids, for example Tetrahydrocannabinol (THC), Cannabidiol (CBD) and Cannabinol (CBN). Optionally, the compound includes one or more alkaloids, for example nicotine and/or 1,2,3,4-Tetrahydroisoquinolines, Anabasine, Anatabine, Cotinine, Myosmine, Nicotrine, Norcotinine, and/or Nornicotine. In some embodiments, the heat-vaporizing substance vaporizes at a temperature requiring a substantial exogenous heat input to reach a temperature above ambient temperature. For example, the substance vaporizes at a temperature within the range from 80° C.-250° C., or within another range having the same, higher, lower, intermediate and/or intermediate bounds, for example between 160-230° C. In some embodiments, the substance vaporizes at a temperature above 80° C., 100° C., 150° C., 200° C., 230° C., or another higher, lower, or intermediate temperature. In some embodiments, the time to reach a volatilizing temperature is, for example, about in a range between about 100 msec-5 sec, 100-750 msec, 150-300 msec, or another range having the same, larger, smaller, and/or intermediate bounds. In particular, the time is, for example, 250 msec, 500 msec, 1000 msec, or another greater, smaller, or intermediate value.

In some embodiments, the sealant covers all of the source material, such that all material is protected by the sealant and no material is free.

In some embodiments, the device is shaped essentially as a conventional cigarette, comprising for example a cylindrical configuration. Alternatively, the device is shaped as a substantially flat strip and/or comprises any other configuration suitable for delivering the at least one active substance through inhalation.

An aspect of some embodiments relates to creating an airflow path between one or more selected source material sections and an output to a user. In some embodiments, creating an airflow path comprises modifying a state of an airflow path (e.g. a conduit) associated with the one or more selected sections from a state in which flow of air is not permitted through, to a state in which flow of air is permitted through. In some embodiments, a blocking element is eliminated, shifted, removed and/or otherwise moved away from the path so as to allow for airflow through. When the path is unblocked, air is allowed to flow to and optionally through source material of the selected one or more sections. In some embodiments, the source material is heated concomitantly (simultaneously and/or shortly before and/or after) creating of the airflow path, to extract at least one active substance from the source material and deliver the active substance via the flow of air to a user. In some embodiments heating is triggered by sensing a parameter of airflow (for example pressure).

In some embodiments, the source material sections remain stationary with respect to one another. In some embodiments, a source material section remains stationary with respect to one or more of: a heating element associated with the section and configured for heating the source material; a conduit associated with the section and extending between the section and an output to user; a housing of the source material cartridge.

Some embodiments comprise an actuator configured for creating the airflow path. For example, in some embodiments, the actuator is configured for moving a blocking element (e.g. opening a cover of a source material section), aligning an opening of a conduit with an airflow exit, and/or otherwise modifying a path so that air is allowed to flow to the source material. In some embodiments, the actuator is configured for activating heating of the source material, for example by closing an electrical circuit so that a heating element associated with the selected source material section is activated. In some embodiments, once the circuit is closed, heating is triggered or increased in response to sensing airflow, for example in response to inhalation of the user.

In some embodiments, the actuator is manually operated. Additionally or alternatively, the actuator is automatically operated, for example being controlled by a controller of the device.

In some embodiments, operations such as selecting of one or more source material sections and/or activating of heating of the source material and/or modifying (e.g. opening) of an airflow path are mechanically actuated. Additionally or alternatively, operations for example as described are electronically controlled and/or actuated, for example using a solid state switch such as a transistor.

An aspect of some embodiments relates to use of a fluid that varies in viscosity as a sealant of source material. In some embodiments, a fluid that changes its viscosity in response to a change in temperature, for example Silicone oil, covers at least a portion of the source material. Optionally, the fluid is disposed on a mesh or other frame containing the source material. In some embodiments, when heating is applied to the mesh, a viscosity of the fluid decreases and the fluid flows away (in an example, the fluid flows away from the mesh and is then collected within one or more side chambers), thereby exposing at least a part of the source material to flow of air. Optionally, when heating is terminated, the fluid cools down and spontaneously returns to cover the exposed area again. In some embodiments, changes in surface tension and/or wetting properties of the fluid cause motion of the fluid, for example causing the fluid to flow back to its original position. Optionally, capillary action of the fluid enables it to flow through small diameter channels extending to and/or from the mesh.

An aspect of some embodiments relates to a device configured to receive a plurality of cartridges, each including one or more source material sections, the device being optionally configured to use the sections according to their content. In some embodiments, a plurality of source material sections are selected for use according to a predefined regimen and/or on demand according to their content and/or location. In some embodiments, source material sections of a cartridge and/or different cartridges differ from each other in at least one of: type(s) of source material, type(s) of active substance(s), amount(s) of source material(s), and amount(s) of active substance(s).

The term "substrate" as used herein in accordance with some embodiments may include a bar, a solid structure, a surface having a thickness, and/or other element comprising holes or slots in which source material can be contained.

The term "frame" as used herein in accordance with some embodiments may include a structure defining sizable empty spaces, a casing, a cage, and/or any other element defining spaces or sections in which source material can be contained.

Both terms "substrate" and "frame" as used herein are intended to cover a structure suitable for containing source material in one or more defined spaces.

It is noted that the at least one active substance delivered to the user is not limited to the form of vapors and may additionally or alternatively be provided as aerosol.

Before explaining at least one embodiment of the invention in detail, it is to be understood that the invention is not necessarily limited in its application to the details of construction and the arrangement of the components and/or methods set forth in the following description and/or illustrated in the drawings and/or the Examples. The invention is capable of other embodiments or of being practiced or carried out in various ways.

Referring now to the drawings, FIG. 1A is a flowchart of a method of operation of a vaporizing device configured for delivering at least one active substance to a user through inhalation, according to some embodiments.

In some embodiments, the device comprises or, in some embodiments, is configured to receive a cartridge comprising a plurality of separate source materials sections (120). In some embodiments, the device comprises a single source material section.

In some embodiments, the source material is covered by a sealant, for example contacting one or more surfaces of the source material. Optionally, the sealant is an artificially manufactured sealant, for example an electrically resistive material that is optionally in the form of a foil, such as a metal foil.

In some embodiments, the sealant prevents air and/or moisture from entering the source material. Optionally, the sealant prevents evaporation and/or oxidation and/or degradation of the source material and/or active substance. In some embodiments, the sealant is formed of a material suitable to heat the source material, for example when an electrical current and/or a flow of warm air and/or radiation such as infra-red heating and/or other heating methods are applied to the sealant.

In some embodiments, at least one source material section is unsealed (122).

Optionally, all inhalable active substances in the device or at least 90% or at least 95% by weight of the inhalable substances in the device are enclosed within the sealant and inhalation thereof is contingent upon such unsealing. Optionally, at least a portion of the sealant becomes air-permeable, permitting passing of air to and through the source material. In some embodiments, unsealing (e.g. by opening one or more openings through the sealant) is performed by applying a mechanical force to the sealant. Mechanical force may be applied in some embodiments by airflow and/or by adjusting a position of an airflow conducting arrangement. Optionally, this is performed by the device as a necessary step for inhalation of any active substances through the device. Additionally or alternatively, the sealant comprises one or more temperature sensitive control regions, optionally comprising a heat sensitive material and/or structure, and unsealing is performed by heating the sealant. Optionally, the temperature sensitive control regions comprises a shape memory material, such as nitinol.

In some embodiments, the source material is contained and/or otherwise in contact with an element which is air permeable in advance, such as a mesh or a perforated foil.

In some embodiments, the device is configured to simultaneously direct a flow of air to and through the source material of one or more selected sections, and to heat the source material in at least one of the selected sections so that the active substance is released by vaporization of the source material (124).

In some embodiments, the device is configured to deliver more than active substance simultaneously.

In some embodiments, the device comprises an airflow element configured to direct flow through the source material section. Optionally, air entering the device, for example due to suction generated by inhalation of a user through the device, is conducted by the airflow element to the source material. In some embodiments, the airflow element is configured to be moved across the source material, for example moved from section to section.

In some embodiments, the device is configured to heat the source material. In some embodiments, heating is applied to a sealant (e.g. a foil) and/or a heating element (e.g. a mesh) in contact with the source material, for example by applying electricity. In some embodiments, the airflow element comprises electrodes configured to conduct a current to the sealant and/or heating element. Additionally or alternatively, the airflow element is configured to direct flow and to heat the source material section, for example by comprising a heating element (e.g. a mesh).

Additionally or alternatively, heating is applied to the source material by pre-heating the flow of air that is directed to pass through the source material.

In some embodiments, inhalation of the user through the device initiates advancing of the airflow element to a source material section that has not yet been used. In some embodiments, inhalation of the user thorough the device initiates heating of the source material. In some embodiments, inhalation of the user thorough the device initiates unsealing of a sealant of the source material.

In some embodiments, air that exits the heated source material comprises vapors of at least one active substance released from the source material, and is delivered to a user through inhalation (126).

In some embodiments, steps 122-126 are repeated on one or more different source material sections (128). Optionally, the process is repeated in the following inhalation of the user. In some embodiments, a subsequent source material section is automatically unsealed. In some embodiments, the airflow element is automatically moved to the subsequent source material section. Additionally or alternatively, the airflow element is manually moved to the subsequent source material section. In some embodiments, a sealant of the previously heated section is resealed, such as to prevent or reduce air from flowing through the already heated source material.

Figure 1B:
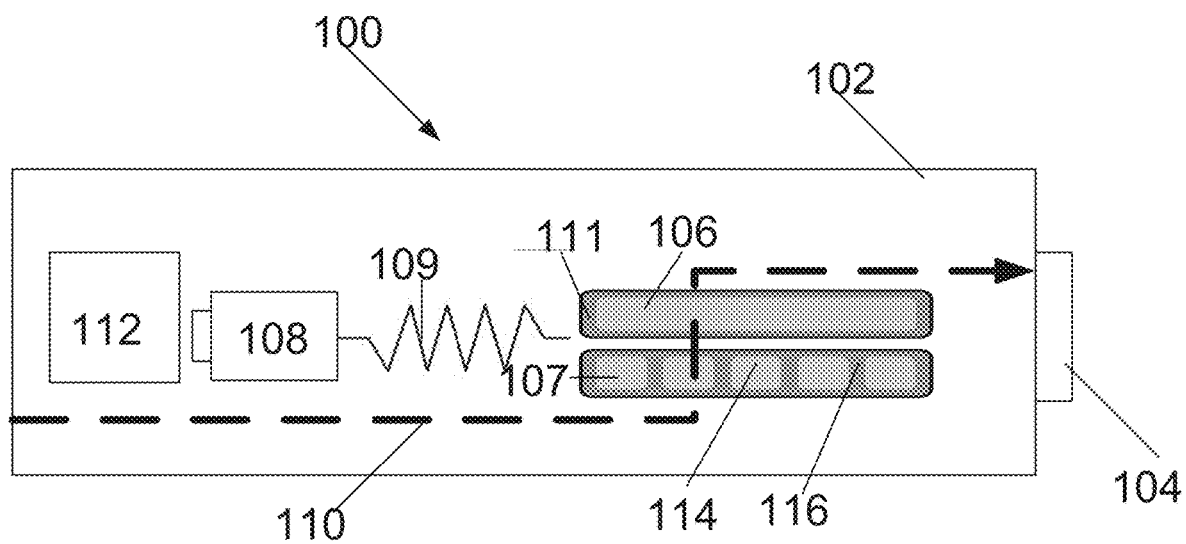
FIG. 1B is a schematic illustration of a device configured to provide at least one active substance through inhalation, according to some embodiments of the invention.

FIG. 1B is a schematic illustration of a device configured to provide at least one active substance through inhalation, according to some embodiments of the invention.

In some embodiments, the device is intended for therapeutic use. Additionally or alternatively, the device is intended for recreational use, for example for vaporizing tobacco and/or *cannabis*.

In some embodiments, device 100 comprises a housing 102; a mouthpiece 104; a cartridge such as 106 and/or 107, comprising one or more source materials; a power source 108 configured to apply electricity 109 to the cartridge so as to vaporize the active substance(s) by heating the source material(s); and/or an airflow conducting arrangement 110 to direct airflow via a heated source material section and through the mouthpiece for inhaling by a user. Optionally, the device comprises a controller 112.

In some embodiments, a cartridge such as 107 comprises separate, discrete source material sections 114. Alternatively, a cartridge such as 106 comprises a single continuous source material spanning one or more source material sections. In some embodiments, the source material is configured within or is otherwise in contact with element 111, which is configured to heat the source material (for example when current is applied to it) and/or to provide structural support to the source material, for example being shaped as a frame containing the source material. In some embodiments, the frame solely holds the source material. Optionally, the source material is held within separate sections, such as sections bordered by walls. Optionally, separation between the sections is configured to isolate the source material sections from each other thermally and/or electrically. Optionally, separation between the sections prevents the sections from being in the same path of airflow. Alternatively, the source material is formed as single solid mass contained within the frame.

In some embodiments, element 111 comprises a mesh or a foil. Optionally, the foil is air-permeable. Alternatively, the foil is not air permeable, and is configured to become air-permeable during use, for example as described hereinbelow.

In some embodiments, a discrete cartridge such as 107 comprises electrically and/or thermally isolating portions 116 configured between the source material sections. In some embodiments, isolating portions 116 comprise or consist of one or more of the following materials: a liquid crystal polymer (LCP), Ultem, Teflon, Torlon, Amodel, Ryton, Forton, Xydear, Radel, Udel, polypropylene, Propylux, polysulfone, polyether sulfone, acrylic, ABS, nylon, PLA, polybenzimadazole, polycarbonate, polyetherimide, polyethylene, polyphenylene oxide, polyphenylene sulfide, polystyrene, polyvinyl chloride, another thermoplastic, Polyimide (PI), a Polyaryletherketone (PAEK), such as Polyether Ether Ketone (PEEK), Poly Ether Ketone (PEK), or Polyetherketoneetherketoneketone (PEKEKK), or a Fluoric polymer, such as Polytetrafluoroethylene (PTFE), Polyvinylidene Fluoride (PVDF), Ethylene tetrafluoroethylene (ETFE), PVDFELS, or Fluorinated Ethylene Propylene (FEP), and/or another polymer material. In some embodiments, portions 116 comprise a conductive material (for example, aluminum). Optionally, portions 116 comprise an electrically insulating layer as an anodized coating.

A potential advantage of LCP and/or PEEK is good resistance to temperature higher than a temperature needed to vaporize a source material held in the cartridge, for example a vaporization temperature of 230° C.

In some embodiments, heating is applied only to a selected source material section (either in cartridge 106 or 107), for example by applying electricity. In some embodiments, air is directed to flow only or mostly through the selected source material section.

In some embodiments, each source material section is heated independently of the other sections, for example by applying a current to a distinct electrically resistive heating element contacting the source material of that section. In some embodiments, heating is performed whilst air is directed to flow through the source material section, to be delivered to the user via the air conducting arrangement 110.

In some embodiments, control over the heated section(s) is provided by controlling the flow of air through the device and/or controlling heating. In some embodiments, airflow is controlled to pass through a certain source material section or a portion thereof. Additionally or alternatively, heating is controlled to vaporize a certain source material section or a portion of it, for example by heating only a portion of element 111. In some embodiments, heating of source material sections other than a targeted section is avoided. Optionally, non-targeted sections include sections that have already been heated and/or sections that have not yet been heated and are different from the targeted section.

In some embodiments, the airflow conducting arrangement 110 is configured to allow airflow within a limited volume of the device. In some embodiments, airflow is directed, optionally via one or more conduits, to pass through a certain target source material section. Additionally or alternatively, a certain degree of drag, obstruction, and/or flow resistance are imposed on inhalation flow drawn by a user through the device, restricting the flow.

In some embodiments, the device comprises a controller 112. In some embodiments, an amount of active substance delivered by the device is controlled using controller 112, for example by adjusting one or more of: heating parameters (e.g. temperature, duration), flow parameters, amount of source material heated, and/or other parameters.

In some embodiments, the source material comprises plant material, such as tobacco and/or *cannabis* and/or other botanic materials. In some embodiments, the released active substance comprises a compound having at least one medicinal and/or somatic and/or psychoactive effect. Optionally the compound includes THC and/or other cannabinoids and/or terpenes and/or nicotine and/or other alkaloids and/or 1,2,3,4-Tetrahydroisoquinolines, Anabasine, Anatabine, Cotinine, Myosmine, Nicotrine, Norcotinine, and/or Nornicotine. In some embodiments, the source material is a volatilizing substance distributed throughout a pallet comprising a carrier material. Optionally, the carrier material comprises at least one botanical substance, such as *cannabis*, tobacco, and/or other plant matter. Additionally or alternatively, the carrier material comprises a porous and air-permeable absorptive matrix; for example, a foam, sponge, felt, and/or another fiber matrix, which absorbs the active substance to fix it into place. In some embodiments, the absorptive matrix is substantially non-friable, providing sufficient strength, for example, to allow direct attachment of other cartridge components, such as a heating element, to or within the absorptive matrix without a requirement for additional mechanical support to preserve the integrity of the absorptive matrix surfaces and/or structure. In some embodiments, the pallet is friable; for example, comprising granules, fibers, or another fine structure compressed to form the pallet.

In some embodiments, the source material comprises one or more isolated materials, essential oils, extracted materials, and/or synthetic compounds.

According to some embodiments, the source material comprises plant material comprising at least one plant material selected from the group consisting of *Cannabis sativa, Cannabis indica, Cannabis ruderalis, Acacia* spp., *Conocybe cyanopus, Conocybe smithii, Copelandia bispora, Copelandia cambodgeniensis, Copelandia cyanescens, Copelandia tropicalis, Galerina steglichii, Gymnopilus aeruginosus, Gymnopilus luteofolius, Gymnopilus spectabilis, Gymnopilus purpuratus, Inocybe aeruginascens, Inocybe calamistrata, Inocybe corydalina* var. *erinaceomorpha, Inocybe haemacta, Panaeolus africanus, Panaeolus casta-* neifolius, Panaeolus subbalteatus, Pluteus salicinus, Psilocybe allenii, Psilocybe antioquensis, Psilocybe arcana, Psilocybe atlantis, Psilocybe aucklandii, Psilocybe australiana, Psilocybe aztecorum, Psilocybe azurescens, Psilocybe baeocystis, Psilocybe bohemica, Psilocybe brasiliensis, Psilocybe caerulescens, Psilocybe caerulipes, Psilocybe columbiana, Psilocybe cordispora, Psilocybe cubensis, Psilocybe cyanescens, Psilocybe cyanofibrillosa, Psilocybe fagicola, Psilocybe fimetaria, Psilocybe heimii, Psilocybe hispanica, Psilocybe hoogshagenii, Psilocybe liniformans var. americana, Psilocybe mexicana, Psilocybe moravica, Psilocybe natalensis, Psilocybe ovoideocystidiata, Psilocybe pelliculosa, Psilocybe portoricensis, Psilocybe quebecensis, Psilocybe samuiensis, Psilocybe sanctorum, Psilocybe semilanceata, Psilocybe semperviva, Psilocybe sierrae, Psilocybe silvatica, Psilocybe stuntzii, Psilocybe stuntzii var. tenuis, Psilocybe subaeruginosa, Psilocybe subcubensis, Psilocybe tampanensis, Psilocybe uxpanapensis, Psilocybe villarrealiae, Psilocybe weilii, Psilocybe xalapenensis, Psilocybe yungensis, Psilocybe zapotecorum, Amanita muscaria, Yage, Atropa belladonna, Areca catechu, Brugmansia spp., Brunfelsia latifolia, Desmanthus illinoensis, Banisteriopsis caapi, Trichocereus spp., Theobroma cacao, Capsicum spp., Cestrum spp., Erythroxylum coca, Solenostemon scutellarioides, Arundo donax, Coffea arabica, Datura spp., Desfontainia spp., Diplopterys cabrerana, Ephedra sinica, Claviceps purpurea, Paullinia cupana, Argyreia nervosa, Hyoscyamus niger, Tabernanthe iboga, Lagochilus inebriens, Justicia pectoralis, Sceletium tortuosum, Piper methysticum, Catha edulis, Mitragyna speciosa, Leonotis leonurus, Nymphaea spp., Nelumbo spp., Sophora secundiflora, Mucuna pruriens, Mandragora officinarum, Mimosa tenuiflora, Ipomoea violacea, Panaeolus spp., Myristica fragrans, Turbina corymbosa, Passiflora incarnata, Lophophora williamsii, Phalaris spp., Duboisia hopwoodii, Papaver somniferum, Psychotria viridis, spp., Salvia divinorum, Combretum quadrangulare, Trichocereus pachanoi, Heimia salicifolia, Stipa robusta, Solandra spp., Hypericum perforatum, Peganum harmala, Tabernaemontana spp., Camellia sinensis, Nicotiana tabacum, Nicotiana rustica, Virola theidora, Voacanga africana, Lactuca virosa, Artemisia absinthium, Ilex paraguariensis, Anadenanthera spp., Corynanthe yohimbe, Calea zacatechichi, Coffea spp. (Rubiaceae), Sapindaceae spp., Camellia spp., Malvaceae spp., Aquifoliaceae spp., Hoodia spp. Chamomilla recutita, Passiflora incarnate, Camellia sinensis, Mentha piperita, Mentha spicata, Rubus idaeus, Eucalyptus globulus, Lavandula officinalis, Thymus vulgaris, Melissa officinalis, Tobacco, Aloe Vera, Angelica, Anise, Ayahuasca (Banisteriopsis caapi), Barberry, Black Horehound, Blue Lotus, Burdock, Camomille/Chamomile, Caraway, Cat's Claw, Clove, Comfrey, Corn Silk, Couch Grass, Damiana, Damiana, Dandelion, Ephedra, Eucalyptus, Evening Primrose, Fennel, Feverfew, Fringe Tree, Garlic, Ginger, Ginkgo, Ginseng, Goldenrod, Goldenseal, Gotu Kola, Green Tea, Guarana, Hawthorn, Hops, Horsetail, Hyssop, Kola Nut, Kratom, Lavender, Lemon Balm, Licorice, Lion's Tail (Wild Dagga), Maca Root, Marshmallow, Meadowsweet, Milk Thistle, Motherwort, Passion Flower, Passionflower, Peppermint, Prickly Poppy, Purslane, Raspberry Leaf, Red Poppy, Sage, Saw Palmetto, Sida Cordifolia, Sinicuichi (Mayan Sun Opener), Spearmint, Sweet Flag, Syrian Rue (Peganum harmala), Thyme, Turmeric, Valerian, Wild Yam, Wormwood, Yarrow, Yerba Mate, and Yohimbe. In some embodiments, the source material comprises one or more active substances extracted and/or isolated from one or more of the aforesaid plants and/or a synthetic version of such active substances.

In some embodiments, the source material comprises different plants, different strains, different blends, different additives, and/or different concentrations of one or more substances.

In some embodiments, the source material vaporizes at a temperature requiring a substantial exogenous heat input to reach a temperature above ambient temperature. For example, the substance vaporizes at a temperature within the range from 80° C.-250° C., or within another range having the same, higher, lower, intermediate and/or intermediate bounds, for example between 160-230° C. In some embodiments, the substance vaporizes at a temperature above 80° C., 100° C., 150° C., 200° C., 230° C., or another higher, lower, or intermediate temperature. In some embodiments, the time to reach a volatilizing temperature is, for example, about in a range between about 100 msec-5 sec, 100-750 msec, 150-300 msec, or another range having the same, larger, smaller, and/or intermediate bounds. In particular, the time is, for example, 250 msec, 500 msec, 1000 msec, or another greater, smaller, or intermediate value. In an example, nicotine is extracted at a boiling point of about 247 degrees Celsius, over a time period of about 3 seconds or less. In some embodiments, element 111 is electrically resistive. Optionally element 111 consists of or comprises a metal, for example nichrome, FeCrAl, cupronickel, titanium, and/or stainless steel.

In some embodiments, element 111 is packaged in thermal contact with the source material, so as to heat the source material. Thermal contact comprises, for example, being in direct contact, or in contact across a heat-transmitting layer allowing a high rate of thermal transfer (for example, comprised of a high heat conductance material such as copper, aluminum, brass or steel; and/or having a thin-walled construction of less than about 10 µm, 20 µm, 25 µm, 50 µm, or another greater, lesser or intermediate thickness). In some embodiments, thermal contact comprises sufficiently close apposition of pallet and element 111 that the pallet subtends substantially the whole thermal radiating angle of the portion of the element overlying it; for example, more than 90%, 95%, 99%, or another greater, lesser or intermediate value. In some embodiments, the peak current applied to the electrode is in the range of about 1-10 Amperes; for example, about 1 Amperes, 2 Amperes, 4 Amperes, 6 Amperes, or another higher, lower, or intermediate current.

In some embodiments, the thermal contact comprises element 111 extending across and in contact with one or more surfaces of the pallet, for example, one side, or two opposite, largest surface-area sides of the pallet. In some embodiments, the thermal contact comprises the element 111 being at least partially embedded within the pallet.

In some embodiments, element 111 is permeable to the passage of air. In some embodiments, the pallet is permeable to the passage of air. Permeability is under conditions, for example, of the passage of air at ambient temperature through a heated assembly of pallet and element 111 under a suction pressure such as a suction pressure generated by inhaling, and/or a positive pressure generated from a side away from the inhaling side of the cartridge. In some embodiments, the applied pressure is in the range of 5-20 mmHg, 10-25 mmHg, 5-30 mmHg, 25-40 mmHg, 30-50 mmHg, or another range having the same, higher, lower, and/or intermediate bounds. According to some embodiments, the pallet has an air-permeable structure that allows a flow of at least 0.5 liters of gas per minute or even at least 0.75 liter of gas per minute or 1 liter of gas per minute under a pulling vacuum of at least 1-5 kPa (−1-(−5) kPa). In some embodiments, the pallet has this permeability in its packaged form. In some embodiments, this permeability is reached during heating of the pallet, for example, due to volatilization, drying, melting, and/or burning of the pallet constituents.

In some embodiments, power source 108 is configured to supply enough power to heat a selected number of source material sections 114. Optionally, power source 108 is configured to supply enough power to heat all of the source material contained within the device. In some embodiments, the power source is a battery. Optionally, the battery is rechargeable. Optionally, the battery is chargeable externally to the device.

FIGS. 2A-C illustrate three configurations of a coupling between source material and an electrically resistive heating element, according to some embodiments of the invention.

In some embodiments, the source material 200 is coupled to an electrically resistive heating element 202, such as a mesh or foil.

In some embodiments, a coupling between the source material and heating element is configured to provide for homogenous heating of the source material.

Optionally, the source material is formed—before or during insertion—such that it conforms to an optionally flattened shape of the heating element. It is a potential advantage for the source material to be held in a flattened format, since a greater surface area and/or a more uniform thickness potentially allow faster and/or more evenly distributed heating and/or airflow during dosage vaporization and delivery. In some embodiments, a thickness of the source material as measured along the direction in which air flows through the source material ranges between 0.5-5 mm, or between 0.5-2 mm, or between 0.5-1.5 mm, such as 1 mm, 2.5 mm, 4 mm or intermediate, higher or lower thicknesses.

In the example shown in FIG. 2A, the source material is sandwiched between two heating elements. A potential advantage of two-sided enclosure of the source material, used in some embodiments, is increased speed and/or uniformity of volatilization upon application of a current to the heating element.

In the example shown in FIG. 2B, a bottom surface of the source material contacts the heating element. Alternatively, a top surface of the source material may come in contact with the heating element.

In the example shown in FIG. 2C, the heating element is embedded within the source material.

In some embodiments, source material 200 and/or heating element 202 are arranged to provide for airflow 204 to pass through. Optionally, heating element 202 is a mesh and/or other air-permeable structure. Optionally, source material 200 consists of or is contained within a porous matrix and/or is otherwise arranged to allow a flow of air through.

Alternatively, the heating element is impermeable to air. Optionally, the heating element is configured to become permeable during use.

In some embodiments, a heating element comprises an infra-red heater.

Figure 3:
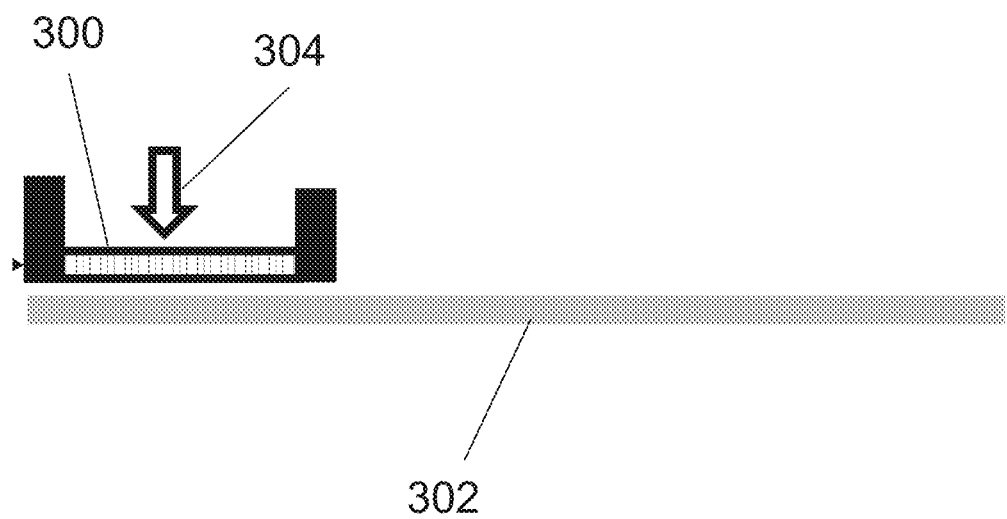
FIG. 3 illustrates a configuration in which a heating element is movable with respect to the source material, according to some embodiments of the invention.

FIG. 3 illustrates a configuration in which a heating element 300 is movable with respect to source material 302, according to some embodiments of the invention.

In some embodiments, optionally during use, heating element 300 is moved to a position in which it contacts the source material or a portion thereof. Optionally, the heating element is configured to be advanced over the source material so as to heat a different portion of the source material. Optionally, the heating element is sized to contact a portion of the source material comprising an amount of active substance which when vaporized provides a single predetermined dose. In some embodiments, the source material includes a support structure (not shown). Optionally, the support structure is air permeable. Optionally, the support structure is heat resistant. In some embodiments, the movable heating element is configured to attach to the support structure. In some embodiments, the movable heating element is configured as a part of and/or comprises an airflow element, for example as further described herein, directing airflow 304 through the heated active substance section.

Figure 4A:
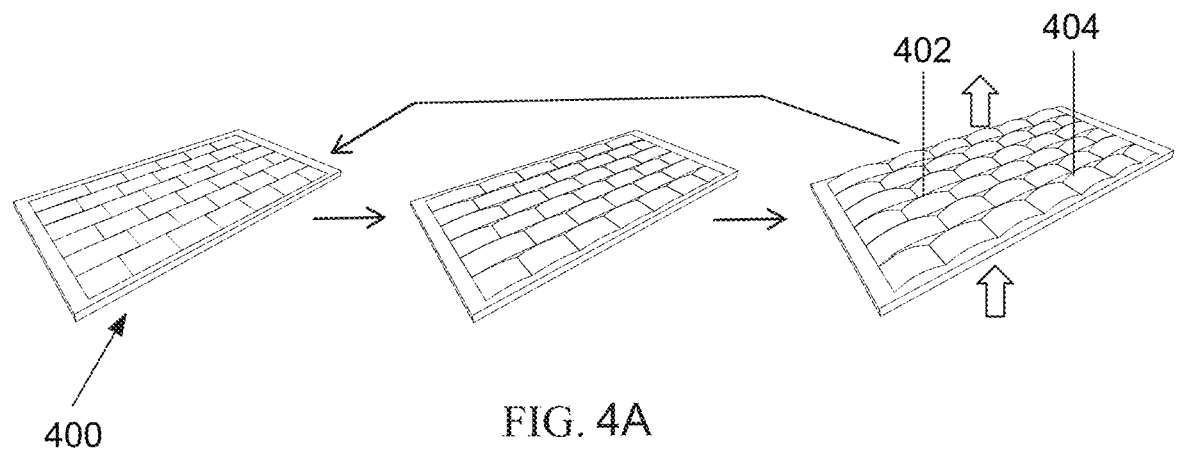
FIGS. 4A-C show methods and/or structures for dynamically changing air permeability of a heating element and/or a sealant of the source material, according to some embodiments of the invention.
Figure 4B:
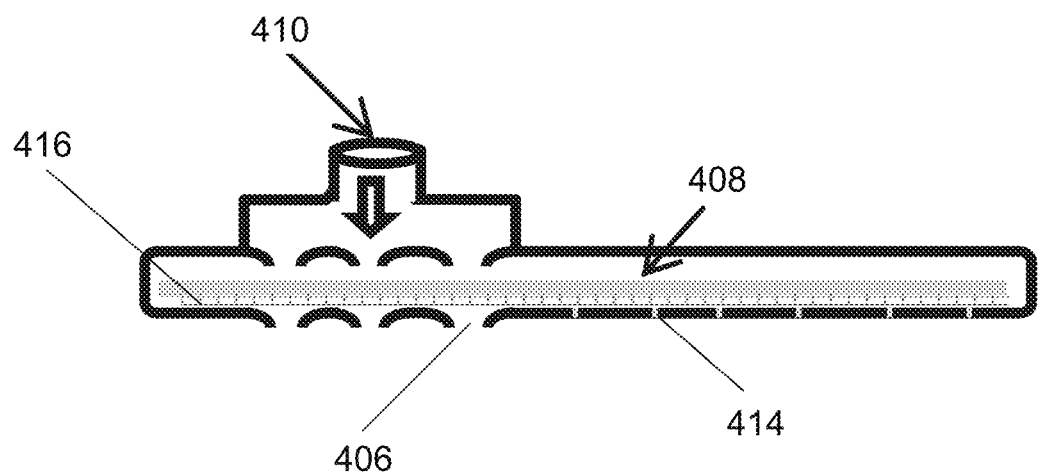
Figure 4C:
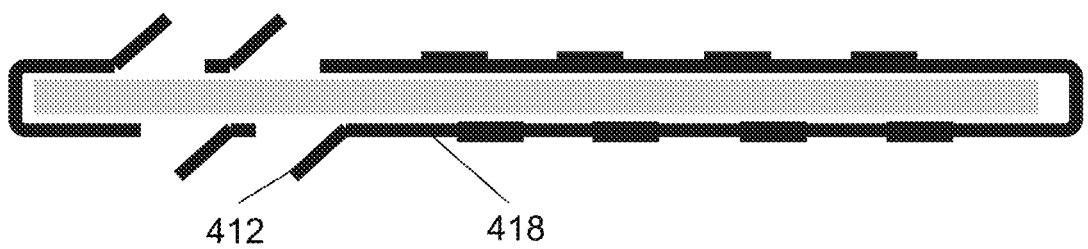

FIGS. 4A-C show methods and/or structures for dynamically changing air permeability of a heating element and/or of a sealant of the source material, according to some embodiments of the invention. In some embodiments, the sealant is configured to for heating the source material and therefore functions as a heating element.

In some embodiments, the heating element or at least a portion of the heating element is air permeable in advance. Alternatively, the heating element is sealed and during use it is unsealed to allow air to pass through the source material. FIGS. 4A-C illustrate various methods and structures for dynamically changing air permeability of the heating element and/or sealant of the source material.

In some embodiments, as shown for example in FIG. 4A, the heating element is a foil 400 that comprises one or more force sensitive control regions 402. When force (such as pressure, stretch, contortion, and/or a bending force) is applied to the foil, the force sensitive regions or portions thereof deform to allow airflow to pass through. Optionally the flow is airflow caused by a user inhaling through the device.

Optionally, the force sensitive control regions are etched into the foil.

Additionally or alternatively, the foil is perforated. Additionally or alternatively, the foil is folded over itself to form a scale-like arrangement.

In some embodiments, the heating element comprises temperature sensitive control regions. Optionally, the temperature sensitive regions comprise shape memory material. Optionally, during heating, the regions or portions thereof deform to allow a flow of air through. In some embodiments, when the heating element cools down, the temperature sensitive regions close back. A potential advantage of using temperature sensitive regions may include an inherent airflow arrangement, enabling flow of air only through heated portions and ensuring obstruction of flow through non-heated portions. Optionally the direction of the deformation will cause greater surface contact between the heating element and the substance.

In the example of FIG. 4A, foil 400 comprises a 316L stainless steel foil, or alternatively a shape memory conductive material, such as nitinol and/or Cu—Al—Ni alloys and/or Fe—Mn—Si—Cr—Ni alloys and/or Cu50Zr50. In some embodiments, a scale-like pattern is etched onto the foil. Optionally, when force is applied and/or when the foil is heated, the foil deforms (e.g. expands or contorts) and at least some of the regions change shape to allow passing of air through, for example through openings 404. In some embodiments, applying force in an opposite direction and/or cooling of the foil deforms the regions back to their original configuration, and the openings through which the air passed close.

In some embodiments, as shown for example in FIG. 4B, sealant 414 is configured to operate as a one way valve. Optionally, when suction and/or air pressure is applied (for example during inhalation of the user through the device), one or more valves 406 configured in sealant 414 move to allow air to pass through the source material 408. Optionally, the valves are formed as integral sections of the sealant. In some embodiments, when suction ceases (for example when inhalation stops), the valves move to a closed position. In a configuration as described, it may be advantageous to use a sealant in the form of a foil, for example a stainless steel foil, or a flexible sealant, for example made of silicone.

In some embodiments, a heating element 416 is configured in between sealant 414 and source material 408.

In some embodiments, as also shown in the example of FIG. 4B, an airflow element 410 is used. Optionally, the airflow element is movable (e.g. by sliding) on sealant 414 and/or on heating element 416 and/or directly on the source material and/or via a supporting structure. In some embodiments, the airflow element is positioned over a portion of the sealant such that only valves configured within that portion open to allow air to pass through, for example when suction and/or air pressure are induced via the airflow element.

In some embodiments, as shown for example in FIG. 4C, a heating element 418 comprises a shape memory material, such as nitinol. Optionally, during heating, one or more leaflets 412 formed in the foil deform (e.g. are lifted away from the source material) to allow flow of air through. In some embodiments, when electrification ceases and the heating element cools down, the leaflets deform back to their closed configuration. Additionally or alternatively, a mechanical force is applied to re-seal the leaflets, for example using a stamp or a roller.

Additionally or alternatively, the heating element is air permeable and is coated by a sealed layer that is unsealed during use to expose the heating element.

Additionally or alternatively, a mechanical element configured to perforate the heating element is used, for example in the form of a roller knife or punch.

Optionally, in embodiments in which the heating element is air permeable and comprises a seal or coating for example as described above, a mechanical element shaped and/or sized to tear open and/or perforate and/or remove a part of the seal is used.

Additionally or alternatively, a seal or coating of the heating element is manually removed by the user and/or mechanically removed, for example upon insertion of a cartridge into the device.

In some embodiments, a sealant of the source material comprises a silicone membrane. Optionally, the source material is enclosed within a mesh or a foil and the silicone membrane is a coating on the mesh of foil. Optionally, the silicone membrane is between 100-500 microns thick, for example 200 microns, 300 microns, 400 microns. In some embodiments, the silicone membrane comprises slits which open to allow air to pass through in response to pressure such as air pressure applied when the flow of air is directed to the source material section, for example air pressure induced by inhalation. Additionally or alternatively, the sealant comprises a thin layer of perfluoroalkoxy (PFA) film, for example having a thickness between 10-50 microns, such as 15 microns, 25 microns, 40 microns. Optionally, the film comprises slits for example as described hereinabove. Optionally, the material is elastic enough so that when pressure such as air pressure is ceased, the slits close back to a sealing position.

In some embodiments, a sealant encloses a material that is configured for occupying a larger volume when heat is applied to it, for example an inert non-toxic gas having a low boiling temperature (e.g. Helium), a solid and/or a liquid configured to sublimate. Optionally, application of heat will cause the material to expand and to rupture the sealant.

Figure 5A:
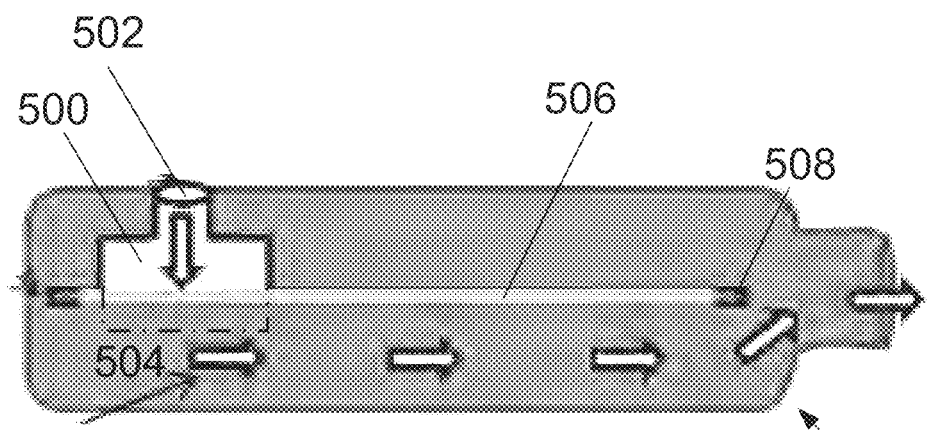
FIGS. 5A-B illustrate two flow patterns in which airflow is directed through the source material for delivering active substance imbued air to the user, according to some embodiments of the invention.
Figure 5B:
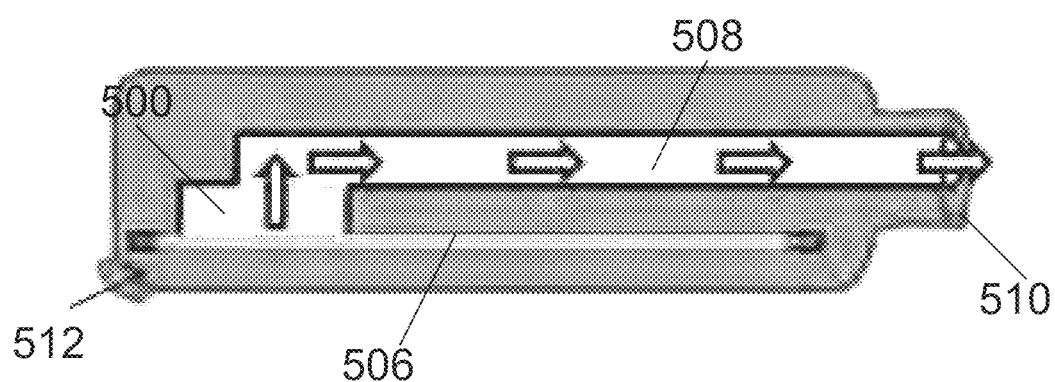

FIGS. 5A-B illustrate two flow patterns in which airflow is directed through the source material for delivering active substance imbued air to the user, according to some embodiments of the invention.

In some embodiments, device 514 comprises an airflow element 500, comprising one or more conduits and/or valves other structures suitable to direct a flow of air through the source material or a selected portion of it. In some embodiments, airflow element 500 defines a conduit 502 through which suction is induced, for example during inhalation, directing airflow that enters the device through at least a portion 504 of the source material 506.

In some embodiments, airflow element 500 comprises one or more electrical contacts (not shown) for conducting a current to at least a portion of a heating element 508 which is in contact with the source material. In some embodiments, the electrical contacts are shaped to conduct a current to a limited area of the heating element corresponding at least partially to portion 504. Optionally, the electrical contacts are configured at the edges of the airflow element, thereby spanning the source material on opposing sides.

In some embodiments, airflow element 500 is configured to be moved across the source material, for example by sliding, rolling, being dragged on and/or otherwise moved along the source material. In some embodiments, movement of airflow element 500 is manual, for example using a manual slider. Optionally, this slider is moveable by a user using one hand also holding the inhaler device, for example by thumb actuation. Additionally or alternatively, movement of airflow element 500 is automated. In embodiments in which the device comprises a controller, the controller may be configured to activate, modify and/or cease movement of the airflow element.

In some embodiments, the airflow element is moved between successive delivery events (i.e. events in which active substance vapors are delivered to the user through inhalation) heat a different portion of the source material in each event.

Optionally, a delivery event includes a single inhalation. Alternatively, a delivery event includes a plurality of inhalations. In some embodiments, the airflow element is moved to a different source material portion only after a number of delivery events. Optionally, the number of delivery events is predetermined.

Additionally or alternatively, the airflow element is configured to move a different source material portion when a predetermined amount or instead all the source material of a currently heated portion has been consumed.

In some embodiments, the airflow element is shaped to direct flow through more than one source material sections. Optionally, a plurality of source material sections are heated when the airflow element moves to a position suitable to provide airflow and apply electricity to that plurality of source material sections. Optionally, the plurality of sections are heated at the same time. Alternatively, the plurality of active substance sections are heated one after the other. Optionally a heating element is positioned at one location for a plurality of inhalations, whilst each inhalation is associated with heating a different portion or section of the source material that is within portion 504.

In the cross-section illustration of FIG. 5A, a flow of air entering conduit 502 of airflow element 500 is directed to pass through source material portion 504 and continues to flow, as active substance imbued air, towards mouthpiece 510 to be delivered to the user.

In the cross section illustration of FIG. 5B, flow entering the device through opening 512 is forced to pass through source material 506. In this example, airflow element 500 is positioned above the source material. Optionally, active substance imbued air is delivered to the user via a conduit 508, extending to mouthpiece 510.

Figure 6A:
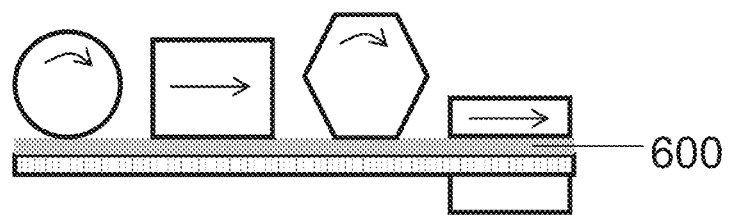
FIGS. 6A-C illustrate mechanisms of moving an airflow element along the source material, according to some embodiments of the invention.
Figure 6B:
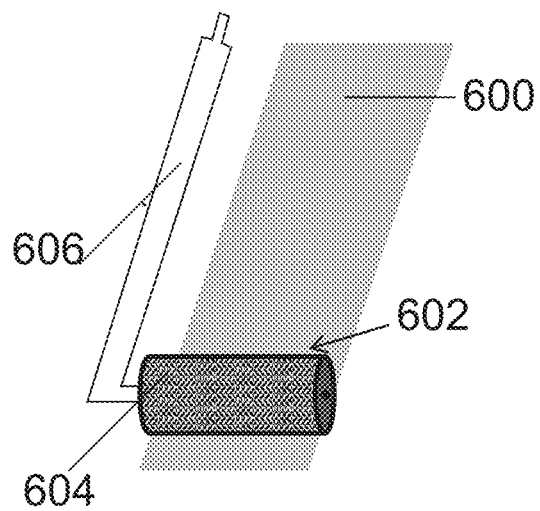
Figure 6C:
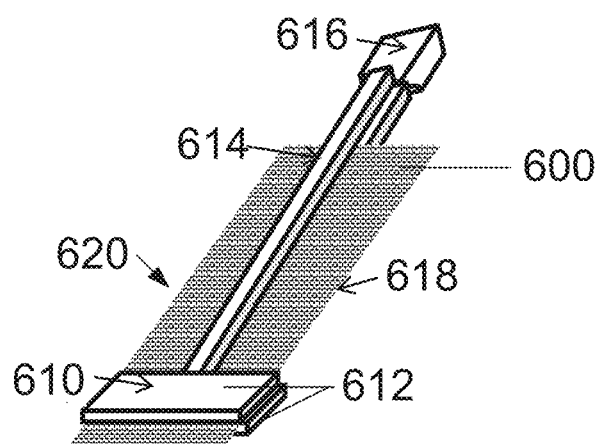

FIGS. 6A-C illustrate mechanisms of moving an airflow element along the source material, according to some embodiments.

FIG. 6A schematically illustrates movement of an airflow element along the source material 600, including, for example, movement by way of rolling, sliding, being dragged along the source material and/or other ways of movement. Optionally, the airflow element is positioned above the source material. Additionally or alternatively, the airflow element is positioned below the source material.

In FIG. 6B, an airflow element 602 comprises a roller 604 configured for rolling over a surface of source material 600, according to some embodiments.

Optionally, roller 604 is coupled to a lever 606 configured for pulling and/or pushing the roller across the source material 600. In some embodiments, roller 604 comprises a mesh and/or foil and/or other perforated surface, configured to heat when a current is applied so as the heat the source material in contact with the roller.

Optionally the roller is partially enclosed by a sealing region that directs airflow in a desired direction.

In some embodiments, a surface of the roller is spiked. Optionally, the spiked surface is not perforated but is configured to perforate holes in a sealant covering the source material, according to some embodiments.

In FIG. 6C, cartridge 620 comprises source material 600 contained within and/or sandwiched between layers of an air permeable heating element 618, according to some embodiments. Optionally, airflow element 610 comprises of two opposing surfaces 612, positioned such that source material 600 is sandwiched between them. Conduits 614 extend from the surfaces to mouthpiece 616, for allowing the passing of air through.

It is noted that the examples of source material are shown herein as flat strips, but other configurations such as a tubular arrangement (for example having a round or polygonal cross section profile) and/or any other shapes are also contemplated.

Figure 7:
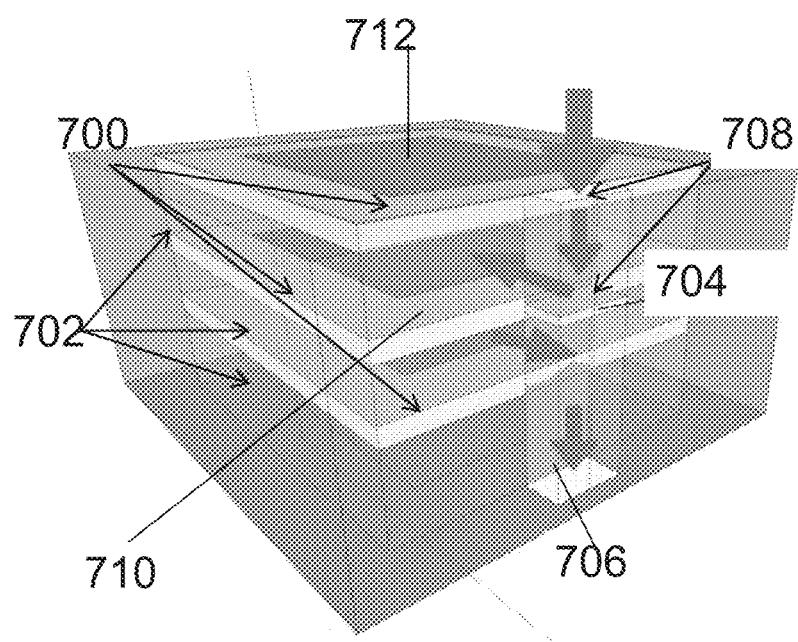
FIG. 7 schematically illustrates a dynamic airflow element, configured to direct air through a selected source material section, according to some embodiments of the invention.

FIG. 7 schematically illustrates a dynamic airflow element, configured to direct air through a selected source material section, according to some embodiments of the invention. In this example, source material is stacked in layers 702, each layer contained within a frame 700 and defining a source material section. In the example shown herein, each layer comprises a flattened (optionally square shaped) mass of source material. It is noted that other layer configurations and/or source material layout configurations are contemplated as well.

In some embodiments, an electrically resistive element 712, such as a foil or a mesh which is configured to heat the source material, is in contact with the source material, for example covering at least one surface of the source material and/or spanning the source material from both sides of the opening in the frame.

In some embodiments, airflow element 706 comprises a movable blocking member 704 configured to direct air to pass only through a certain source material section. In the example shown herein, airflow 708 passes through a conduit of airflow element 706, being directed into middle section 710 by blocking member 704, passing through the source material 700 and then flowing back into the conduit of airflow element 706 to be delivered to a user.

Figure 8A:
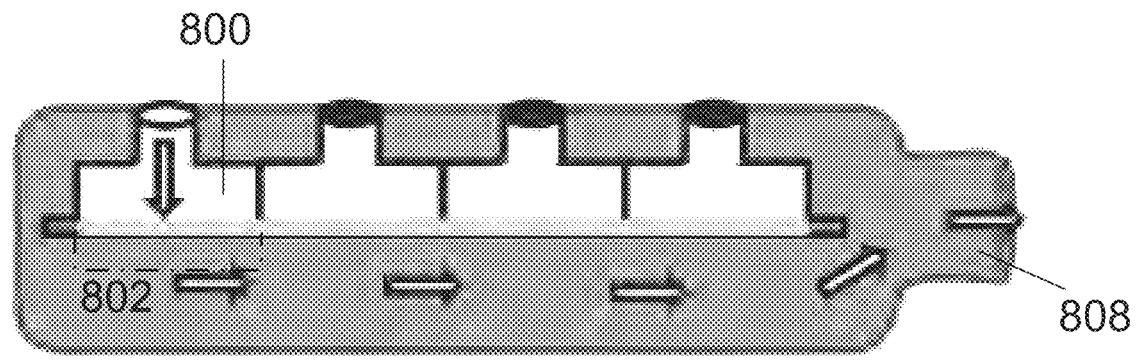
FIGS. 8A-B illustrate operation of a device comprising a plurality of airflow elements, according to some embodiments of the invention.
Figure 8B:
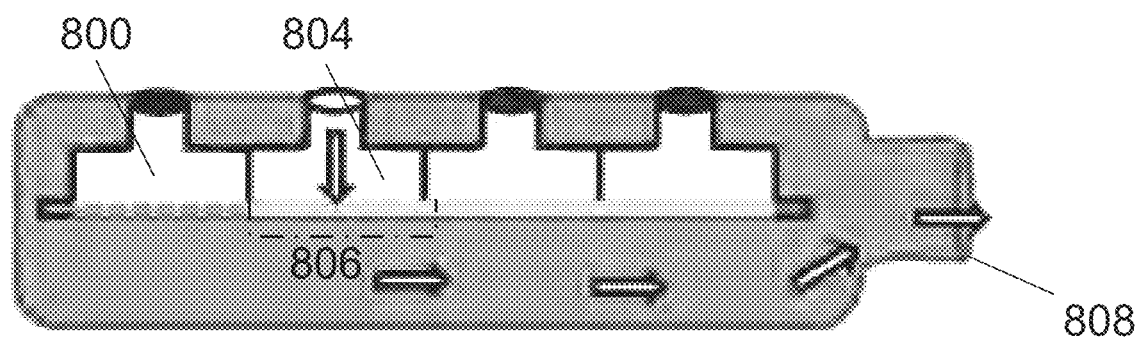

FIGS. 8A-B illustrate operation of a device comprising a plurality of airflow elements, according to some embodiments of the invention.

In some embodiments, a plurality of airflow elements are positioned to direct flow and/or apply a current to a plurality of corresponding source material sections that are associated with the airflow elements. In some embodiments, airflow is selectively directed through one or more of the airflow elements and not through others. In FIG. 8A, airflow is directed to pass through the first airflow element 800, passing through a first portion of the source material 802 and continuing to flow towards mouthpiece 808 to be delivered to the user. In FIG. 8B, airflow is directed to pass through the second airflow element 804, passing through a second portion of the source material 806 and continuing to flow towards mouthpiece 808 to be delivered to the user. Optionally, the first airflow element 800 is blocked to eliminate flow through the first active substance section 802 after it was used. In some embodiments, a portion of the source material through which air is allowed to pass, such as portion 802, comprises a single active substance dose. Alternatively, portion 802 comprises a plurality of dose sections, and each may be heated separately, for example for each delivery event. Optionally, the portion is delivered to the user in a single delivery event (for example a single activation of the device, optionally including one or more successive inhalations of the user through the device).

Figure 9:
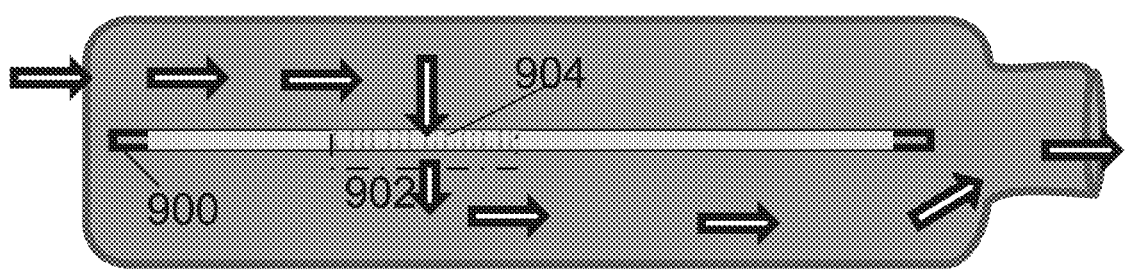
FIG. 9 schematically illustrates a heating element and/or a sealant configured to allow airflow through a source material section currently being heated and to block flow through non-heated source material sections, according to some embodiments.

FIG. 9 schematically illustrates a heating element 900 configured to allow airflow through a source material section 902 currently being heated and to block flow through currently non-used sections, according to some embodiments. In some embodiments, heating element 900, for example in the form of a foil containing the source material, comprises one or more portions 904 which are configured to become air permeable during use so as to allow airflow through a heated source material section. Optionally, when heating ceases, the permeable foil portion is sealed back.

Optionally, for example in the following delivery event and/or following inhalation, a different foil portion becomes air permeable, allowing flow through a different source material portion.

In some embodiments, a foil portion such as portion 904 is coupled to an electrode set through which current is applied to the foil. Optionally, a plurality of foil portions are coupled to a plurality of corresponding electrode sets. Optionally, the electrode sets are activated separately to target different source material sections. In some embodiments, for example in a device as shown in this figure, the device comprises a controller and the controller is configured to control the separate heating of different sections of source material.

FIGS. 10A-F illustrate a cigarette like device, comprising a cylindrical configuration, according to some embodiments of the invention.

Figure 10A:
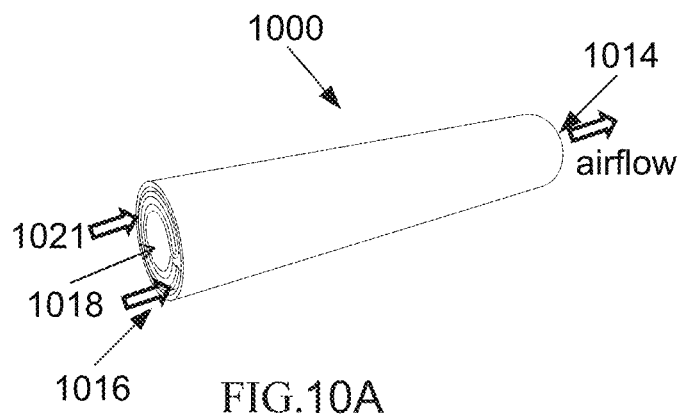
FIGS. 10A-F illustrate a cigarette device, comprising a cylindrical configuration, according to some embodiments of the invention.
Figure 10B:
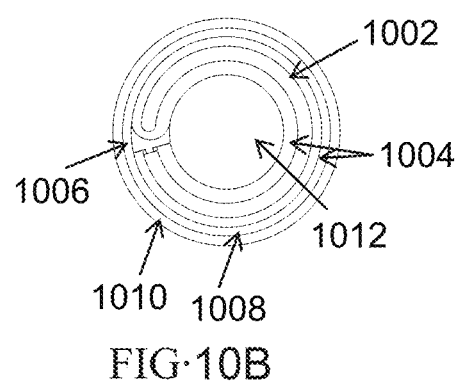
Figure 10C:
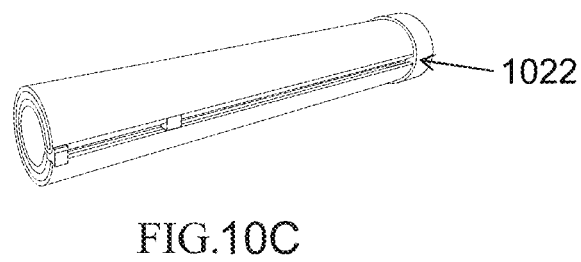
Figure 10D:
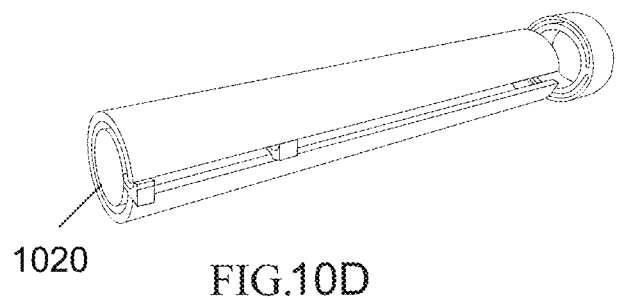

FIG. 10A shows an isometric view of device 1000. FIG. 10B shows a cross section view of device 1000. FIGS. 10C and 10D show different partial exploded views of device 1000.

In some embodiments, as shown in FIG. 10B, source material 1002 comprises an annular cross section profile. In some embodiments, the source material is enclosed between inner and outer foil layers 1004, configured to heat the source material, for example by applying electricity to the foil. In some embodiments, electricity is applied via a pair of electrodes 1006, configured in contact with foil 1004. In some embodiments, the outer foil is surrounded by a housing 1010.

Optionally, housing 1010 comprises a durable inert material. In some embodiments, this durable inert material comprises or consists of one or more of the following materials: a liquid crystal polymer (LCP), polyether ether ketone (PEEK), Ultem, Teflon, Torlon, Amodel, Ryton, Forton, Xydear, Radel, Udel, polypropylene, Propylux, polysulfone, polyether sulfone, acrylic, ABS, nylon, PLA, polybenzimadazole, polycarbonate, polyetherimide, polyethylene, polyphenylene oxide, polyphenylene sulfide, polystyrene, polyvinyl chloride, another thermoplastic, and/or another polymer material.

In some embodiments, a cylindrical lumen 1008 exists between outer foil 1004 and housing 1010, through which air can flow. In some embodiments, a cannula 1012 extends between a proximal end 1014 and a distal end 1016 of the device (see FIG. 10A). Optionally, the cannula serves a conduit for active substance imbued air flowing in a proximal direction to be delivered to the user.

In some embodiments, distal end 1016 comprises a sealed portion 1018, and an open portion 1020 (shown more clearly in FIG. 10D), configured radially outwards relative to the seal, which provides for airflow 1021 to enter the device around the seal, flowing into lumen 1008 and circumferentially around outer foil 1004.

In some embodiments, the air flows from lumen 1008 in a radially inward direction through the outer foil, through a section of the source material currently being heated, through the inner foil, and into cannula 1012 from which it continues towards mouthpiece 1022 positioned at proximal end 1014 of the device. Airflow entering mouthpiece 1022 comprises the at least one active substance, for example in the form of vapors extracted from the heated section of the source material. In some embodiments, mouthpiece 1022 is configured to prevent flow at the circumference (for example flow within lumen 1008) from entering the user's mouth. Optionally, only axial flow is allowed to pass through. In some embodiments, reverse airflow (i.e. air flowing from the user to the source material or similar direction) is prevented, for example by use of one or more check valves and/or other elements suitable to prevent reverse airflow.

In some embodiments, electrodes 1006 are configured to advance along the cylinder so as to heat a different source material section. Additionally or alternatively, a plurality of electrodes are arranged along the length of the cylinder, and are activated in turn for delivering a current to heat a respective foil section.

Figure 10E:
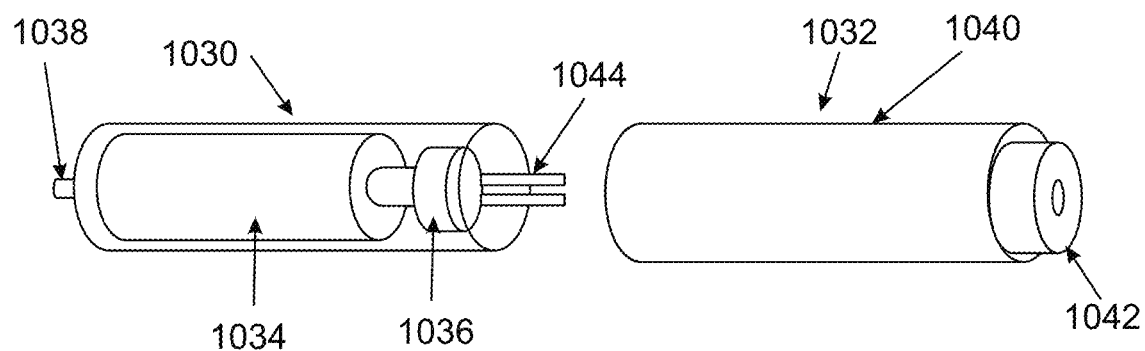
Figure 10F:
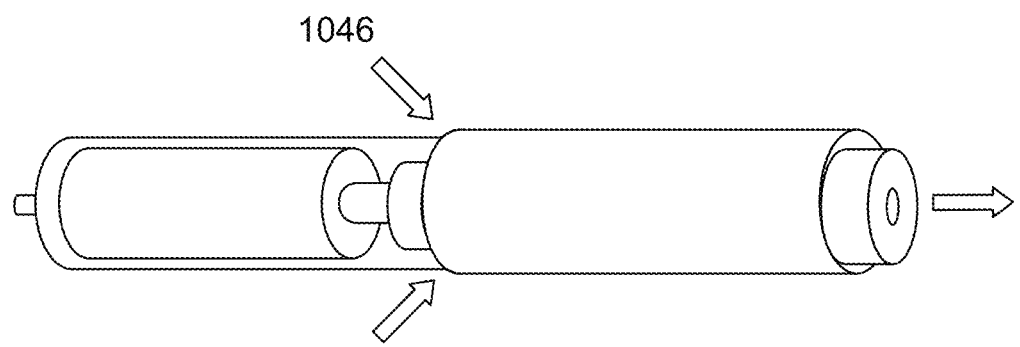

FIGS. 10E and 10F illustrate an electronic cigarette comprising a first portion 1030 and a second portion 1032. Optionally, the first and second portions are axially coupled to each other, to produce an elongated cylindrical configuration as seen for example in FIG. 10F.

In some embodiments, first portion 1030 houses a battery 1034 and/or a controller 1036. Optionally, a light indication 1038 (e.g. LED) is configured externally to the first portion, for indicating the battery's power level and/or other operational indications.

In some embodiments, second portion 1032 comprises a cartridge 1040 of source material. In some embodiments, second portion 1032 comprises a mouthpiece 1042 configured at a proximal end of the portion. In some embodiments second portion 1032 comprises device 1000 for example as shown in FIGS. 10A-10D.

In some embodiments, portions 1030 and 1032 are mechanically and/or electrically coupled to each other, for example via connectors 1044 which extend proximally from first portion 1030 to be received within portion 1032. Optionally connectors 1044 consist of or comprise electrical connectors, for applying electricity to cartridge 1040 so as to heat the source material contained within the cartridge.

Additionally or alternatively, other connectors may be used to connect the portion.

In some embodiments, airflow 1046 enters portion 1032 through a circumferential opening on a distal end of portion 1032, for example as shown in FIG. 10F and in FIG. 10A. In some embodiments, the source material contained within the cartridge is protected by a sealant which is configured to be unsealed during use, for example as described hereinabove, to allow airflow 1046 through. In some embodiments, portion 1032 is disposable, and portion 1030 is configured for at least a plurality of uses. Optionally, battery 1034 is rechargeable.

In some embodiments, portion 1032 comprises a chip (not shown herein) coded with a delivery schedule and/or a dosing regimen and/or with personal user data. Optionally, a coupling between the portions is configured to transfer data (for example via a USB connection) so that controller 1036 controls delivery according to the data coded in portion 1032.

Figure 11A:
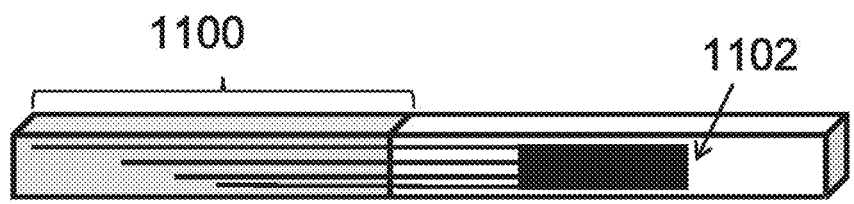
FIGS. 11A-C illustrate various disposable and/or replaceable components of the device, according to some embodiments of the invention.
Figure 11B:
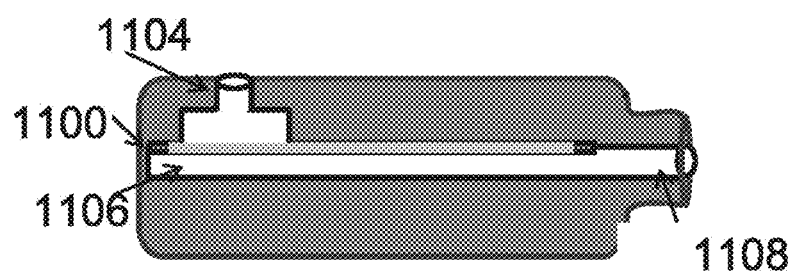
Figure 11C:
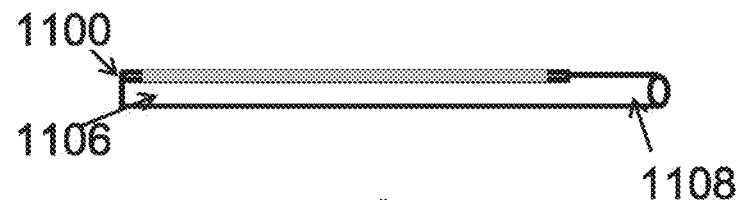

FIGS. 11A-C illustrate various disposable and/or replaceable components of the device, according to some embodiments of the invention.

In some embodiments, the whole device is configured for single use.

Alternatively, one or more components such as a cartridge 1100 comprising the source material (shown in FIG. 11A) and/or a battery 1102 (shown in FIG. 11A) and/or an airflow element 1104 (shown in FIG. 11B) and/or a conduit 1106 through which the flow passes (shown in FIGS. 11B and 11C) and/or a mouthpiece component 1108 (shown in FIGS. 11B and 11C) are disposable. The mouthpiece component may be a mouthpiece configured to allow airflow from the device to a user and/or a lining for a mouthpiece included in the device.

In an example, as shown in FIG. 11C, cartridge 1100, conduit 1106 and mouthpiece component 1108 form a single replaceable unit.

In some embodiments, one or more of the above components are disposed and optionally replaced between delivery events. Additionally or alternatively, one or more of the above components are disposed and optionally replaced between different users. Additionally or alternatively, one or more of the above components are disposed and optionally replaced after a predetermined time period. Additionally or alternatively, one or more of the above components are disposed and optionally replaced once all source material was consumed.

A potential advantage of using disposable components for some or all components through which active substance imbued airflow passes may include preventing excessive buildup of condensed active substance residue resulting for example from use of a plurality of cartridges, which may in turn reduce the hazard of malodor during use.

FIGS. 12A-E are various views of a substantially flat, rectangular vaporizing device, according to some embodiments of the invention.

It is noted that the flat rectangular device is only a configuration provided as an example, and the device may comprise other forms, optionally non-flat, such as a tubular configuration, a disc-like configuration, a triangular configuration and/or other.

Figure 12A:
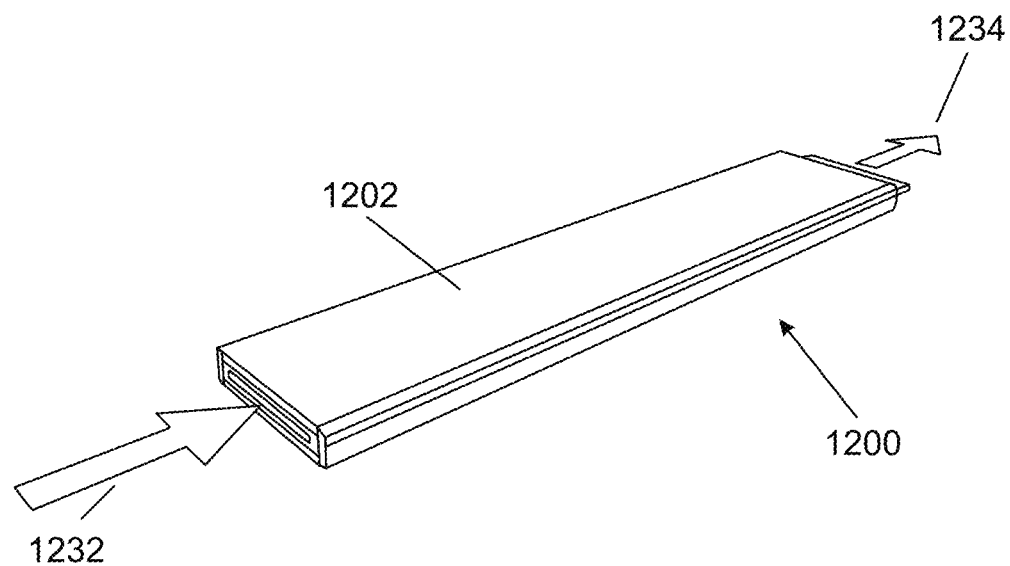
FIGS. 12A-E are various views of a flat rectangular device, according to some embodiments of the invention.
Figure 12B:
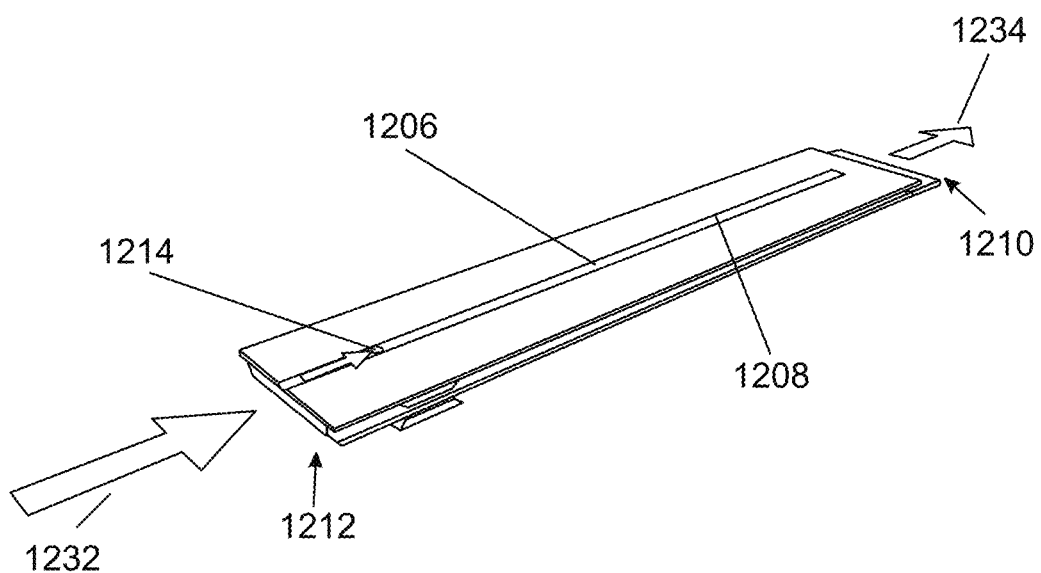
Figure 12C:
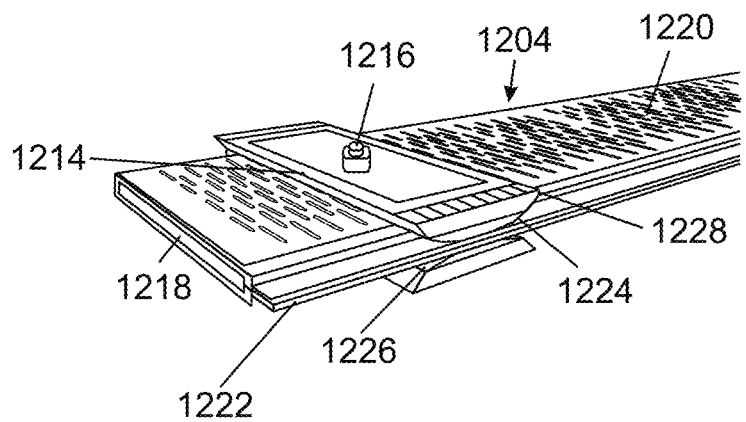
Figure 12D:
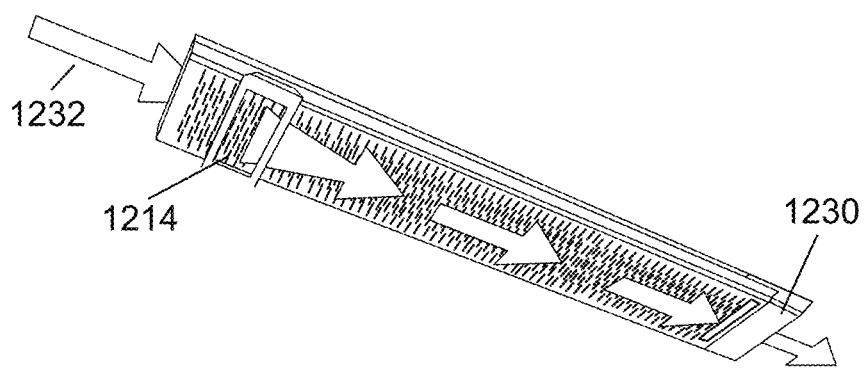
Figure 12E:
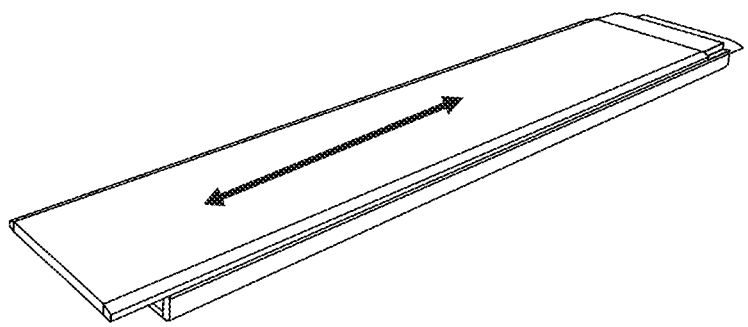

FIG. 12A is an isometric view of device 1200. In FIG. 12B, an outer casing 1202 of the device (shown in FIG. 12A) is not shown so as to expose the underneath structure. In FIG. 12C, a top layer 1206 of the device is not shown so as to expose cartridge 1204. FIG. 12D is a bottom view of the device. FIG. 12E illustrates an example for a loading mechanism of the device, according to some embodiments.

In some embodiments, top layer 1206 shown in FIG. 12B comprises a longitudinal slit 1208, optionally extending between a proximal end 1210 and a distal end 1212 of the device. In some embodiments, layer 1206 is made of a flexible material, such as silicone and/or rubber.

In some embodiments, an element configured to direct airflow and/or to apply electricity to the cartridge is provided. In some embodiments, for example as shown herein, the element is configured as a movable cart 1214, configured to be at least partially seated within slit 1208. Optionally, the movable cart comprises a nozzle 1216 (shown in FIG. 12C), extending through the slit to cartridge 1204, for directing airflow to a respective portion of the cartridge. In some embodiments, nozzle 1216 snuggly-fits within layer 1206 such that the material of layer 1206 seals the area around the nozzle, ensuring that most (such as 80%, 90%, 95% of the flow) or all of the flow passes through the nozzle.

In some embodiments, for example as shown in FIG. 12C, cart 1214 comprises electrodes 1224 and 1226 configured to apply a current to the cartridge.

Optionally, the electrodes are configured along the side edges of cart 1214.

In some embodiments, cart 1214 is moved manually, for example by sliding an outer cover of the device, as shown for example in FIG. 12E. Additionally or alternatively, cart 1214 is moved along cartridge automatically.

In some embodiments, for example as shown herein, cartridge 1204 comprises source material 1218 (such as tobacco and/or *cannabis*) in contact with a cover which may function as a heating element and/or as a sealant of the source material. In this example, the source material is caged in a perforated foil 1220. In some embodiments, for example as shown herein, cartridge 1204 is shaped as an elongated strip.

Alternatively, cartridge 1204 may comprise other configurations, such as a cylindrical configuration.

In some embodiments, cartridge 1204 comprises an insulating element, for example in the form of a longitudinally extending scaffold 1222, shown in FIG. 12C. Optionally, the insulating element is configured to separate between electrodes 1224 and 1226, so that current can be applied to a cartridge section currently positioned in contact with the cart.

In some embodiments, cartridge 1204 comprises a ratchet mechanism 1228 for advancing the cart in a single direction, for example a distal to proximal direction.

In some embodiments, in use, air 1232 flows into the device (for example upon suction induced by inhalation of a user) through distal end 1212, as shown in FIG. 12D. The flow of air is directed through nozzle 1216 to and through the source material enclosed within the cartridge segment being heated by the cart. Active substance imbued air 1234 exiting the cartridge flows along a bottom side of the cartridge, advancing into mouthpiece sheath 1230 to be delivered to the user.

In some embodiments, a wall opposite the bottom wall of the cartridge (not shown herein. Optionally, it is an internal face of the housing) comprises a cover or seal, for example comprising a non-perforated foil, for preventing the active substance imbued air from escaping.

In some embodiments mouthpiece sheath 1230 comprises a foil. In some embodiments, mouthpiece sheath comprises a heat resistant and/or electrically insulating lining.

In some embodiments, mouthpiece component 1230 (in this example in the form of a sheath) and/or cartridge 1204 and/or a battery and/or a flow conduit (such as between a bottom of the cartridge and an inner wall of the housing) are disposable and can be replaced.

In some embodiments, the device may be configured provide a smoke effect during use, for example by allowing vapor to escape the device. Optionally, the vapor originates from the source material being heated and/or from an added substance, for example propylene glycol (PG) and/or vegetable glycerine (VG).

In some embodiments, in order to provide an electronic cigarette which is equivalent to a conventional cigarette, the following may be used:

About 20 mg of tobacco may be heated per each delivery event. Optionally, the source material in total may be sufficient for 10-15 delivery events, each delivery event including, for example, a single inhalation. Optionally, the source material is shaped as a 0.5 mm thick strip and/or other structure. Optionally, the source material is covered by perforated foil sheets contacting the top and bottom surfaces of the strip.

In some embodiments, a power source in the form of a battery or a hybrid of a super capacitor and battery are used to apply electricity to each 20 mg section of source material. Optionally, the power source is configured to supply sufficient energy for a single e-cigarette. Alternatively, the power source is configured to supply energy sufficient for a plurality of e-cigarettes. In an example, a battery is configured to provide at least 4 Watt, at least 3 Watt, at least 6 Watt or intermediate, higher or lower power per mg of tobacco heated. Optionally, the battery is rechargeable. Optionally, the battery is disposable. Examples of commercially available batteries suitable for use in a device for example as described herein may include:

a. LiPo—Lithium polymer; a battery pack having 2 cells in a row may be used. A suitable cell for example is a SLPB503435H4 manufactured by KoKam;

b. Nanophosphate high power LiOn cell ANR26650 manufactured by A123; and c. Hybrid of super capacitor and a lithium ion battery. The super capacitor provides energy to the cartridge in a burst mode, while the battery charges the capacitor between uses. A suitable super capacitor example is a maxwell BCAP10350.

In another example, a 20 mg mix of ground tobacco and *cannabis* floss may be used. In some embodiments, a single dose consists of ground plant material weighing between 10 mg-50 mg. Optionally, this dose is flattened such that its width perpendicularly to a heating element is between 0.5-1.5 mm. Some non-limiting examples include 20-40 mg of tobacco and/or *cannabis* and a mix of 15 mg of tobacco and 25 mg of cinnamon each of which may be vaporized for example at 265° C.

In some embodiments, an amount of active substance delivered to a user from source material of a single section is equivalent to an amount of active substance inhaled in a single inhalation when smoking a conventional cigarette, for example comprising between 50-150 micrograms nicotine.

Optionally, the amount varies in accordance with the concentration of the active substance in the source material and the extraction efficiency of the device (calculated in accordance with the amount of source material and the amount of active substance delivered), which may be between, for example, between 10% and 85%, or between 30% and 80%, or between 40% and 75%, such as 40%, 60%, 75% or intermediate, higher or lower efficiencies. For example, at 50% extraction efficiency, each section may hold between 100-300 microgram nicotine. In embodiments in which the device corresponds to a conventional cigarette which can be smoked at about 10-12 puffs, the device may hold a total of between 1-3.6 milligram nicotine. As nicotine content may vary between different tobacco strains, the amount of tobacco may vary. In a first example, tobacco holds about 25 mg nicotine per 1 gr of tobacco. In a second example, tobacco holds about 15 mg nicotine per 1 gram of tobacco.

In some embodiments, the amount of source material is equivalent to one or more conventional cigarettes. In an example, a single cartridge comprises source material sufficient for between 50-120 delivery events (delivered through 50-120 inhalations or a larger number of inhalations), corresponding to about 5-10 cigarettes, depending on nicotine content. For example, for tobacco having the aforesaid lower nicotine content, the total amount of source material may include between 1.25-2.5 grams tobacco. For tobacco having the higher nicotine content, the total amount of source material may include between 125-250 milligrams tobacco. Optionally, when tobacco having a relatively high nicotine content is used, the total amount in the cartridge may correspond to a larger number of cigarettes.

In some embodiments, the source material comprises about 1-10%, 3-7%, 5-8%, 10-20% or intermediate, larger or smaller range of nicotine.

In some embodiments, each source material section comprises at least 5, 10-20, 11, 12, 13, 14, 15, 16, 17, 18, 19, 20, 30, 40, 50 mg or intermediate, larger or smaller amount of tobacco.

In an example, each source material section comprises 15 mg of organic material such as tobacco or *cannabis*. Optionally in such case a cartridge comprising 10 source material sections includes a total of 150 mg organic material.

It is noted that materials other than tobacco may be used, and the amounts described herein may be applicable to other plant materials. Alternatively, when a synthetic and/or extracted and/or purified substance is used, even higher concentrations of the active substance may be provided, thereby possibly providing more delivery events per a single cartridge of source material.

FIGS. 13A-B illustrate a device 1308 for example as shown in FIGS. 12A-E, comprising a use progress indicator, according to some embodiments.

In some embodiments, the device comprises a use progress indicator, configured to indicate one or more of: an amount of source material used, an amount of source material remaining, that all source material has been consumed or is about to be consumed, and/or other indications.

As used herein, source material (or an amount of source material) is deemed to have been consumed at such time when the device already used the source material (e.g. by heating it and/or by allowing airflow therethrough) and/or when the device is configured not to use the source material (even if no active substance was inhaled therefrom). Optionally the signal indicates that a given portion of source material has been consumed. For example, if a device is loaded with source material that comprises tobacco or nicotine which is intended to replace a plurality of cigarettes, an indication may be provided separately to indicate that an amount of source material correlating to a single cigarette was consumed, thereby allowing a user to pace the rate of use.

In some embodiments, the indicator is configured to provide a visual and/or audible and/or tactile and/or sensible indication to the user. In an example, the indicator comprises a scent in the source material that is released only during the last delivery event and/or last 2-3 inhalations. In another example, the indicator comprises a light tube. Optionally, heat causes deformation of the tube material so that light conductance changes (for example a transparent plastic becomes milky-colored due to heat), indicating use progress to a user. In some embodiments, the indicator is configured to indicate (e.g. via a change in color and/or a change in light intensity) the remainder of active substance in the currently provided dose and/or currently used source material section. In an example, as a user addresses a given source material section, an indicator light turn on. The indicator light dims or blinks as the user inhales (by one or more inhalations) for indicating an estimated amount of active substance left in the section. In an example, a high concentration and/or large remaining amount of active substance correlates with one or more of: a high light intensity, which diminishes during use, a high blinking rate which slows down during use, a gradual color change of the indicator (e.g. from red to black). Optionally, upon loading of the following dose, the indicator returns to its pre-inhalation condition, for example the light travels along the indicator, returning the lighting status to full brightness.

In some embodiments, the amount of active substance left in a section is calculated based on one or more of: the amount and/or concentration of active substance in that section, the amount of source material in that section, the amount of inhalations of the user in which active substance(s) were extracted from that section, flow rate of inhalation, a suction force produced by the inhalation, a time period during which that section was heated; a temperature that the source material was heated to, and/or a rate of airflow passing through that section.

In some embodiments, the indicator light is initially turned on at low brightness and/or at a given color, and brightness is increased and/or the color changes as inhalation continues and/or in response to suction force produced by inhalation. Optionally, the light returns to its low intensity state and/or to the baseline color when inhalation terminates.

In some embodiments, for example as shown in FIGS. 13A-B, indicator 1300 comprises a light and/or a color mark. Optionally, indicator 1300 is configured to move in unison with a loading mechanism of the device, for example move along with a cart for example as shown in FIGS. 12A-E (1214). Optionally, indicator moves from a distal end 1302 of the device towards a proximal end 1304 where mouthpiece 1306 is positioned. Optionally, the device housing comprises informative marking (not shown) corresponding to one or more positions of indicator 1300. In some embodiments, the physical position of the indicator indicates the remaining source material sections and/or the used source material sections.

FIG. 14 is a flowchart of a general method of delivering to a user at least one substance released from a source material, according to some embodiments of the invention.

In some embodiments, one or more source material sections out of a plurality of source material sections are selected for use (1400). Optionally, the one or more sections are selected automatically by a controller of the inhaler device. Additionally or alternatively, the one or more sections are selected by a user, for example using a mechanical and/or electrical actuator (e.g. a dial, slider, switch, and/or other). Optionally, the sections are selected sequentially in an order determined by their spatial arrangement within the device.

In some embodiments, different source material sections comprise different types of materials. Optionally, different types of plant materials are used, for example including tobacco, *cannabis*, and/or other plant materials such as listed hereinabove.

In some embodiments, different source material sections comprise different compositions of substances.

In some embodiments, different source material sections comprise different amounts of active substances, e.g. nicotine, THC and/or other cannabinoids, and/or alkaloids and/or other active substances including for example 1,2,3,4-Tetrahydroisoquinolines, Anabasine, Anatabine, Cotinine, Myosmine, Nicotrine, Norcotinine, and/or Nornicotine.

In some embodiments, source materials sections are spatially arranged in the cartridge according to their content. For example, a series of source material sections each comprising a different amount of active substance is arranged in a manner in which the amount of active substance varies along the cartridge (e.g. decreases and/or increases along the cartridge). Optionally the variation relates to the composition of active substances, such as for example to an amount of added scent and/or flavor imparting active substances in addition to a fixed or varying amount of another active substance (e.g. nicotine, THC and/or any other alkaloid or cannabinoid). Alternatively, the amount of active substance in each of a plurality of source material sections is constant.

In some embodiments, a timing and/or order of delivery of different materials and/or different amounts of active substances to a user is controlled by a spatial arrangement of the different source material sections relative to each other. Optionally, the sections are used according to their spatial arrangement. Alternatively, the sections are used in an order that does not depend on their spatial arrangement. Optionally, the sections are used in an order determined by the user. Optionally, a controller sets an order in which the sections are used according to input provided by and/or obtained from the user. Alternatively, the sections are used in a pre-determined order.

In some embodiments, a single section is divided into a plurality of subsections, for example 2, 3, 5, 10 subsections. Optionally, only a portion of the subsections is selected for use.

In some embodiments, a subset of a plurality of source materials is selected. Optionally, at each inhalation and/or at each usage session of the device (such as a usage session including a plurality of inhalations), a different subset of sections is selected for use.

In some embodiments, an airflow path is created between the one or more selected source material sections and an output to the user (1402). In some embodiments, creating of an airflow path comprises modifying a state of an existing path that leads to the selected section, from a state in which flow of air is not permitted through the path to a state in which at least some flow of air is permitted through the path. In some embodiments, modifying comprises forming fluid communication between the selected source material section and the user, for example by unblocking of the path, aligning of misaligned portions of the path, switching of a valve and/or other actions suitable to provide for air to flow to and through the source material of the selected section, into the path, and to the user.

In some embodiments, once airflow is permitted through the source material, at least one active substance is released from the source material (1404). Optionally, the active substance is released by vaporization of the source material. In some embodiments, a heating element associated with the source material section is activated to heat the source material of the selected section, for example by electrically coupling the heating element to a power source.

In some embodiments, heating of the source material and creating of the airflow path are coordinated. Optionally, heating is initiated before allowing airflow through (for example up to 2 minutes, 1 minute, 30 seconds, 25 seconds, 20 seconds, 15 seconds, 10 seconds, 5 seconds, 2 seconds and/or intermediate, longer or shorter time periods before allowing airflow through. Optionally, heating is terminated before creating the airflow path.

Alternatively, heating is initiated after creating the airflow path, for example 1 msec, 10 msec, 500 msec, 1 second, 5 seconds, 10 seconds or less after an airflow path is defined.

Optionally, heating is initiated before an airflow path is created and is increased after an airflow path is created.

Additionally or alternatively, heating is initiated or increased in response to user action, for example in response to inhalation through the device.

In some embodiments, creating of an airflow path (such as by unblocking the airflow path) and timing of heating of the source material are coordinated by a controller of the inhaler device. Optionally, the controller is programmed with one or more protocols defined in accordance with one or more of: the type(s) of source material used; the type(s) of active substance extracted; the user profile and needs and/or other.

In some embodiments, a timing of heating is determined according to sensing of airflow, for example in response to an indication received from a flow rate sensor, a pressure sensor, and/or other flow related indication. Optionally, heating is initiated or increased automatically in response to a flow related indication received from one or more sensors. Additionally or alternatively, heating is initiated or increased by manual operation of the device by a user.

In some embodiments, the released (e.g. vaporized) substance is then delivered to the user (1406). Optionally, air drawn into the inhaler, optionally in response to inhalation of the user, passes through the source material of the selected section, into the airflow path that was formed, and to the user, for example via a mouthpiece component. In some embodiments, the flow of air reaching the user comprises ambient air that was drawn into the inhaler and imbued with vapors of the released active substance. Optionally, the airflow path is isolated such that once air passed through a section it can exit the device solely through the mouthpiece component. Optionally, the substance-containing airflow can exit the device only as long as inhalation is performed by a user.

In some embodiments, following use of one or more source material sections, their associated airflow paths are then closed. Alternatively, air that passes by the used source material sections (for example via an airflow path of a source material section currently being used) may contact the used source material.

In some embodiments, a cartridge comprising a plurality of source material sections and optionally at least a portion of their associated airflow paths is provided, the cartridge being configured to be received within and/or otherwise operably coupled to the inhaler device. In some embodiments, the cartridge comprises an output to a user, for example in the form of a mouthpiece component or a mouthpiece. In an example, a pipe-like mouthpiece is used, optionally narrowing down in a direction of user, to facilitate suction. In some embodiments, the cartridge comprises an actuator configured for unblocking respective airflow paths of the one or more selected source material sections and/or configured for actuating heating of the source material of the one or more selected sections.

FIGS. 15A-B schematically illustrate selectively unblocking an airflow path associated with a selected source material section, according to some embodiments.

In some embodiments, for example as shown in FIG. 15A, a plurality of source material sections 1500, 1502, 1504 are provided. Optionally, each source material section is associated with a respective airflow path 1506, 1508, 1510, extending between the source material section and an output 1512 to the user 1514. Optionally, the plurality of airflow paths join together to form a single airflow path before reaching output 1512. The plurality of airflow paths in FIG. 15A are shown in a blocked state which does not allow flow through.

In some embodiments, during use, for example as shown in FIG. 15B, at least one airflow path such as 1506 is modified to allow for flow of air 1516 through. Optionally, modifying comprises unblocking the airflow path, for example by moving a blocking element 1518 to a position in which it does not fully block the path. In some embodiments, for example following use of the source material section, airflow path 1506 can be blocked again, for example by moving blocking element 1518 to a blocking position.

In some embodiments, each source material section is associated with a heating element configured for heating at least a part of the source material within the section. In some embodiments, the heating element is in contact and/or in sufficient proximity to the source material to provide for heating the source material to a temperature sufficient for vaporizing at least one active substance from the source material. In an example, the heating element comprises a mesh which at least partially contacts the material. Optionally, the mesh defines at least one wall 1520 of the source material section. Optionally, the mesh comprises openings through which air is allowed to flow to and/or through the source material. Heating elements for example as described hereinabove may be used in addition or alternatively to the mesh.

For example, in some embodiments, the heating element may be constructed of or include one or more of the following electrically resistive materials: semiconductors such as doped ceramics, electrically "conductive" ceramics (such as, for example, molybdenum disilicide), carbon, graphite, metals, metal alloys and composite materials made of a ceramic material and a metallic material. Such composite materials may comprise doped or undoped ceramics. Examples of suitable doped ceramics include doped silicon carbides. Examples of suitable metals include titanium, zirconium, tantalum and metals from the platinum group. Examples of suitable metal alloys include stainless steel, nickel-, cobalt-, chromium-, aluminium-titanium-zirconium-, hafnium-, niobium-, molybdenum-, tantalum-, tungsten-, tin-, gallium-, manganese- and iron-containing alloys, and super-alloys based on nickel, iron, cobalt, stainless steel, Timetal® and iron-manganese-aluminium based alloys. Other materials may include silver, platinum, copper, nickel and palladium.

In some embodiments, the plurality of source material sections are separated from each other by an air sealed barrier, for example comprising a wall 1522. Optionally, the air sealed barrier can be removed or shifted, for example to enable access to two source material sections together.

In some embodiments, a source material section such as 1500 is stationary with respect to a housing 1524 of the device. Optionally, there is no relative movement between the source material section and heating element 1520; no relative movement between the source material section and its associated airflow path 1506; and/or no relative movement between the source material section and one or more structural elements of the device, such as output 1512 (e.g. a mouthpiece component).

In some embodiments, a layer of source material contained within each section is no more than 1 mm thick, no more than 0.5 mm thick, no more than 2 mm thick, no more than 5 mm thick or intermediate, higher or lower thicknesses. For example the layer may be between 0.5-5 mm, or between 0.5-2 mm, or between 0.5-1.5 mm along the path of airflow through the material.

Figure 16A:
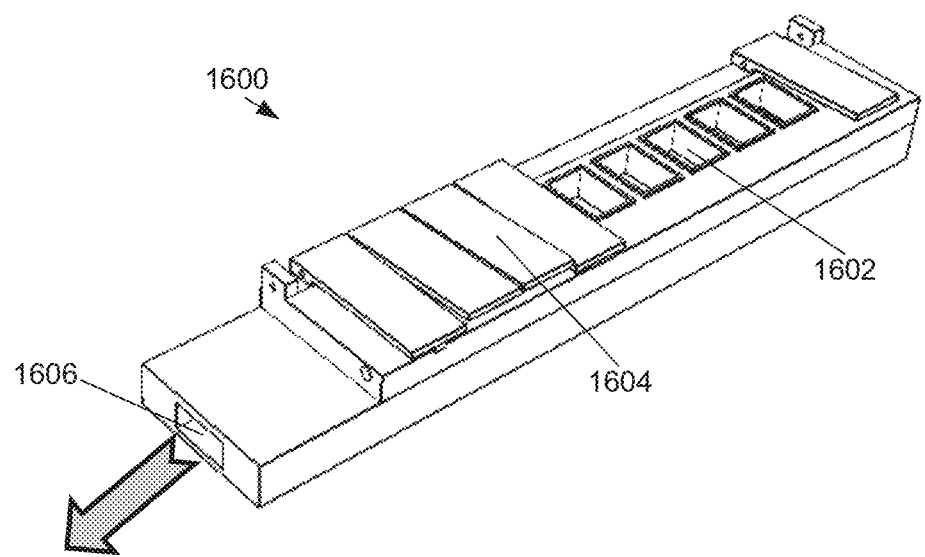
FIGS. 16A-B illustrate an arrangement of source material sections structured to provide for separately accessing each of the plurality of source material sections, according to some embodiments of the invention.
Figure 16B:
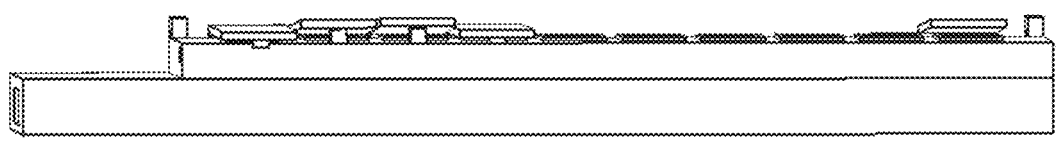

FIGS. 16A-B are an isometric view (16A) and a side view (16B) of an arrangement of source material sections structured to provide for separately accessing each of the plurality of source material sections, according to some embodiments.

In some embodiments, arrangement 1600 comprises an array of source material sections 1602. Optionally, the sections are linearly aligned with respect to each other, for example as shown herein. It is noted that other arrangements and/or spatial distributions of the plurality of sections are also contemplated. In some embodiments, each section 1602 can be accessed by lifting, shifting and/or otherwise moving a cover 1604 that blocks passage of air to and through and source material of the section. In some embodiments, movement of cover 1604 is actuated magnetically, manually, and/or electrically. In some embodiments, cover 1604 is pivotally coupled to a hinge.

In some embodiments, air that flows into an opened source material section passes through the source material and into a conduit (an opening of which is shown at 1606) to be delivered to a user. Optionally, the conduit is a shared conduit for the plurality of source material sections.

Figure 17A:
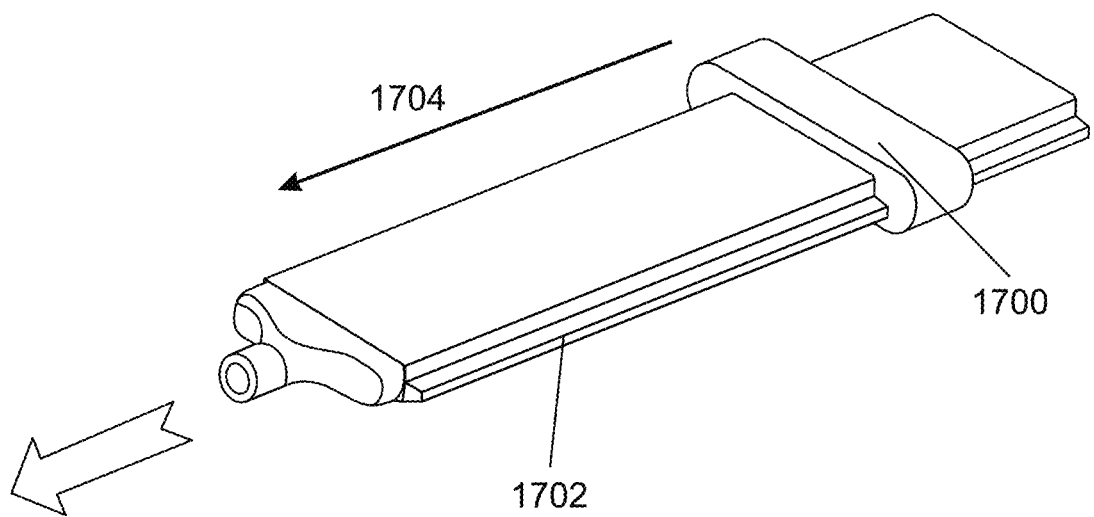
FIGS. 17A-B illustrate a slidable actuator configured for unblocking at least one airflow path associated with at least one source material section and/or for activating a heating element associated with the at least one source material section, according to some embodiments of the invention.
Figure 17B:
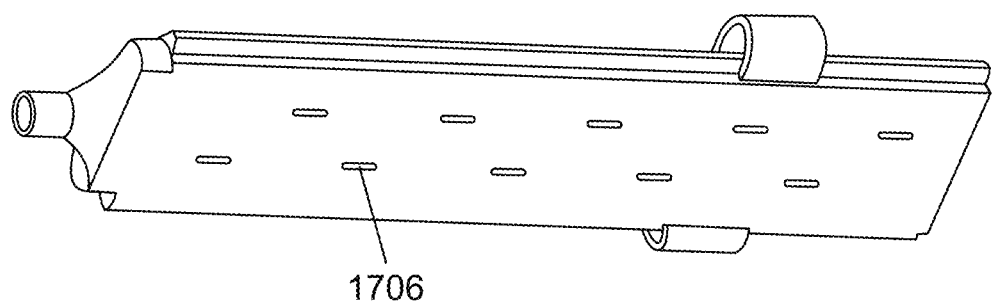

FIGS. 17A-B illustrate a slidable actuator 1700 configured for unblocking at least one airflow path associated with at least one source material section and/or for activating a heating element associated with the at least one source material section, according to some embodiments of the invention.

In some embodiments, actuator 1700 is moved along housing 1702, for example slid along a long axis of the housing such as in the direction illustrated by arrow 1704, to provide for accessing one or more selected source material sections underlying housing 1702. In some embodiments, actuator 1700 is configured to shift a cover (such as cover 1604 as described hereinabove) of an underlying source material section.

In some embodiments, actuator 1700 is configured to activate a heating element associated with a source material section, for example by electrically coupling the heating element (such as an electrically conductive mesh) to a power source, e.g. a battery.

Additionally or alternatively, in some embodiments, electrical coupling is actuated in response to inhalation.

Optionally, an electrical circuit is closed in response to sensing of a flow related parameter (e.g. pressure or a change in pressure). Additionally or alternatively, an electrical circuit is closed by movement of a flap, valve and/or other mechanical element that shifts in response to airflow. In some embodiments, inhalation causes electrical coupling and heating to commence by changing position of a mechanical element, such as a leaflet or a spring to close an electrical circuit when moved by sufficient airflow. Other examples for such mechanical elements include bi-metal switches that are responsive to airflow, an electro-mechanical dynamo that generates power as a result of flow and/or other suitable devices.

In some embodiments inhalation acts as a trigger for a physical and/or electronic sensor such as but not limited to conductivity of the lips, temperature of the lips, change in pressure due to inhalation, characteristic accelerations caused by motion with reference to the earth's gravity, proximity sensors and/or light sensors. In some embodiments, sensing of inhalation is performed by a mechanical element, such as a leaflet or a spring that changes position to close an electrical circuit when moved by sufficient airflow. Optionally, mechanical sensing of airflow is performed in conjunction with electrical and/or electro-mechanical elements such as conductivity sensors and/or bending sensors. Other examples include bi-metal switches that are responsive to airflow, an electro-mechanical dynamo that generates power as a result of flow and/or other suitable devices and/or sensors.

In some embodiments the actuator is used to connect electrical circuitry to perform aforementioned coupling such as via pogo-pins, leaflet connections, direct galvanic connection and/or others.

In some embodiments the electrical heater is actuated based on determining a change in airflow for example as described in WO2013060784, which is incorporated herein by reference. For example, any sensor which can detect airflow may be used. The sensor may be an electro-mechanical device. Alternatively, the sensor may be any of: a mechanical device, an optical device, an opto-mechanical device, a micro electro mechanical systems (MEMS) based sensor and an acoustic sensor. The sensor can be a thermal conductive flow sensor, a pressure sensor, an anemometer. Optionally, the sensor may be able to not only detect airflow but also be able to measure it. The sensor may be configured to deliver an analogue electrical signal or digital information that is representative of an amplitude of the airflow.

In some embodiments, movement of actuator 1700 is performed manually (e.g. by a user). In some embodiments, a user advances actuator 1700 prior to and/or during usage of the device. A potential advantage of a user controlled actuator may include allowing the user to control the rate and/or duration and/or amount or active substance delivered.

Alternatively, movement of actuator 1700 is performed automatically, for example according to a predefined protocol.

FIG. 17A illustrates a first side of the device across which actuator 1700 is advanced; FIG. 17B illustrates a second, opposite side of the device, comprising a plurality of slots 1706 through which air enters the device. Air entering the device may enter source material sections upon unblocking of associated airflow paths (not shown in this example).

FIGS. 18A-D are various structural features of an actuator for example as described in FIGS. 17A-B, according to some embodiments.

Figure 18A:
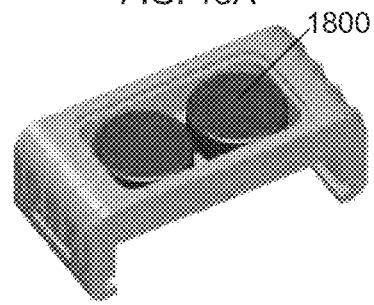
FIGS. 18A-D show various structural features of an actuator for example as described in FIGS. 17A-B, according to some embodiments of the invention.
Figure 18B:
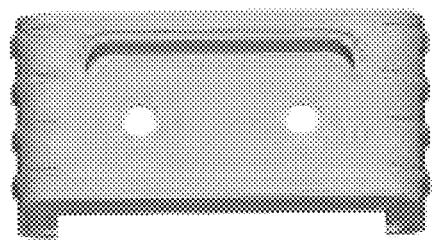

In some embodiments, the actuator is configured for shifting a cover of a source material section using magnetic attraction. Optionally, for example as shown in FIG. 18A, the actuator comprises one or more magnets 1800 sized, positioned and having sufficient magnetic force for shifting a magnetically attracted cover of a source material section. FIG. 18B shows the actuator structure without the magnets.

Figure 18C:
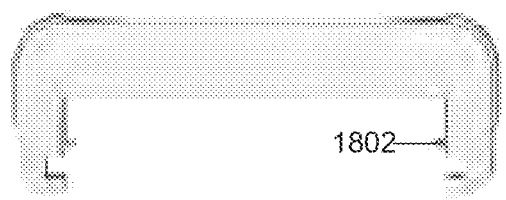

In some embodiments, for example as shown in FIG. 18C, the actuator comprises electrical connectors 1802 configured to close or become part of an electric circuit of a source material section when the actuator is in position. In some embodiments, closure of the electric circuit activates the heating element so as to heat the source material of the selected section. In some embodiments, the circuit can be closed only once the cover of the selected source material section is shifted. In some embodiments, the circuit can be closed only once airflow commences or is above a given threshold.

In some embodiments, the actuator is shaped and/or sized to be positioned over and optionally across a housing that encases the source material sections. In the example shown herein, the actuator comprises a rectangular profile sized to bridge across the housing. It is noted that the actuator may comprise any other forms suitable for engaging a blocking element of a source material section upon advancement and/or other movement of the actuator, for unblocking the element.

Figure 18D:
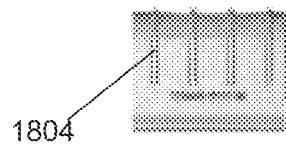

In some embodiments, for example as shown in FIG. 18D, the actuator comprises one or more structural elements shaped for facilitating manual grip of the actuator, such as ribs 1804.

Figure 19A:
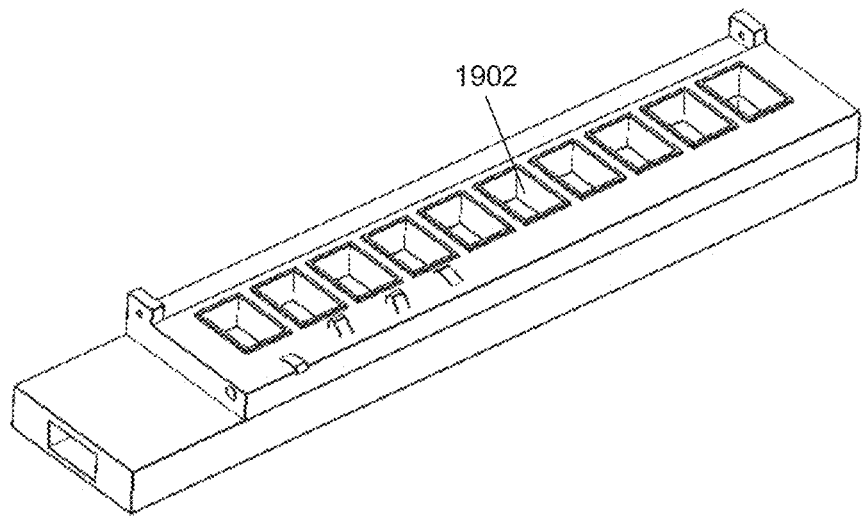
FIGS. 19A-B illustrate a camshaft mechanism for selectively accessing source material sections in a serial manner, according to some embodiments of the invention.
Figure 19B:
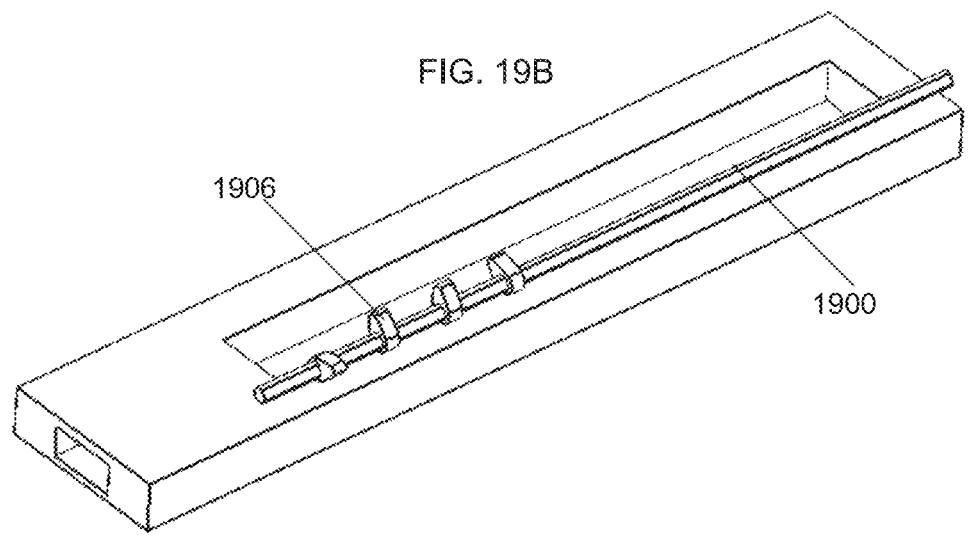

FIGS. 19A-B illustrate a camshaft mechanism for using a plurality of source material sections in a serial manner, according to some embodiments of the invention. In some embodiments, a camshaft 1900 extends along at least a portion of the arrayed source material sections 1902 at a position suitable for actuating shifting of the covers of the source material sections (covers are not shown). In some embodiments, lobes 1906 of the camshaft extend to engage the covers so that upon rotation of the camshaft the covers are lifted one after the other by the lobes, thereby allowing air to flow into and through the source material of the opened section.

Figure 20:
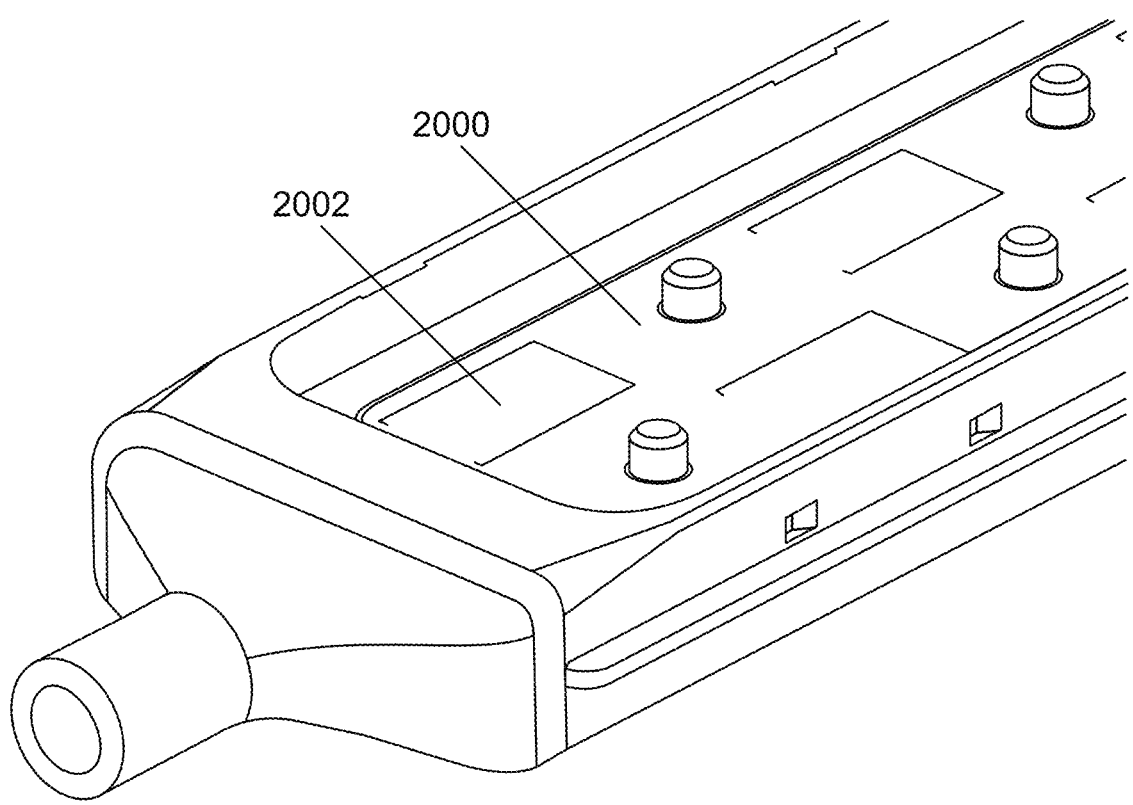
FIG. 20 illustrates deformable access regions for selectively accessing one or more source material sections, according to some embodiments of the invention.

FIG. 20 illustrates deformable access regions for selectively accessing one or more source material sections, according to some embodiments. In some embodiments, a panel 2000 covers an array of source material sections (not shown). In some embodiments, the panel comprises a plurality of access regions 2002 at respective locations of the source material sections. In an example, an access region 2002 is located directly above a source material section. In some embodiments, an access region 2002 comprises a region that is less sturdy than surrounding panel material, so that it can be peeled, penetrated and/or otherwise deformed for allowing air through. In some embodiments, an access region comprises a perforated and/or etched layer.

In some embodiments, the access region is formed of and/or comprises magnetic material so that it can be peeled in response to pulling of a magnet, such as by advancing of a magnetic actuator for example as described herein above. Optionally, when magnetic force is no longer applied (for example when the actuator is further advanced), the access region returns back to an initial closed position.

In some embodiments, an access region comprises one or more of: magnetic materials, stainless steel, iron sheets, nickel, ferrous foils and/or other.

Figure 21A:
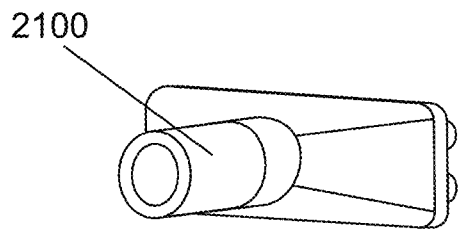
FIGS. 21A-C illustrate: a mouthpiece (21A and 21B) and a frame for use with an array of source material sections (21C), according to some embodiments of the invention.
Figure 21B:
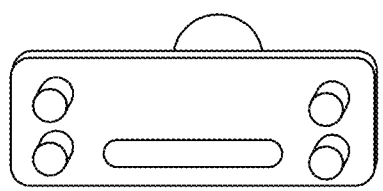
Figure 21C:
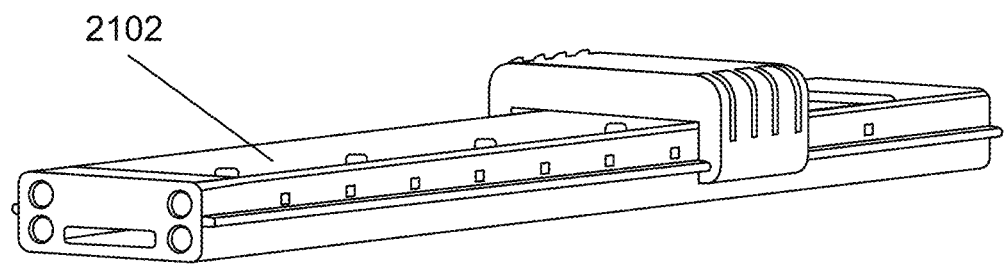

FIGS. 21A-C illustrate a mouthpiece for use with an array of source material sections, according to some embodiments. In some embodiments, a mouthpiece 2100 (shown in a front view in FIG. 21A and in a back view in FIG. 21B) is configured to attach to a frame 2102 (shown in FIG. 21C) of the array of source material sections (not shown herein). Optionally, mouthpiece 2100 is removably attached to frame 2102, for example that it can be washed and placed back. Additionally or alternatively, mouthpiece 2100 is disposable.

In some embodiments, a sealing for example in the form of an O-ring (not shown) is provided at the mouthpiece-frame attachment, to ensure fluid communication.

Figure 22:
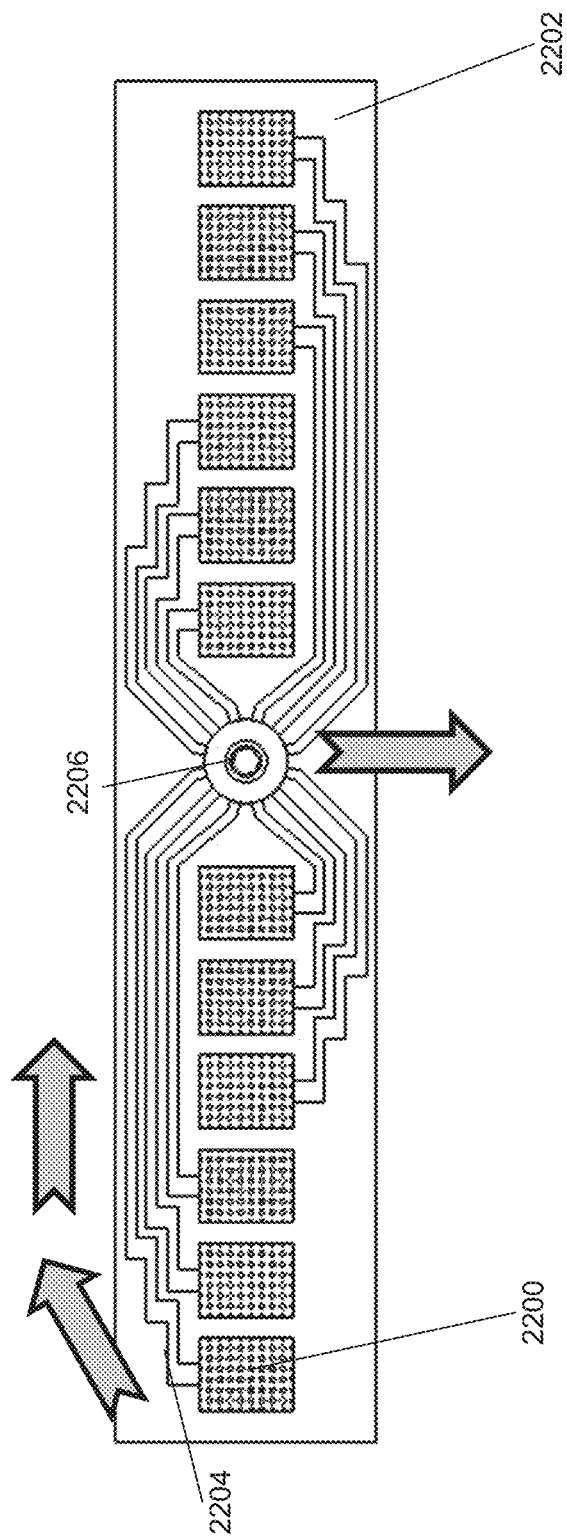
FIG. 22 is a cross section view of an arrangement of a plurality of source material sections and dedicated airflow conduits, according to some embodiments of the invention.

FIG. 22 is a cross section view of an arrangement of a plurality of source material sections and dedicated airflow conduits, according to some embodiments.

In some embodiments, source material is contained within a plurality of slots 2200 defined in a substrate 2202. In some embodiments, one or more airflow paths such as conduit 2204 extend from slot 2200 distally to a central airflow exit 2206.

In some embodiments, an actuator for example in the form of a rotary switch as further described hereinbelow is positioned at airflow exit 2206. Optionally, conduit 2204 is unblocked to allow for airflow through the conduit and to and through the source material of a selected slot by aligning an opening of the rotary switch with a distal opening of conduit 2204.

In some embodiments, the switch concomitantly closes an electrical circuit of the selected source material slot so as to actuate heating of the source material. Additionally or alternatively, in some embodiments, electrical coupling is actuated in response to inhalation. Optionally, an electrical circuit is closed in response to sensing of a flow related parameter (e.g. pressure, for example pressure or a change in pressure sensed in response to inhalation of a user through the device). Optionally, closure of the electrical circuit initiates heating. Optionally, the electrical circuit is closed as a mechanical result of airflow.

In some embodiments, heating vaporizes the source material and air imbued with at least one active substance flows through airflow exit 2206 to be delivered to the user (such as via one or more additional conduits and a mouthpiece, not shown herein).

In some embodiments, substrate 2202 is a PCB comprising embedded circuitry associated with the source material slots. Optionally, the PCB is a flexible PCB. In some embodiments, substrate 2202 may include a stripboard and/or a free-from using adhesives (dead-bug construction). In some embodiments, substrate 2202 comprises materials such as heat resistant materials and/or inert materials such as Kapton, all-polyimide, mica foil and/or others.

Figure 23:
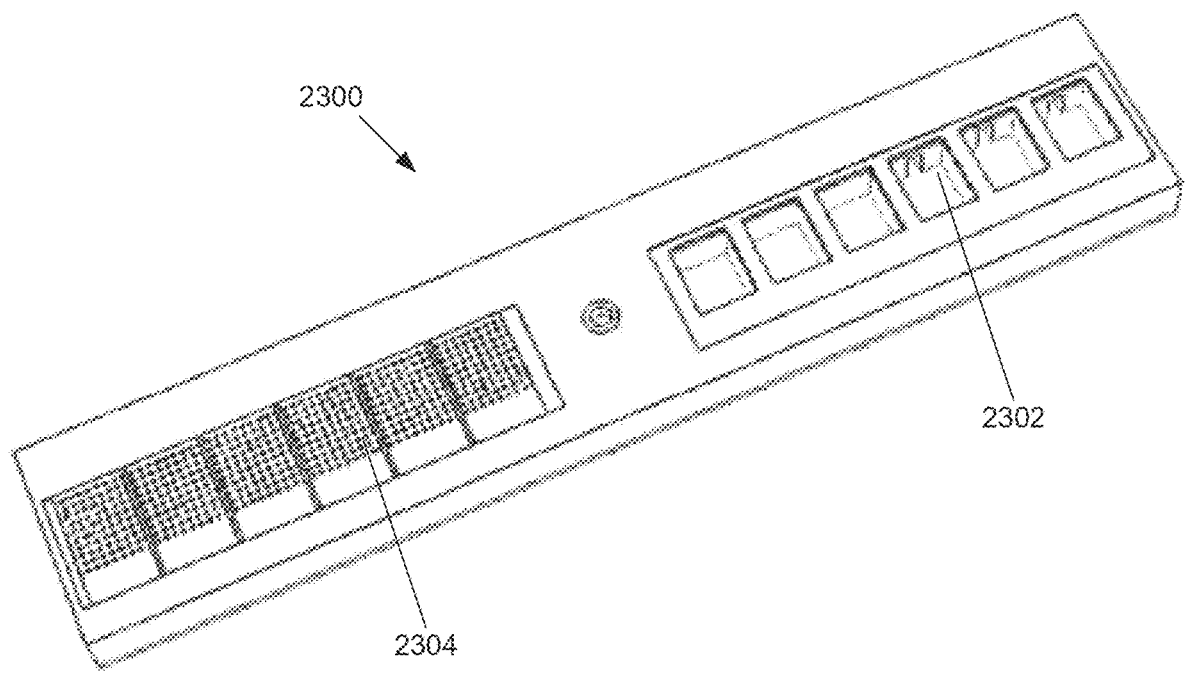
FIG. 23 is an outer view of an arrangement for example as shown in FIG. 22, according to some embodiments of the invention.

FIG. 23 is an outer view of an arrangement for example as shown in FIG. 22, according to some embodiments.

This figures shows a housing 2300 containing an arrangement for example as described in FIG. 22. For illustrative purposes, empty source material slots 2302 are shown on the right side of the housing, and slots 2304 covered by a mesh (optionally already loaded with source material) are shown on the left side of housing 2300.

Figure 24A:
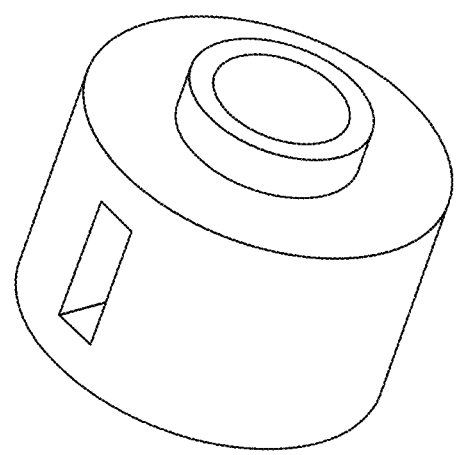
FIGS. 24A-B are examples of a rotatable actuator for use with an arrangement for example as shown in FIG. 22, according to some embodiments of the invention.
Figure 24B:
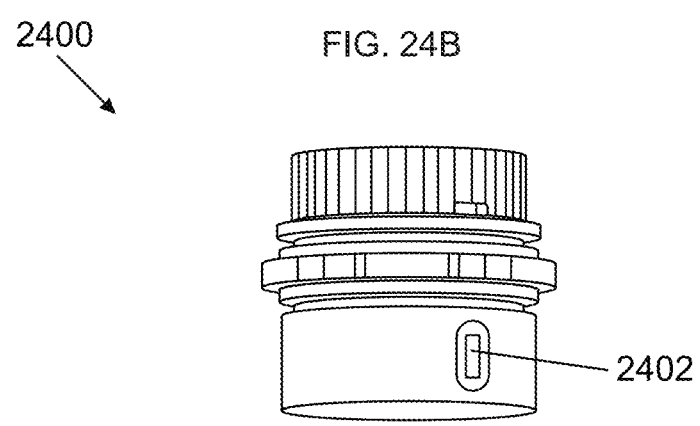

FIGS. 24A-B are examples of a rotatable actuator for use with an arrangement for example as shown in FIG. 22, according to some embodiments.

In some embodiments, a rotatable actuator 2400 comprises an orifice 2402 through which air can flow. Optionally, upon rotation of the actuator, orifice 2402 is aligned with a distal opening of an airflow conduit leading to a source material section (e.g. a source material slot as described hereinabove).

In some embodiments, the actuator comprises electrical connections positioned to close a circuit with the selected source material section. Optionally, the electrical connections comprise pogo pins and/or other spring loaded contacts suitable for establishing a temporary electrical connection with the circuitry of the selected source material slot.

Figure 25A:
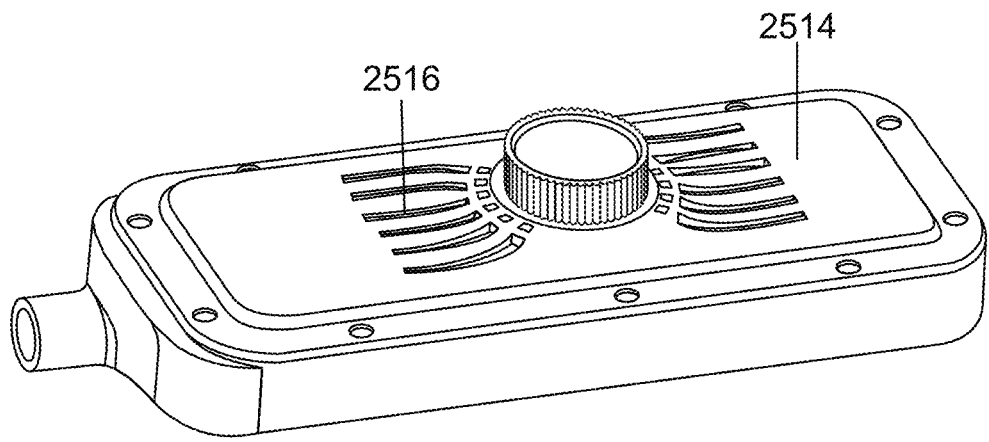
FIGS. 25A-C show a device comprising an arrangement for example as shown in FIG. 22, according to some embodiments of the invention.
Figure 25B:
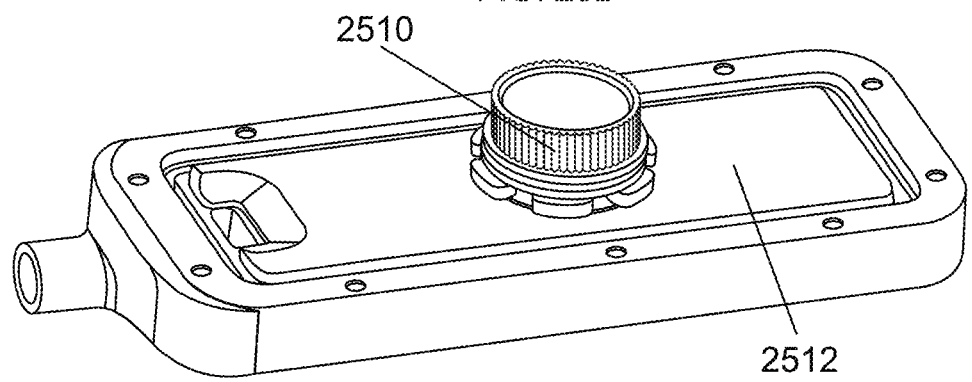
Figure 25C:
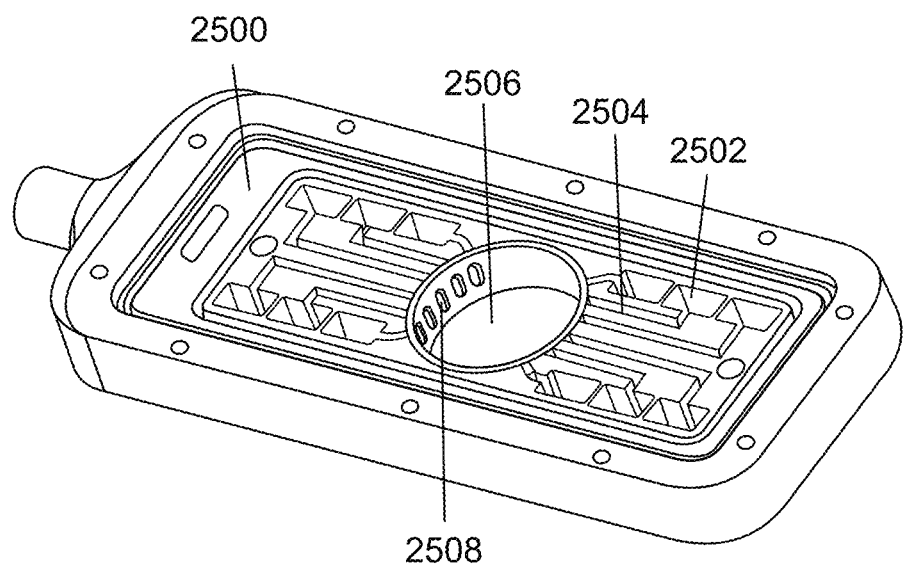

FIGS. 25A-C show a device comprising an arrangement, according to some embodiments, being similar to the one shown in FIG. 22.

At the cross section view of FIG. 25C, a substrate 2500 (e.g. a PCB) including a plurality of source material slots 2502 and their associated conduits 2504 can be observed. In this example, slots 2502 are arranged in a different geometrical pattern than that of FIG. 22. A central airflow exit 2506 comprising distal openings 2508 of the conduits according to some embodiments is shown without the rotatable actuator. FIG. 25B shows grip 2510 of the rotatable actuator protruding outwardly relative to substrate 2500, the actuator being positioned at airflow exit 2506. A cover 2512 is layered over substrate 2500 so as to block the openings of slots 2502, according to some embodiments, from at least one direction. In some embodiments, distal openings 2508 are blocked and selectively opened by an actuator such as a rotatable actuator 2400 for example as shown in FIGS. 24A-B.

FIG. 25A shows the fully assembled device, according to some embodiments. In some embodiments, an external housing 2514 comprises one or markings 2516 for indicating a position of the rotatable actuator 2510 to a user.

Figure 26:
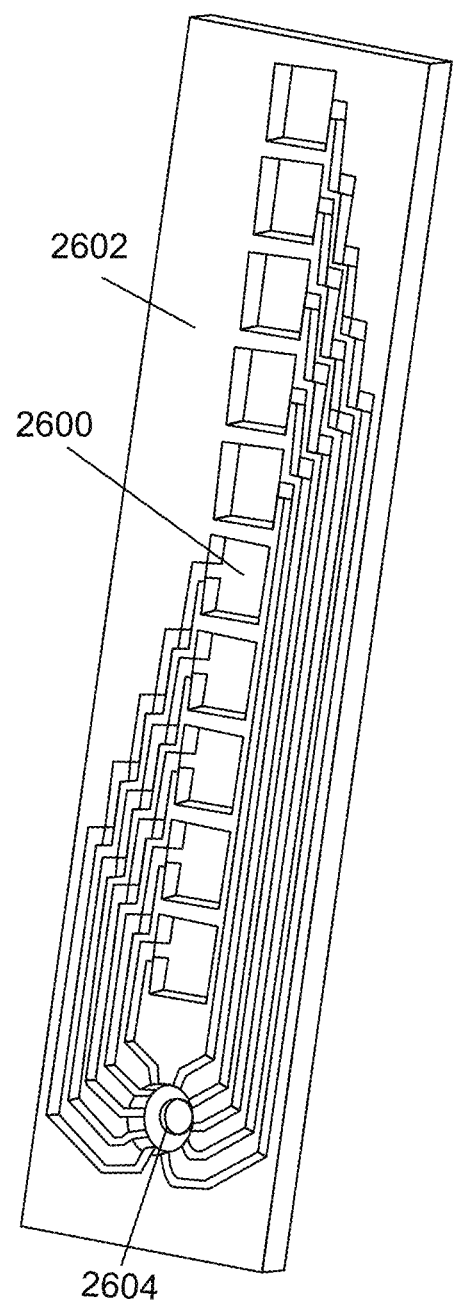
FIG. 26 illustrates an alternative arrangement of a plurality of source material sections and dedicated airflow conduits, according to some embodiments of the invention.

FIG. 26 illustrates an alternative arrangement of a plurality of source material sections and dedicated airflow conduits, according to some embodiments. In this example, all source material slots 2600 defined in substrate 2602 are linearly aligned with respect to each other. In some embodiments, for example as shown herein, airflow exit 2604 is located at a proximal and/or distal end of the substrate. Airflow conduits 2604 are shown to extend from their associated source material slots to airflow exit 2604.

Some embodiments may include more than one main airflow exit, for example 2, 3, 5 airflow exits.

Figure 27A:
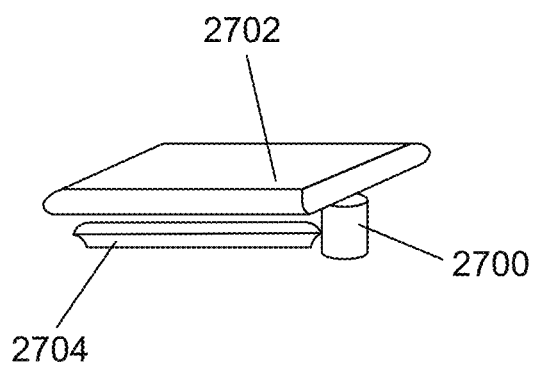
FIGS. 27A-C illustrate moving of a source material cover using a shape changing element, according to some embodiments of the invention.
Figure 27B:
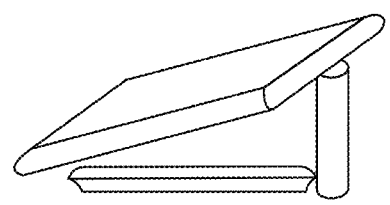
Figure 27C:
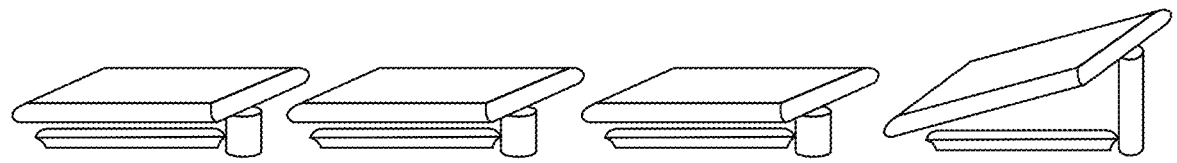

FIGS. 27A-C illustrate moving of a source material cover using a shape changing element, according to some embodiments of the invention.

In some embodiments, a shape changing element comprises one or more shape memory materials which deform in response to temperature change.

In some embodiments, a shape changing element such as transformable body 2700 is positioned to shift, lift and/or otherwise move a cover 2702 of a source material section so as to allow airflow through. In some embodiments, transformable body 2700 is configured to deform in response to a change in temperature, for example expand, bend and/or straighten in response to a rise in temperature. In some embodiments, transformable body 2700 is configured to return to its original shape in response to cooling. In some embodiments, transformable body 2700 is located adjacent and/or in contact with or at a location where it is designed to interact with a heating element 2704 of the source material section. Optionally, when heating element 2704 is activated, such as by closing an electrical circuit, transformable body 2700 expands in one or more directions to thereby push cover 2702 into a position in which airflow is allowed through the source material, for example as shown in FIG. 27B. In this example, transformable body 2700 extends longitudinally (i.e. along an axis substantially perpendicular to cover 2702 when cover 2702 is closed) in response to heating, thereby lifting at least a portion of cover 2702.

In some embodiments, a shape changing element is configured to move, bend, perforate, shift and/or otherwise affect at least a portion of a cover of a source material section. In some embodiments, a shape changing element comprises polyurethane foam, shape memory polyurethane, polymers, silicone, thermal responsive materials with relevant melting points such as wax, and/or other materials which change their state and/or form in response to a temperature change.

In some embodiments, airflow through the device (for example in response to inhalation) causes a temperature change which affects the shape changing element.

In some embodiments, one or more mechanical elements such as a spring, a leaflet, a pin and/or others are used in addition or instead of the shape changing element to open the cover.

In some embodiments, closure of the cover (for example following use of the source material contained within it) is achieved using the same shape changing element (e.g. by using a 2-way shape memory material). For example, cooling of transformable body 2700 causes it to return to its original shape and/or deform again to such shape that allows the cover to return to its original position. Additionally or alternatively, closure of the cover is achieved using a different shape changing element, for example using a second transformable body positioned to close the cover. Optionally, the opposing second transformable body expands or contracts in a delayed manner relative to first transformable body 2700 (for example after 0.5 second, 1 second, 3 seconds, 4 seconds or intermediate, longer or shorter time periods) to close the cover following use of the section. Optionally, the delay is achieved by using a thermally isolating material which slows the transfer of heat to the second transformable body, and/or using a fuse that burns out when heat is applied.

Additionally or alternatively, closure is achieved by one or more mechanical elements for example a spring shaped, sized and positioned to oppose expansion of the transformable body.

In some embodiments, transformable body includes one or more shape memory materials such as shape memory polymers (e.g. foam), thermal expansion components, a component configured to evaporate thereby leading to expansion of another, and others.

In some examples, cover 2702 comprises a silicone foil.

Figure 28:
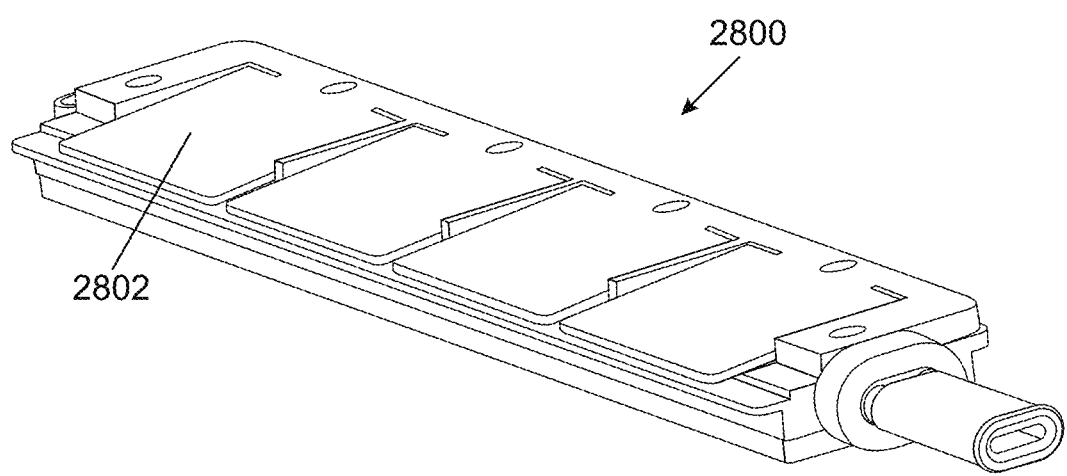
FIG. 28 is an isometric view of an inhaler device comprising a linear arrangement of independently accessible source material sections, according to some embodiments.

FIG. 28 is an isometric view of an inhaler device 2800 comprising a linear arrangement of independently accessible source material sections, according to some embodiments.

In some embodiments, each source material section comprises a cover 2802 configured to be opened separately from the one or more other covers. Optionally, cover 2802 is opened by a shape-memory mechanism. In some embodiments, cover 2802 itself comprises shape memory material, which deforms, moves and/or otherwise changes in shape or position, thereby enabling air to flow to and optionally through at least a portion of the source material protected by cover 2802.

Figures 29A, 29B:
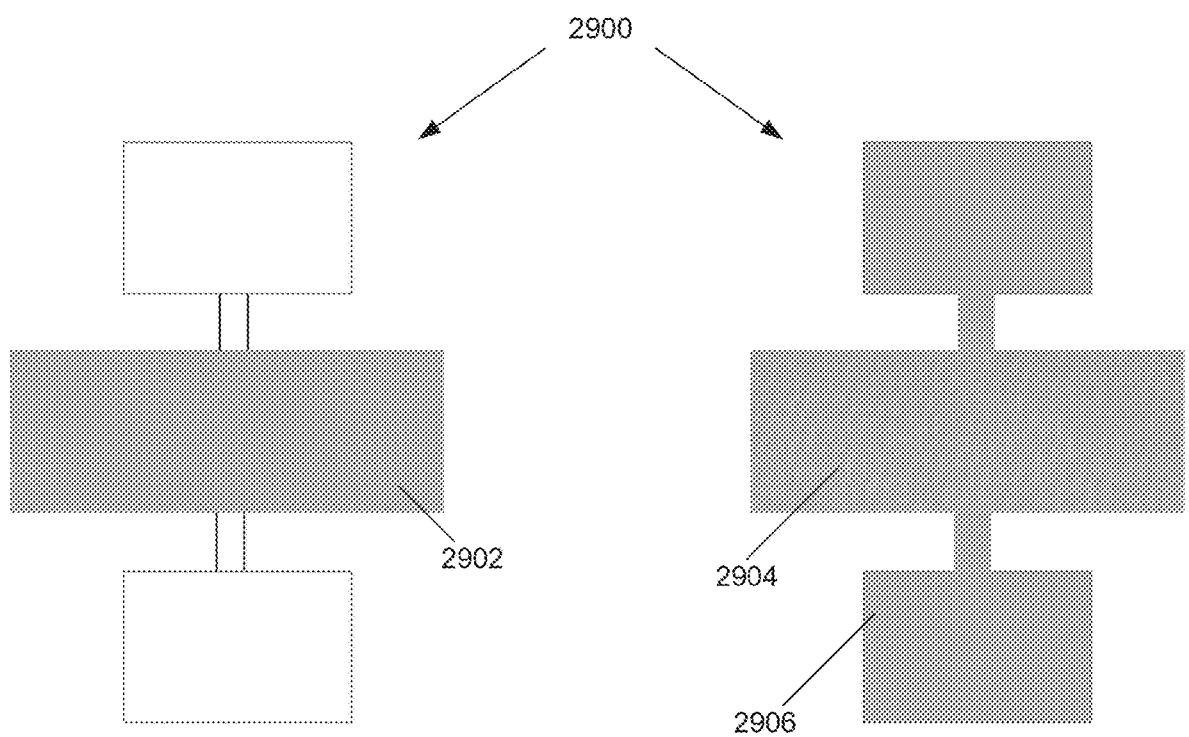
FIGS. 29A-B are schematic top views of an arrangement in which a fluid having a varying viscosity is used for sealing source material, according to some embodiments.

FIGS. 29A-B are schematic top views of an arrangement 2900 in which a fluid having a varying viscosity is used for sealing source material, according to some embodiments.

In some embodiments, a fluid that changes its viscosity in response to a temperature change, for example Silicone oil, provides a sealing of the source material which prevents airflow through. Optionally, a fluid with varying viscosity (indicated in the figure by the opaque colored surface) is layered across a mesh or other frame 2902 containing the source material. FIG. 29A illustrates a non-heated (cold) state in which the fluid exhibits a viscosity high enough to seal the source material underneath it, in accordance with some embodiments. FIG. 29B shows a heated state in which the viscosity decreases, causing the fluid to flow via capillary channels 2904 and into one or more side chambers 2906. In some embodiments, flowing of the fluid away from the mesh or frame of the source material exposes the source material to the flow of air.

In some embodiments, a temperature change produces a change in the surface tension of a fluid. Optionally, a change in surface tension and in viscosity results in capillary motion of the fluid which exposes at least a part of the source material to air.

In some embodiments, when heating is terminated and the fluid cools down, fluid spontaneously moves back to cover the exposed area. Optionally, the fluid flows (for example through capillary channels) due to changes in surface tension and/or wetting properties of the fluid.

Figure 30A:
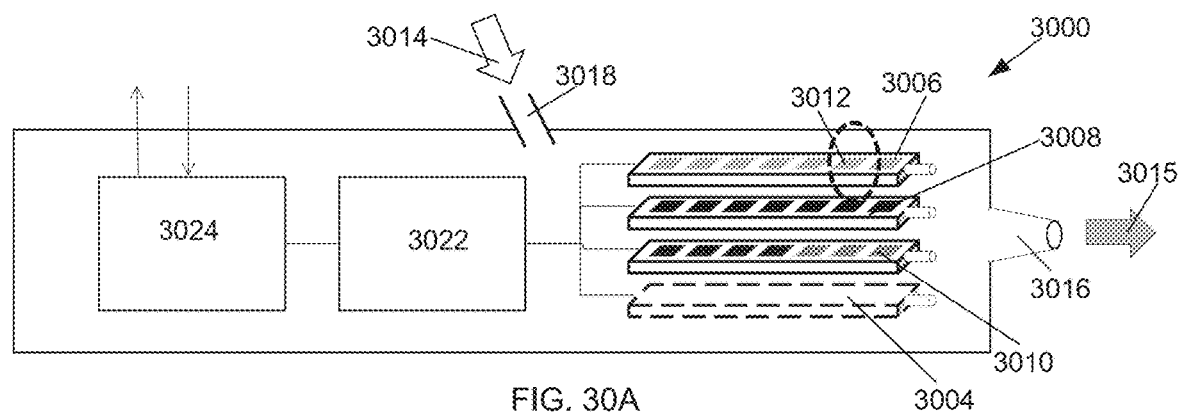
FIGS. 30A-B schematically illustrate an inhaler device configured to receive a plurality of source material cartridges, according to some embodiments.
Figure 30B:
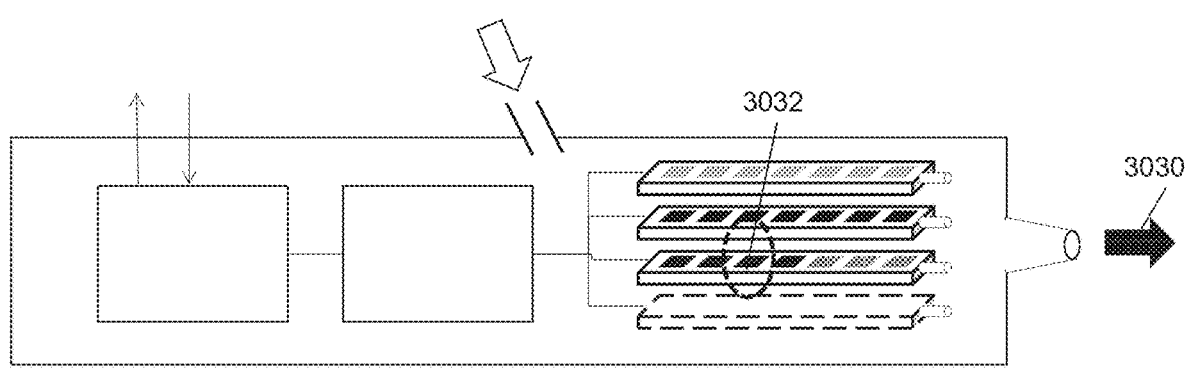

FIGS. 30A-B schematically illustrate an inhaler device configured to receive a plurality of source material cartridges, according to some embodiments.

In some embodiments, inhaler device 3000 comprises a plurality of recesses, slots, receptacles, connectors and/or other structures each configured for receiving one or more source material cartridges. In the example shown, device 3000 comprises an empty receptacle 3004 and three source material cartridges 3006, 3008, 3010 received within three respective receptacles. Examples for such cartridges may include cartridges and/or devices such as described herein, for example in FIGS. 8A-8B, 9, 10A-10F, 11B, 12C-12D, 16A-16B, 22, 23, 26, 28, and 31A-31B.

In some embodiments, each cartridge comprises a plurality of source material sections 3012. In some embodiments, for example as shown in cartridge 3006, the plurality of source material sections include identical content, for example including the same plant or plant compositions and/or the same active substance or compositions of active substances. Alternatively, for example as shown in cartridge 3010, different source material sections comprise different content, for example different plants or plant compositions and/or different active substance or compositions of active substances.

In some embodiments, a specific cartridge and/or a specific source material section within a cartridge is addressed according to a predefined regimen. Additionally or alternatively, a specific cartridge and/or a specific source material section within a cartridge is addressed upon demand, for example selected by a user according to their needs and/or desires. In this example, FIG. 30A illustrates selecting of a source material section from cartridge 3006; FIG. 30B illustrates selecting of a source material section from cartridge 3010.

In some embodiments, during use, source material of one or more selected sections is heated (for example using a heating element such as described hereinabove), and air 3014 that was drawn into the device and/or otherwise entering the device (for example via tract 3018) is allowed and/or directed to flow through the material of the selected section. Air 3015 imbued with the released active substance(s) is then delivered to a user via an output 3016 of the device (for example comprising a mouthpiece). In some embodiments, air imbued with the active substance exits the inhaler in response to inhalation of the user. Additionally or alternatively, the device includes a fan or source of pressurized air (not shown) that can augment and/or replace the force of inhalation of a user.

In some embodiments, the selected sections differ in content, so that different active substances or compositions thereof are released from each of the sections to be delivered to the user. For example, in FIG. 30A, air 3015 imbued with the active substance(s) released from source material section 3012 exits the inhaler device to be delivered to the user; in FIG. 30B, air 3030 imbued with a different active substance and/or different composition of active substances (as compared to the active substance or composition thereof released from section 3012 in FIG. 30A) released from source material section 3032.

In some embodiments, device 3000 comprises a controller 3022 configured for controlling selection and/or access to one or more specific source material sections and/or access to a selected cartridge. Optionally, two or more sections are accessed simultaneously to obtain a selected amount of active substance, a selected composition of active substances, and/or a selected effect on the patient. Optionally, different airflow and/or heating regimes are used for each of a plurality of sections accessed simultaneously, thereby affecting the composition or proportion of active substances in the airflow towards the user.

Optionally, the controller selects sections that are identical in content. Alternatively, the controller selects sections that differ in content. Optionally, the controller selects sections from the same cartridge. Alternatively, the controller selects sections from different cartridges.

In some embodiments, controller 3022 is configured for selecting source material sections for use according to a predetermined order, for example according to a regimen.

Additionally or alternatively to a controller, device 3000 comprises manual control (for example an actuator such as a slider) configured for selecting and/or enabling heating and/or airflow access to a selected section.

In some embodiments, the controller and/or manual control are configured to allow "mix and match" of different source material sections according to their content.

In some embodiments, multiple source material sections having contents that differ from each other are selected in order to treat a certain medical condition. Examples of active substance compositions and the medical condition that can potentially be treated using said active substances may include: active agents that provide a synergistic effect, active agents that provide the same effect but each with different advantages or disadvantages, active agents that potentiate or attenuate other one another or other active agents (e.g., alter the effective therapeutic window or therapeutic index of one-another), active agents that provide contradictory effect, such as, for example, THC is counteracted by CBD, and active agents that have counteractive but desired effects and need to be spaced apart.

Some active agents' combinations, which can be effectively delivered using the devices provided herein, according to embodiments of the present disclosure, include, without limitation, nicotine and THC, caffeine and THC and CBD and THC. Some combinations are intended for recreational use, and may include combining or changing between different tobacco blends, tobacco having different added active substances, different *cannabis* strains or blends, different plant material for other plants and any combination thereof.

In some embodiments, selection of multiple source material sections is performed to accurately control the amounts of active substance(s) provided, for example by using different source material sections that include different amounts of active substance. For example, a first source material section including 5 mg of an active substance can be delivered along with a second source material section including only 1 mg of an active substance, to reach a precise total amount of 6 mg active substance.

In some embodiments, device 3000 comprises a communication module 3024. Optionally, communication module is configured for sending and/or receiving data from one or more of a user input device; a database; a memory; an online data source; a physician; and/or others. Optionally, selection of source material section(s) for use is performed according to instructions received via the communication module. In some embodiments, data received from user input device comprises feedback regarding the effect of treatment. Optionally, the feedback is collected by one or more sensors of the user input device. In some embodiments, treatment is controlled (for example adjusted from a predefined regimen) according to the received feedback data.

Figure 31A:
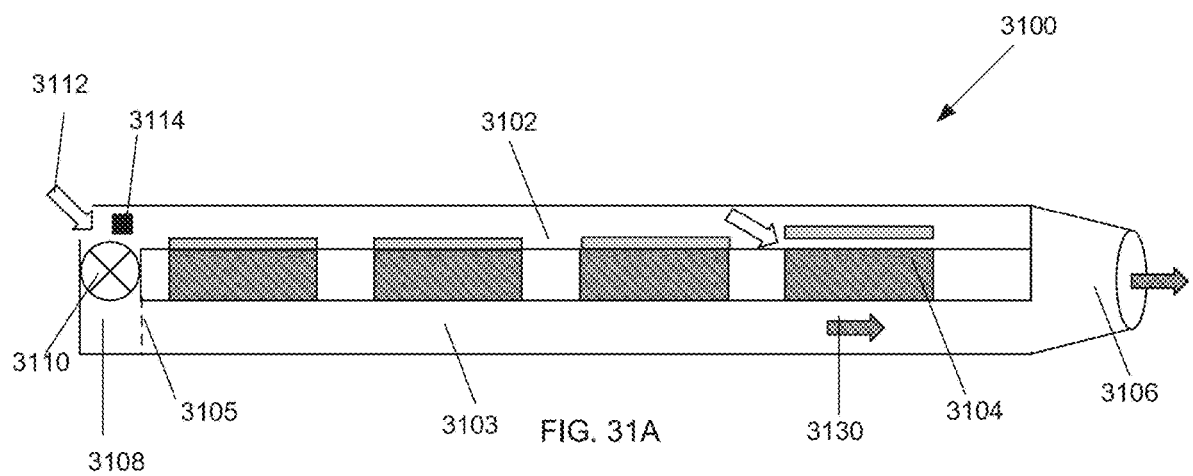
FIGS. 31A-B schematically illustrate an airflow regime through a device comprising a plurality of source material sections, according to some embodiments.
Figure 31B:
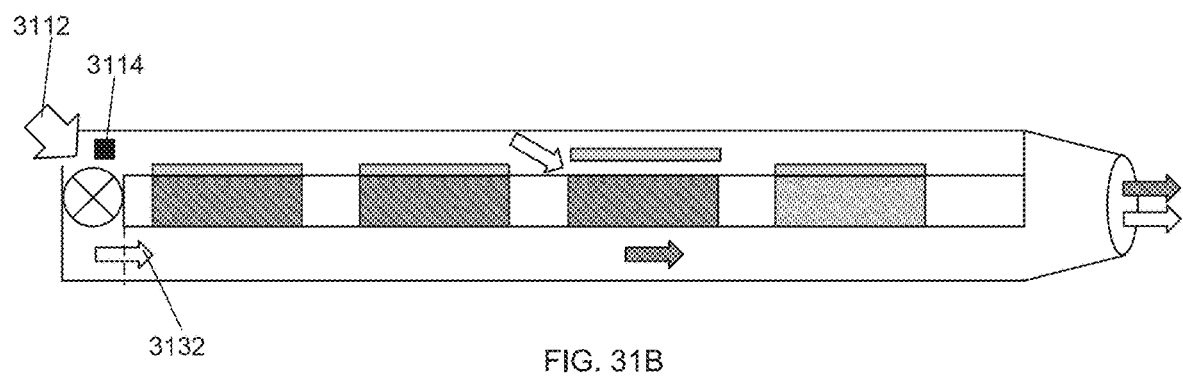

FIGS. 31A-B schematically illustrate an airflow regime through a device comprising a plurality of source material sections, according to some embodiments.

In some embodiments, device 3100 comprises one or more inflow conduits 3102 through which incoming airflow 3112 that enters the device flows to and through an open source material section 3104. As shown, flow 3130 imbued with active substance from the source material flows from section 3104 through a carrier conduit 3103 that extends to mouthpiece component 3106 to be delivered to the user. In some embodiments, the device comprises a bypass conduit 3108 which joins carrier conduit 3013 without passing through the source material, for example joining at juncture 3105. Alternatively, in some embodiments, bypass conduit 3108 extends directly to mouthpiece component 3106, separately from carrier conduit 3103.

In some embodiments, a valve 3110 is positioned at an opening of the bypass conduit to regulate incoming flow into the bypass conduit. In use, flow into the bypass conduit is regulated in response to carrier airflow through the device (e.g. through selected source material section(s)). Optionally, as shown in FIG. 31A, when the rate of incoming airflow 3112 is within a predefined range, valve 3110 is maintained closed. If the rate of incoming airflow is higher than a threshold, as shown in FIG. 31B, valve 3110 opens to shunt at least a portion 3132 of incoming airflow 3112 to the bypass conduit. In some embodiments, the incoming airflow rate, velocity, volume, and/or pressure is determined by a sensor 3114.

In some embodiments, inhalation below a threshold will not trigger heating of the source material. Optionally is such situation an indication is provided to the user (e.g. a visible and/or audible and/or sensible indication) to increase inhalation efforts.

In some embodiments, device 3110 is a stand-alone device. Alternatively, device 3110 forms a cartridge received in an inhaler device. Optionally, in the latter (when device 3110 functions as a cartridge) bypass conduit 3108 (with or without valve 3110 and/or sensor 3114) forms a part of the inhaler device and not of the cartridge. Alternatively, bypass conduit 3108 is a part of the cartridge.

In some embodiments, valve 3110 is operated automatically, for example by a controller. Optionally, a position of valve 3110 is set in accordance with a flow-related indication received from sensor 3114. Additionally or alternatively, valve 3110 opens mechanically at a given flow.

The terms "comprises", "comprising", "includes", "including", "having" and their conjugates mean "including but not limited to".

The term "consisting of" means "including and limited to".

The term "consisting essentially of" means that the composition, method or structure may include additional ingredients, steps and/or parts, but only if the additional ingredients, steps and/or parts do not materially alter the basic and novel characteristics of the claimed composition, method or structure.

As used herein, the singular form "a", "an" and "the" include plural references unless the context clearly dictates otherwise. For example, the term "a compound" or "at least one compound" may include a plurality of compounds, including mixtures thereof.

Throughout this application, various embodiments of this invention may be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

Whenever a numerical range is indicated herein, it is meant to include any cited numeral (fractional or integral) within the indicated range. The phrases "ranging/ranges between" a first indicate number and a second indicate number and "ranging/ranges from" a first indicate number "to" a second indicate number are used herein interchangeably and are meant to include the first and second indicated numbers and all the fractional and integral numerals therebetween.

As used herein the term "method" refers to manners, means, techniques and procedures for accomplishing a given task including, but not limited to, those manners, means, techniques and procedures either known to, or readily developed from known manners, means, techniques and procedures by practitioners of the chemical, pharmacological, biological, biochemical and medical arts.

As used herein, the term "treating" includes abrogating, substantially inhibiting, slowing or reversing the progression of a condition, substantially ameliorating clinical or aesthetical symptoms of a condition or substantially preventing the appearance of clinical or aesthetical symptoms of a condition.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

What is claimed is:

1. A source material cartridge, comprising:
    an elongate housing comprising a plurality of sections arranged along a long axis of said housing, each of said plurality of sections comprising a source material including at least one active substance releasable from said source material by vaporization; said source material arranged to allow a flow of air therethrough; wherein said source material in each of said plurality of sections is protected by a sealant impermeable to air;
    a cart slidably mounted on said elongate housing, said cart configured for sliding along at least a portion of said long axis of said housing between multiple locations, each location comprising one or more sections selected out of said plurality of sections, said cart configured for locally opening said sealant of each of said one or more selected sections to allow air to flow through said source material;
    said cart further configured for:
    applying an electrical current to a heating element of each of said one or more selected sections.

2. The cartridge according to claim 1, wherein said plurality of sections are arranged linearly along said long axis of said housing.

3. The cartridge according to claim 2, wherein an amount of active substance varies along said long axis of said housing.

4. The cartridge according to claim 1, wherein said plurality of sections are separated from each other by an air-sealed barrier.

5. The cartridge according to claim 1, wherein the source material within at least one of said plurality of sections comprises between 1-10% nicotine.

6. The cartridge according to claim 1, wherein a layer of source material within each of said plurality of sections is no more than 1 mm thick.

7. The cartridge according to claim 1, wherein different sections out of said plurality of sections comprise different source materials.

8. The cartridge according to claim 1, wherein said plurality of sections comprise different active substances or compositions thereof.

9. The cartridge according to claim 1, wherein said sealant is configured to at least one selected from the group consisting of:
    a. open as a result of being heated;
    b. heat said source material.

10. The cartridge according to claim 1, wherein said plurality of sections are separated from each other by at least one of a thermal insulation and an electrical insulation.

11. The cartridge according to claim 1, wherein the source material is formed as a solid mass.

12. The cartridge according to claim 1, wherein said sealant is electrically resistive.

13. The cartridge according to claim 12, wherein said sealant is configured to heat the source material.

14. The cartridge according to claim 1, wherein said sealant is configured to be unsealed by heating generated by said applying of an electrical current.

15. The cartridge according to claim 1, wherein said housing comprises an elongate slit extending along said at least a portion of said long axis, and said cart is seated in said slit and slidable along its length.

16. The cartridge according to claim 15, wherein said cart is shaped for manual sliding along said slit by a user.

17. The cartridge according to claim 1, wherein said cart is configured for selectively directing airflow to and through each of said one or more selected sections.

18. The cartridge according to claim 17, wherein said cart is configured for directing said airflow by comprising a nozzle which directs said airflow.

19. The cartridge according to claim 1, wherein said cart comprises a plurality of electrodes which is configured to apply an electrical current to each of said one or more selected sections when said cart is positioned at each of said multiple locations.

20. The cartridge according to claim 19, wherein said cartridge comprises an insulator in the form of a longitudinally extending scaffold which is configured to separates said plurality of electrodes of said cart when said plurality of electrodes contacts each of said one or more selected sections.

21. The cartridge according to claim 1, comprising a ratchet which is configured to advances said cart in a single direction along said elongate housing.

22. The cartridge according to claim 1, comprising a light or color indicator configured to move along with said cart for indicating remaining or used sections out of said plurality of sections.

\* \* \* \* \*